US005689055A

United States Patent [19]

Meyerowitz et al.

[11] Patent Number: 5,689,055

[45] Date of Patent: Nov. 18, 1997

[54] PLANTS HAVING MODIFIED RESPONSE TO ETHYLENE

[75] Inventors: Elliott M. Meyerowitz; Caren Chang, both of Pasadena, Calif.; Anthony B. Bleecker, Madison, Wis.

[73] Assignee: California Institue of Technology, Pasadena, Calif.

[21] Appl. No.: 530,010

[22] Filed: Sep. 19, 1995

Related U.S. Application Data

[63] Continuation of Ser. No. 86,555, Jul. 1, 1993, abandoned.

[51] Int. Cl.[6] .............................. A01H 4/00; C12N 5/14; C12N 15/29

[52] U.S. Cl. .............................. 800/205; 800/DIG. 44; 536/23.6; 435/172.3; 435/240.4

[58] Field of Search .............................. 800/205, DIG. 44, 800/15; 536/23.6; 435/172.3, 320.1, 240.4, 69.1

[56] References Cited

U.S. PATENT DOCUMENTS

| | | | |
|---|---|---|---|
| 4,743,548 | 5/1988 | Crossway et al. | 435/172.3 |
| 4,762,785 | 8/1988 | Comai . | |
| 4,769,061 | 9/1988 | Comai | 435/240.4 |
| 4,801,540 | 1/1989 | Hiatt et al. | 435/172.3 |
| 4,943,674 | 7/1990 | Houck et al. | 800/205 |
| 4,956,282 | 9/1990 | Goodman et al. | 435/172.3 |
| 5,068,193 | 11/1991 | Comai | 435/252.3 |
| 5,106,739 | 4/1992 | Comai et al. | 435/172.3 |
| 5,107,065 | 4/1992 | Shewmaker et al. | 800/205 |
| 5,110,728 | 5/1992 | Kridl et al. | 435/69.1 |
| 5,147,792 | 9/1992 | Perchorowicz et al. | 435/134 |
| 5,175,095 | 12/1992 | Martineau et al. | 435/69.1 |
| 5,177,011 | 1/1993 | Shewmaker et al. | 435/172.3 |
| 5,177,307 | 1/1993 | Houck et al. | 800/205 |

FOREIGN PATENT DOCUMENTS

| | | |
|---|---|---|
| 8912386 | 12/1989 | WIPO . |
| 9001260 | 2/1990 | WIPO . |
| 9101324 | 2/1991 | WIPO . |
| 9101373 | 2/1991 | WIPO . |
| 9211382 | 7/1992 | WIPO . |
| 9212249 | 7/1992 | WIPO . |
| WO 9307264 | 4/1993 | WIPO . |

OTHER PUBLICATIONS

"Ethylene in Plant Biology", 2d ed., F.B. Abeles, P.W. Morgan and M.E. Saltveit, Jr., eds. (San Diego), Academic Press, Inc. pp. 242–263, 1992.

Chang, et al. (1992 Feb.) Biochemical Society Transactions 20(1): 73–75.

Arondel, et al. (20 Nov. 1992) Science 258: 1353–1355.

Giraudat, et al. (Oct. 1992) The Plant Cell 4: 1251–1261.

Matzke, et al. (1991) Plant Molecular Biology 16: 821–830.

Bleecker, et al. (1988) Science 241: 1086–1089.

Bleecker, A.B. et al. (1988) *Science* 241:1086–1089, "Insensitivity to Ethylene Conferred by a Cominant Mutation in *Arabidopsis thaliana*".

Guzmán, P. et al. (1990) *The Plant Cell* 2:513–523, "Exploiting the Triple Response of Arabidopsis to Identify Ethylene–Related Mutants".

Kleber, J.J. et al. (1993) *Cell* 72:427–441, "CTR1, a Negative Regulator of the Ethylene Response Pathway in Arabidopsis, Encodes a Member of the Raf Family of Protein Kinases".

Harpham, N.V.J. et al. (1991) *Annals of Botany* 68:55–61, "The Effect of Ethylene on the Growth and Development of Wild–type and Mutant *Arabidopsis thaliana* (L.) Heynh".

Oeller, P.W. et al. (1991) *Science* 254:437–439, "Reversible Inhibition of Tomato Fruit Senescence by Antisense RNA".

McCormick, S. et al. (1986) *Plant Cell Reports* 5:81–84, "Leaf disc transformation of cultivated tomato (*L. ezculentum*) using *Agrobacterium tumefaciens*".

Horsch, R.B. et al. (1985) *Science* 227:1229–31, "A Simple and General Method for Transferring Genes into Plants".

Trolinder, N.L. et al. (1987) *Plant Cell Reports* 6:231–234, "Somatic embyrogenesis and plant regeneration in cotton (*Gossypium hirsutum* L.)".

Bollmann, J. et al. (1991) *The Plant Cell* 3:1327–1336, "Allelic Interactions at the nivea Locus of Antirrhinum".

Matzke, M.A. et al. (1993) *Mol. Gen. Genet.* 236:379–386, "A variety of epistatic interactions can occur between partially homologous transgene loci brought together by sexual crossing".

McBride, K.E. et al. (1990) *Plant Molecular Biology* 14:269–276, "Improved binary vectors for Agrobacterium–mediated plant transformation".

Jorgensen, R. (1991) *Tibtech* 9:266–267, "Beyond antisense–How do transgenes interact with homologous plant genes?".

Matzke, M.A. et al. (1991) *Plant Molecular Biology* 16:821–830, "Differential inactivation and methylation of a transgene in plants by two suppressor loci containing homologous sequences".

Chang et al., "Restriction Fragment Length Polymorphism Linkage Map for *Arabidopsis thaliana*" *PNAS USA,* 85:6856–6860 (1988).

(List continued on next page.)

*Primary Examiner*—Che S. Chereskin

*Attorney, Agent, or Firm*—Richard F. Trecartin; Flehr Hohbach Test Albritton & Herbert LLP

[57] ABSTRACT

The invention includes transformed plants having at least one cell transformed with a modified ETR nucleic acid. Such plants have a phenotype characterized by a decrease in the response of at least one transformed plant cell to ethylene as compared to a plant not containing the transformed plant cell. Tissue and/or temporal specificity for expression of the modified ETR nucleic acid is controlled by selecting appropriate expression regulation sequences to target the location and/or time of expression of the transformed nucleic acid. The plants are made by transforming at least one plant cell with an appropriate modified ETR nucleic acid, regenerating plants from one or more of the transformed plant cells and selecting at least one plant having the desired phenotype.

8 Claims, 29 Drawing Sheets

OTHER PUBLICATIONS

Pickett et al., "Recessive Mutation at the ETR–2 Locus of *Arabidopsis thaliana* Confers Resistance to Some Effects of Ethylene Exposure," *J. Cell. Biochem.*, Supp. 0 (13 part D):324 (1989). Symposium on Plant Gene Transfer, 18th Annual UCLA Symposium, Park City, Utah, USA: Apr. 1–7, 1989.

Boswell et al., "Computational Molecular Biology Sources and Methods for Sequence Analysis," (Lest, ed.) Oxford University Press, Oxford 1989, pp. 170–171.

Chang et al., "Arabidopsis Ethylene–Response Gene ETR1: Similarity of Product of Two–Component Regulators," *Science*, 262:539–544 (1993).

Chang et al., "Eukaryotes have two–component Signal Transducers," *Res. Microb.*, 1459:481–486 (1994).

Lawton et al., "Acquired–Resistance Signal–Transduction in Arabidopsis is Ethylene Independent," *Cell*, 6(5):581–588 (1994).

Chang, C., et al., "The TMKI Gene from Arabidopsis Codes for a Protein with Structural and Biochemical Characteristics of a Receptor Protein Kinase," *Plant Cell*, 4:1263 (1992).

Bleeker, A. B., "Genetic Analysis of Ethylene Responses in *Arabidopsis thaliana,*" *Great Britain Society for Experimental Biology* (1991).

AAAGATAGTA TTTGTTGATA AATATGGGGA TATTTATCCT ATATTATCTG 50
TATTTTTCTT ACCATTTTTA CTCTATTCCT TTATCTACAT TACGTCATTA 100
CACTATCATA AGATATTTGA ATGAACAAAT TCATGCACCC ACCAGCTATA 150
TTACCCTTTT TTATTAAAAA AAAACATCTG ATAATAATAA CAAAAAAATT 200
AGAGAAATGA CGTCGAAAAA AAAAGTAAGA ACGAAGAAGA AGTGTTAAAC 250
CCAACCAATT TTGACTTGAA AAAAAGCTTC AACGCTCCCC TTTTCTCCTT 300
CTCCGTCGCT CTCCGCCGCG TCCCAAATCC CCAATTCCTC CTCTTCTCCG 350
ATCAATTCTT CCCAAGTAAG CTTCTTCTTC CTCGATTCTC TCCTCAGATT 400
GTTTCGTGAC TTCTTTATAT ATATTCTTCA CTTCCACAGT TTTCTTCTGT 450
TGTTGTCGTC GATCTCAAAT CATAGAGATT GATTAACCTA ATTGGTCTTT 500
ATCTAGTGTA ATGCATCGTT ATTAGGAACT TTAAATTAAG ATTTAATCGT 550
TAATTTCATG ATTCGGATTC GAATTTTACT GTTCTCGAGA CTGAAATATG 600
CAACCTATTT TTTCGTAATC GTTGTGATCG AATTCGATTC TTCAGAATTT 650
ATAGCAATTT TGATGCTCAT GATCTGTCTA CGCTACGTTC TCGTCGTAAA 700
TCGAAGTTGA TAATGCTATG TGTTTGTTAC ACAGGTGTGT GTATGTGTGA 750
GAGAGGAACT ATAGTGTAAA AAATTCATAA TGGAAGTCTG CAATTGTATT 800
GAACCGCAAT GGCCAGCGGA TGAATTGTTA ATGAAATACC AATACATCTC 850
CGATTTCTTC ATTGCGATTG CGTATTTTTC GATTCCTCTT GAGTTGATTT 900
ACTTTGTGAA GAAATCAGCC GTGTTTCCGT ATAGATGGGT ACTTGTTCAG 950
TTTGGTGCTT TTATCGTTCT TTGTGGAGCA ACTCATCTTA TTAACTTATG 1000
GACTTTCACT ACGCATTCGA GAACCGTGGC GCTTGTGATG ACTACCGCGA 1050
AGGTGTTAAC CGCTGTTGTC TCGTGTGCTA CTGCGTTGAT GCTTGTTCAT 1100
ATTATTCCTG ATCTTTTGAG TGTTAAGACT CGGGAGCTTT TCTTGAAAAA 1150
TAAAGCTGCT GAGCTCGATA GAGAAATGGG ATTGATTCGA ACTCAGGAAG 1200
AAACCGGAAG GCATGTGAGA ATGTTGACTC ATGAGATTAG AAGCACTTTA 1250
GATAGACATA CTATTTTAAA GACTACACTT GTTGAGCTTG GTAGGACATT 1300
AGCTTTGGAG GAGTGTGCAT TGTGGATGCC TACTAGAACT GGGTTAGAGC 1350
TACAGCTTTC TTATACACTT CGTCATCAAC ATCCCGTGGA GTATACGGTT 1400
CCTATTCAAT TACCGGTGAT TAACCAAGTG TTTGGTACTA GTAGGGCTGT 1450
AAAAATATCT CCTAATTCTC CTGTGGCTAG GTTGAGACCT GTTTCTGGGA 1500
AATATATGCT AGGGGAGGTG GTCGCTGTGA GGGTTCCGCT TCTCCACCTT 1550

FIG. 2A

```
TCTAATTTTC AGATTAATGA CTGGCCTGAG CTTTCAACAA AGAGATATGC    1600
TTTGATGGTT TTGATGCTTC CTTCAGATAG TGCAAGGCAA TGGCATGTCC    1650
ATGAGTTGGA ACTCGTTGAA GTCGTCGCTG ATCAGGTTTT ACATTGCTGA    1700
GAATTTCTCT TCTTTGCTAT GTTCATGATC TTGTCTATAA CTTTTCTTCT    1750
CTTATTATAG GTGGCTGTAG CTCTCTCACA TGCTGCGATC CTAGAAGAGT    1800
CGATGCGAGC TAGGGACCTT CTCATGGAGC AGAATGTTGC TCTTGATCTA    1850
GCTAGACGAG AAGCAGAAAC AGCAATCCGT GCCCGCAATG ATTTCCTAGC    1900
GGTTATGAAC CATGAAATGC GAACACCGAT GCATGCGATT ATTGCACTCT    1950
CTTCCTTACT CCAAGAAACG GAACTAACCC CTGAACAAAG ACTGATGGTG    2000
GAAACAATAC TTAAAAGTAG TAACCTTTTG GCAACTTTGA TGAATGATGT    2050
CTTAGATCTT TCAAGGTTAG AAGATGGAAG TCTTCAACTT GAACTTGGGA    2100
CATTCAATCT TCATACATTA TTTAGAGAGG TAACTTTTGA ACAGCTCTAT    2150
GTTTCATAAG TTTATACTAT TTGTGTACTT GATTGTCATA TTGAATCTTG    2200
TTGCAGGTCC TCAATCTGAT AAAGCCTATA GCGGTTGTTA AGAAATTACC    2250
CATCACACTA AATCTTGCAC CAGATTTGCC AGAATTTGTT GTTGGGGATG    2300
AGAAACGGCT AATGCAGATA ATATTAAATA TAGTTGGTAA TGCTGTGAAA    2350
TTCTCCAAAC AAGGTAGTAT CTCCGTAACC GCTCTTGTCA CCAAGTCAGA    2400
CACACGAGCT GCTGACTTTT TTGTCGTGCC AACTGGGAGT CATTTCTACT    2450
TGAGAGTGAA GGTTATTATC TTGTATCTTG GGATCTTATA CCATAGCTGA    2500
AAGTATTTCT TAGGTCTTAA TTTTGATGAT TATTCAAATA TAGGTAAAAG    2550
ACTCTGGAGC AGGAATAAAT CCTCAAGACA TTCCAAAGAT TTTCACTAAA    2600
TTTGCTCAAA CACAATCTTT AGCGACGAGA AGCTCGGGTG GTAGTGGGCT    2650
TGGCCTCGCC ATCTCCAAGA GGTTTGAGCC TTATTAAAAG ACGTTTTTTT    2700
CCAACTTTTT CTTGTCTTCT GTGTTGTTAA AAGTTTACTC ATAAGCGTTT    2750
AATATGACAA GGTTTGTGAA TCTGATGGAG GGTAACATTT GGATTGAGAG    2800
CGATGGTCTT GGAAAAGGAT GCACGGCTAT CTTTGATGTT AAACTTGGGA    2850
TCTCAGAACG TTCAAACGAA TCTAAACAGT CGGGCATACC GAAAGTTCCA    2900
GCCATTCCCC GACATTCAAA TTTCACTGGA CTTAAGGTTC TTGTCATGGA    2950
TGAGAACGGG TTAGTATAAG CTTCTCACCT TTCTCTTTGC AAAATCTCTC    3000
GCCTTACTTC TTGCAAATGC AGATATTGGC GTTTAGAAAA AACGCAAATT    3050
TAATCTTATG AGAAACCGAT GATTATTTTG GTTGCAGGGT AAGTAGAATG    3100
```

*FIG. 2B*

```
GTGACGAAGG GACTTCTTGT ACACCTTGGG TGCGAAGTGA CCACGGTGAG   3150
TTCAAACGAG GAGTGTCTCC GAGTTGTGTC CCATGAGCAC AAAGTGGTCT   3200
TCATGGACGT GTGCATGCCC GGGGTCGAAA ACTACCAAAT CGCTCTCCGT   3250
ATTCACGAGA AATTCACAAA ACAACGCCAC CAACGGCCAC TACTTGTGGC   3300
ACTCAGTGGT AACACTGACA AATCCACAAA AGAGAAATGC ATGAGCTTTG   3350
GTCTAGACGG TGTGTTGCTC AAACCCGTAT CACTAGACAA CATAAGAGAT   3400
GTTCTGTCTG ATCTTCTCGA GCCCCGGGTA CTGTACGAGG GCATGTAAAG   3450
GCGATGGATG CCCCATGCCC CAGAGGAGTA ATTCCGCTCC CGCCTTCTTC   3500
TCCCGTAAAA CATCGGAAGC TGATGTTCTC TGGTTTAATT GTGTACATAT   3550
CAGAGATTGT CGGAGCGTTT TGGATGATAT CTTAAAACAG AAAGGGAATA   3600
ACAAAATAGA AACTCTAAAC CGGTATGTGT CCGTGGCGAT TTCGGTTATA   3650
GAGGAACAAG ATGGTGGTGG TATAATCATA CCATTTCAGA TTACATGTTT   3700
GACTAATGTT GTATCCTTAT ATATGTAGTT ACATTCTTAT AAGAATTTGG   3750
ATCGAGTTAT GGATGCTTGT TGCGTGCATG TATGACATTG ATGCAGTATT   3800
ATGGCGTCAG CTTTGCGCCG CTTAGTAGAA CAACAACAAT GGCGTTACTT   3850
AGTTTCTCAA TCAACCCGAT CTCCAAAAC                          3879
```

FIG. 2C

```
AGTAAGAACG AAGAAGAAGT GTTAAACCCA ACCAATTTTG ACTTGAAAAA      50

AAGCTTCAAC GCTCCCCTTT TCTCCTTCTC CGTCGCTCTC CGCCGCGTCC     100

CAAATCCCCA ATTCCTCCTC TTCTCCGATC AATTCTTCCC AAGTGTGTGT     150

ATGTGTGAGA GAGGAACTAT AGTGTAAAAA ATTCATA ATG GAA GTC TGC   199
                                         Met Glu Val Cys
                                          1

AAT TGT ATT GAA CCG CAA TGG CCA GCG GAT GAA TTG TTA ATG    241
Asn Cys Ile Glu Pro Gln Trp Pro Ala Asp Glu Leu Leu Met
  5                  10                  15

AAA TAC CAA TAC ATC TCC GAT TTC TTC ATT GCG ATT GCG TAT    283
Lys Tyr Gln Tyr Ile Ser Asp Phe Phe Ile Ala Ile Ala Tyr
     20                  25                  30

TTT TCG ATT CCT CTT GAG TTG ATT TAC TTT GTG AAG AAA TCA    325
Phe Ser Ile Pro Leu Glu Leu Ile Tyr Phe Val Lys Lys Ser
         35                  40                  45

GCC GTG TTT CCG TAT AGA TGG GTA CTT GTT CAG TTT GGT GCT    367
Ala Val Phe Pro Tyr Arg Trp Val Leu Val Gln Phe Gly Ala
             50                  55                  60

TTT ATC GTT CTT TGT GGA GCA ACT CAT CTT ATT AAC TTA TGG    409
Phe Ile Val Leu Cys Gly Ala Thr His Leu Ile Asn Leu Trp
                 65                  70

ACT TTC ACT ACG CAT TCG AGA ACC GTG GCG CTT GTG ATG ACT    451
Thr Phe Thr Thr His Ser Arg Thr Val Ala Leu Val Met Thr
75                   80                  85

ACC GCG AAG GTG TTA ACC GCT GTT GTC TCG TGT GCT ACT GCG    493
Thr Ala Lys Val Leu Thr Ala Val Val Ser Cys Ala Thr Ala
     90                  95                 100

TTG ATG CTT GTT CAT ATT ATT CCT GAT CTT TTG AGT GTT AAG    535
Leu Met Leu Val His Ile Ile Pro Asp Leu Leu Ser Val Lys
        105                 110                 115

ACT CGG GAG CTT TTC TTG AAA AAT AAA GCT GCT GAG CTC GAT    577
Thr Arg Glu Leu Phe Leu Lys Asn Lys Ala Ala Glu Leu Asp
            120                 125                 130

AGA GAA ATG GGA TTG ATT CGA ACT CAG GAA GAA ACC GGA AGG    619
Arg Glu Met Gly Leu Ile Arg Thr Gln Glu Glu Thr Gly Arg
                135                 140

CAT GTG AGA ATG TTG ACT CAT GAG ATT AGA AGC ACT TTA GAT    661
His Val Arg Met Leu Thr His Glu Ile Arg Ser Thr Leu Asp
145                 150                 155

AGA CAT ACT ATT TTA AAG ACT ACA CTT GTT GAG CTT GGT AGG    703
Arg His Thr Ile Leu Lys Thr Thr Leu Val Glu Leu Gly Arg
    160                 165                 170

ACA TTA GCT TTG GAG GAG TGT GCA TTG TGG ATG CCT ACT AGA    745
Thr Leu Ala Leu Glu Glu Cys Ala Leu Trp Met Pro Thr Arg
        175                 180                 185
```

FIG. 3A

```
ACT GGG TTA GAG CTA CAG CTT TCT TAT ACA CTT CGT CAT CAA     787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT     829
His Pro Val Glu Tyr Thr Val Pro Ile Gln Leu Pro Val Ile
                205                 210

AAC CAA GTG TTT GGT ACT AGT AGG GCT GTA AAA ATA TCT CCT     871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT     913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC     955
Met Leu Gly Glu Val Val Ala Val Arg Val Pro Leu Leu His
        245                 250                 255

CTT TCT AAT TTT CAG ATT AAT GAC TGG CCT GAG CTT TCA ACA     997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT    1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC    1081
Ala Arg Gln Trp His Val His Glu Leu Glu Leu Val Glu Val
285                 290                 295

GTC GCT GAT CAG GTG GCT GTA GCT CTC TCA CAT GCT GCG ATC    1123
Val Ala Asp Gln Val Ala Val Ala Leu Ser His Ala Ala Ile
    300                 305                 310

CTA GAA GAG TCG ATG CGA GCT AGG GAC CTT CTC ATG GAG CAG    1165
Leu Glu Glu Ser Met Arg Ala Arg Asp Leu Leu Met Glu Gln
        315                 320                 325

AAT GTT GCT CTT GAT CTA GCT AGA CGA GAA GCA GAA ACA GCA    1207
Asn Val Ala Leu Asp Leu Ala Arg Arg Glu Ala Glu Thr Ala
            330                 335                 340

ATC CGT GCC CGC AAT GAT TTC CTA GCG GTT ATG AAC CAT GAA    1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA    1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG    1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG    1375
Glu Thr Ile Leu Lys Ser Ser Asn Leu Leu Ala Thr Leu Met
        385                 390                 395
```

*FIG. 3B*

```
AAT GAT GTC TTA GAT CTT TCA AGG TTA GAA GAT GGA AGT CTT     1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA     1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA     1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT     1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT     1585
Val Val Gly Asp Glu Lys Arg Leu Met Gln Ile Ile Leu Asn
        455                 460                 465

ATA GTT GGT AAT GCT GTG AAA TTC TCC AAA CAA GGT AGT ATC     1621
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT     1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA     1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC     1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA     1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC     1837
Ala Thr Arg Ser Ser Gly Gly Ser Gly Leu Gly Leu Ala Ile
            540                 545                 550

TCC AAG AGG TTT GTG AAT CTG ATG GAG GGT AAC ATT TGG ATT     1879
Ser Lys Arg Phe Val Asn Leu Met Glu Gly Asn Ile Trp Ile
                555                 560

GAG AGC GAT GGT CTT GGA AAA GGA TGC ACG GCT ATC TTT GAT     1921
Glu Ser Asp Gly Leu Gly Lys Gly Cys Thr Ala Ile Phe Asp
565                 570                 575

GTT AAA CTT GGG ATC TCA GAA CGT TCA AAC GAA TCT AAA CAG     1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT     2005
Ser Gly Ile Pro Lys Val Pro Ala Ile Pro Arg His Ser Asn
        595                 600                 605
```

FIG. 3C

```
TTC ACT GGA CTT AAG GTT CTT GTC ATG GAT GAG AAC GGG GTA     2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC     2089
Ser Arg Met Val Thr Lys Gly Leu Leu Val His Leu Gly Cys
                625                 630

GAA GTG ACC ACG GTG AGT TCA AAC GAG GAG TGT CTC CGA GTT     2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG     2173
Val Ser His Glu His Lys Val Val Phe Met Asp Val Cys Met
    650                 655                 660

CCC GGG GTC GAA AAC TAC CAA ATC GCT CTC CGT ATT CAC GAG     2215
Pro Gly Val Glu Asn Tyr Gln Ile Ala Leu Arg Ile His Glu
        665                 670                 675

AAA TTC ACA AAA CAA CGC CAC CAA CGG CCA CTA CTT GTG GCA     2257
Lys Phe Thr Lys Gln Arg His Gln Arg Pro Leu Leu Val Ala
            680                 685                 690

CTC AGT GGT AAC ACT GAC AAA TCC ACA AAA GAG AAA TGC ATG     2299
Leu Ser Gly Asn Thr Asp Lys Ser Thr Lys Glu Lys Cys Met
                695                 700

AGC TTT GGT CTA GAC GGT GTG TTG CTC AAA CCC GTA TCA CTA     2341
Ser Phe Gly Leu Asp Gly Val Leu Leu Lys Pro Val Ser Leu
705                 710                 715

GAC AAC ATA AGA GAT GTT CTG TCT GAT CTT CTC GAG CCC CGG     2383
Asp Asn Ile Arg Asp Val Leu Ser Asp Leu Leu Glu Pro Arg
    720                 725                 730

GTA CTG TAC GAG GGC ATG TAAAGGCGAT GGATGCCCCA               2421
Val Leu Tyr Glu Gly Met
        735

TGCCCCAGAG GAGTAATTCC GCTCCCGCCT TCTTCTCCCG TAAAACATCG      2471

GAAGCTGATG TTCTCTGGTT TAATTGTGTA CATATCAGAG ATTGTCGGAG      2521

CGTTTTGGAT GATATCTTAA AACAGAAAGG GAATAACAAA ATAGAAACTC      2571

TAAACCGGTA TGTGTCCGTG GCGATTTCGG TTATAGAGGA ACAAGATGGT      2621

GGTGGTATAA TCATACCATT TCAGATTACA TGTTTGACTA ATGTTGTATC      2671

CTTATATATG TAGTTACATT CTTATAAGAA TTTGGATCGA GTTATGGATG      2721

CTTGTTGCGT GCATGTATGA CATTGATGCA GTATTATGGC GTCAGCTTTG      2771

CGCCGCTTAG TAGAAC                                           2787
```

FIG. 3D

```
AGTAAGAACG AAGAAGAAGT GTTAAACCCA ACCAATTTTG ACTTGAAAAA        50

AAGCTTCAAC GCTCCCCTTT TCTCCTTCTC CGTCGCTCTC CGCCGCGTCC       100

CAAATCCCCA ATTCCTCCTC TTCTCCGATC AATTCTTCCC AAGTGTGTGT       150

ATGTGTGAGA GAGGAACTAT AGTGTAAAAA ATTCATA ATG GAA GTC TGC     199
                                         Met Glu Val Cys
                                          1

AAT TGT ATT GAA CCG CAA TGG CCA GCG GAT GAA TTG TTA ATG      241
Asn Cys Ile Glu Pro Gln Trp Pro Ala Asp Glu Leu Leu Met
 5                  10                  15

AAA TAC CAA TAC ATC TCC GAT TTC TTC ATT GCG ATT GTG TAT      283
Lys Tyr Gln Tyr Ile Ser Asp Phe Phe Ile Ala Ile Val Tyr
    20                  25                  30

TTT TCG ATT CCT CTT GAG TTG ATT TAC TTT GTG AAG AAA TCA      325
Phe Ser Ile Pro Leu Glu Leu Ile Tyr Phe Val Lys Lys Ser
        35                  40                  45

GCC GTG TTT CCG TAT AGA TGG GTA CTT GTT CAG TTT GGT GCT      367
Ala Val Phe Pro Tyr Arg Trp Val Leu Val Gln Phe Gly Ala
            50                  55                  60

TTT ATC GTT CTT TGT GGA GCA ACT CAT CTT ATT AAC TTA TGG      409
Phe Ile Val Leu Cys Gly Ala Thr His Leu Ile Asn Leu Trp
                65                  70

ACT TTC ACT ACG CAT TCG AGA ACC GTG GCG CTT GTG ATG ACT      451
Thr Phe Thr Thr His Ser Arg Thr Val Ala Leu Val Met Thr
75                  80                  85

ACC GCG AAG GTG TTA ACC GCT GTT GTC TCG TGT GCT ACT GCG      493
Thr Ala Lys Val Leu Thr Ala Val Val Ser Cys Ala Thr Ala
    90                  95                  100

TTG ATG CTT GTT CAT ATT ATT CCT GAT CTT TTG AGT GTT AAG      535
Leu Met Leu Val His Ile Ile Pro Asp Leu Leu Ser Val Lys
        105                 110                 115

ACT CGG GAG CTT TTC TTG AAA AAT AAA GCT GCT GAG CTC GAT      577
Thr Arg Glu Leu Phe Leu Lys Asn Lys Ala Ala Glu Leu Asp
            120                 125                 130

AGA GAA ATG GGA TTG ATT CGA ACT CAG GAA GAA ACC GGA AGG      619
Arg Glu Met Gly Leu Ile Arg Thr Gln Glu Glu Thr Gly Arg
                135                 140

CAT GTG AGA ATG TTG ACT CAT GAG ATT AGA AGC ACT TTA GAT      661
His Val Arg Met Leu Thr His Glu Ile Arg Ser Thr Leu Asp
145                 150                 155

AGA CAT ACT ATT TTA AAG ACT ACA CTT GTT GAG CTT GGT AGG      703
Arg His Thr Ile Leu Lys Thr Thr Leu Val Glu Leu Gly Arg
    160                 165                 170

ACA TTA GCT TTG GAG GAG TGT GCA TTG TGG ATG CCT ACT AGA      745
Thr Leu Ala Leu Glu Glu Cys Ala Leu Trp Met Pro Thr Arg
        175                 180                 185
```

FIG. 4A

```
ACT GGG TTA GAG CTA CAG CTT TCT TAT ACA CTT CGT CAT CAA     787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT     829
His Pro Val Glu Tyr Thr Val Pro Ile Gln Leu Pro Val Ile
                205                 210

AAC CAA GTG TTT GGT ACT AGT AGG GCT GTA AAA ATA TCT CCT     871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT     913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC     955
Met Leu Gly Glu Val Val Ala Val Arg Val Pro Leu Leu His
        245                 250                 255

CTT TCT AAT TTT CAG ATT AAT GAC TGG CCT GAG CTT TCA ACA     997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT    1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC    1081
Ala Arg Gln Trp His Val His Glu Leu Glu Leu Val Glu Val
285                 290                 295

GTC GCT GAT CAG GTG GCT GTA GCT CTC TCA CAT GCT GCG ATC    1123
Val Ala Asp Gln Val Ala Val Ala Leu Ser His Ala Ala Ile
    300                 305                 310

CTA GAA GAG TCG ATG CGA GCT AGG GAC CTT CTC ATG GAG CAG    1165
Leu Glu Glu Ser Met Arg Ala Arg Asp Leu Leu Met Glu Gln
        315                 320                 325

AAT GTT GCT CTT GAT CTA GCT AGA CGA GAA GCA GAA ACA GCA    1207
Asn Val Ala Leu Asp Leu Ala Arg Arg Glu Ala Glu Thr Ala
            330                 335                 340

ATC CGT GCC CGC AAT GAT TTC CTA GCG GTT ATG AAC CAT GAA    1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA    1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG    1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG    1375
Glu Thr Ile Leu Lys Ser Ser Asn Leu Leu Ala Thr Leu Met
        385                 390                 395
```

FIG. 4B

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA    1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
        455                 460                 465

ATA GTT GGT AAT GCT GTG AAA TTC TCC AAA CAA GGT AGT ATC    1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
            540                 545                 550

TCC AAG AGG TTT GTG AAT CTG ATG GAG GGT AAC ATT TGG ATT    1879
Ser Lys Arg Phe Val Asn Leu Met Glu Gly Asn Ile Trp Ile
                555                 560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565                 570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
        595                 600                 605
```

FIG. 4C

```
TTC ACT GGA CTT AAG GTT CTT GTC ATG GAT GAG AAC GGG GTA      2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC      2089
Ser Arg Met Val Thr Lys Gly Leu Leu Val His Leu Gly Cys
                625                 630

GAA GTG ACC ACG GTG AGT TCA AAC GAG GAG TGT CTC CGA GTT      2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG      2173
Val Ser His Glu His Lys Val Val Phe Met Asp Val Cys Met
    650                 655                 660

CCC GGG GTC GAA AAC TAC CAA ATC GCT CTC CGT ATT CAC GAG      2215
Pro Gly Val Glu Asn Tyr Gln Ile Ala Leu Arg Ile His Glu
        665                 670                 675

AAA TTC ACA AAA CAA CGC CAC CAA CGG CCA CTA CTT GTG GCA      2257
Lys Phe Thr Lys Gln Arg His Gln Arg Pro Leu Leu Val Ala
            680                 685                 690

CTC AGT GGT AAC ACT GAC AAA TCC ACA AAA GAG AAA TGC ATG      2299
Leu Ser Gly Asn Thr Asp Lys Ser Thr Lys Glu Lys Cys Met
                695                 700

AGC TTT GGT CTA GAC GGT GTG TTG CTC AAA CCC GTA TCA CTA      2341
Ser Phe Gly Leu Asp Gly Val Leu Leu Lys Pro Val Ser Leu
705                 710                 715

GAC AAC ATA AGA GAT GTT CTG TCT GAT CTT CTC GAG CCC CGG      2383
Asp Asn Ile Arg Asp Val Leu Ser Asp Leu Leu Glu Pro Arg
    720                 725                 730

GTA CTG TAC GAG GGC ATG TAAAGGCGAT GGATGCCCCA                2421
Val Leu Tyr Glu Gly Met
        735

TGCCCCAGAG GAGTAATTCC GCTCCCGCCT TCTTCTCCCG TAAAACATCG      2471

GAAGCTGATG TTCTCTGGTT TAATTGTGTA CATATCAGAG ATTGTCGGAG      2521

CGTTTTGGAT GATATCTTAA AACAGAAAGG GAATAACAAA ATAGAAACTC      2571

TAAACCGGTA TGTGTCCGTG GCGATTTCGG TTATAGAGGA ACAAGATGGT      2621

GGTGGTATAA TCATACCATT TCAGATTACA TGTTTGACTA ATGTTGTATC      2671

CTTATATATG TAGTTACATT CTTATAAGAA TTTGGATCGA GTTATGGATG      2721

CTTGTTGCGT GCATGTATGA CATTGATGCA GTATTATGGC GTCAGCTTTG      2771

CGCCGCTTAG TAGAAC                                           2787
```

*FIG. 4D*

```
AGTAAGAACG AAGAAGAAGT GTTAAACCCA ACCAATTTTG ACTTGAAAAA   50

AAGCTTCAAC GCTCCCCTTT TCTCCTTCTC CGTCGCTCTC CGCCGCGTCC   100

CAAATCCCCA ATTCCTCCTC TTCTCCGATC AATTCTTCCC AAGTGTGTGT   150

ATGTGTGAGA GAGGAACTAT AGTGTAAAAA ATTCATA ATG GAA GTC TGC   199
                                        Met Glu Val Cys
                                         1

AAT TGT ATT GAA CCG CAA TGG CCA GCG GAT GAA TTG TTA ATG   241
Asn Cys Ile Glu Pro Gln Trp Pro Ala Asp Glu Leu Leu Met
 5                   10                  15

AAA TAC CAA TAC ATC TCC GAT TTC TTC ATT GCG ATT GCG TAT   283
Lys Tyr Gln Tyr Ile Ser Asp Phe Phe Ile Ala Ile Ala Tyr
     20                  25                  30

TTT TCG ATT CCT CTT GAG TTG ATT TAC TTT GTG AAG AAA TCA   325
Phe Ser Ile Pro Leu Glu Leu Ile Tyr Phe Val Lys Lys Ser
         35                  40                  45

GCC GTG TTT CCG TAT AGA TGG GTA CTT GTT CAG TTT GGT GCT   367
Ala Val Phe Pro Tyr Arg Trp Val Leu Val Gln Phe Gly Ala
             50                  55                  60

TTT TTC GTT CTT TGT GGA GCA ACT CAT CTT ATT AAC TTA TGG   409
Phe Phe Val Leu Cys Gly Ala Thr His Leu Ile Asn Leu Trp
                 65                  70

ACT TTC ACT ACG CAT TCG AGA ACC GTG GCG CTT GTG ATG ACT   451
Thr Phe Thr Thr His Ser Arg Thr Val Ala Leu Val Met Thr
 75                  80                  85

ACC GCG AAG GTG TTA ACC GCT GTT GTC TCG TGT GCT ACT GCG   493
Thr Ala Lys Val Leu Thr Ala Val Val Ser Cys Ala Thr Ala
     90                  95                 100

TTG ATG CTT GTT CAT ATT ATT CCT GAT CTT TTG AGT GTT AAG   535
Leu Met Leu Val His Ile Ile Pro Asp Leu Leu Ser Val Lys
        105                 110                 115

ACT CGG GAG CTT TTC TTG AAA AAT AAA GCT GCT GAG CTC GAT   577
Thr Arg Glu Leu Phe Leu Lys Asn Lys Ala Ala Glu Leu Asp
            120                 125                 130

AGA GAA ATG GGA TTG ATT CGA ACT CAG GAA GAA ACC GGA AGG   619
Arg Glu Met Gly Leu Ile Arg Thr Gln Glu Glu Thr Gly Arg
                135                 140

CAT GTG AGA ATG TTG ACT CAT GAG ATT AGA AGC ACT TTA GAT   661
His Val Arg Met Leu Thr His Glu Ile Arg Ser Thr Leu Asp
145                 150                 155

AGA CAT ACT ATT TTA AAG ACT ACA CTT GTT GAG CTT GGT AGG   703
Arg His Thr Ile Leu Lys Thr Thr Leu Val Glu Leu Gly Arg
    160                 165                 170

ACA TTA GCT TTG GAG GAG TGT GCA TTG TGG ATG CCT ACT AGA   745
Thr Leu Ala Leu Glu Glu Cys Ala Leu Trp Met Pro Thr Arg
        175                 180                 185
```

FIG. 5A

```
ACT GGG TTA GAG CTA CAG CTT TCT TAT ACA CTT CGT CAT CAA      787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT      829
His Pro Val Glu Tyr Thr Val Pro Ile Gln Leu Pro Val Ile
                205                 210

AAC CAA GTG TTT GGT ACT AGT AGG GCT GTA AAA ATA TCT CCT      871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT      913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC      955
Met Leu Gly Glu Val Val Ala Val Arg Val Pro Leu Leu His
        245                 250                 255

CTT TCT AAT TTT CAG ATT AAT GAC TGG CCT GAG CTT TCA ACA      997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT     1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC     1081
Ala Arg Gln Trp His Val His Glu Leu Glu Leu Val Glu Val
285                 290                 295

GTC GCT GAT CAG GTG GCT GTA GCT CTC TCA CAT GCT GCG ATC     1123
Val Ala Asp Gln Val Ala Val Ala Leu Ser His Ala Ala Ile
    300                 305                 310

CTA GAA GAG TCG ATG CGA GCT AGG GAC CTT CTC ATG GAG CAG     1165
Leu Glu Glu Ser Met Arg Ala Arg Asp Leu Leu Met Glu Gln
        315                 320                 325

AAT GTT GCT CTT GAT CTA GCT AGA CGA GAA GCA GAA ACA GCA     1207
Asn Val Ala Leu Asp Leu Ala Arg Arg Glu Ala Glu Thr Ala
            330                 335                 340

ATC CGT GCC CGC AAT GAT TTC CTA GCG GTT ATG AAC CAT GAA     1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA     1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG     1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG     1375
Glu Thr Ile Leu Lys Ser Ser Asn Leu Leu Ala Thr Leu Met
        385                 390                 395
```

*FIG. 5B*

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA    1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
        455                 460                 465

ATA GTT GGT AAT GCT GTG AAA TTC TCC AAA CAA GGT AGT ATC    1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
            540                 545                 550

TCC AAG AGG TTT GTG AAT CTG ATG GAG GGT AAC ATT TGG ATT    1879
Ser Lys Arg Phe Val Asn Leu Met Glu Gly Asn Ile Trp Ile
                555                 560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565                 570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
        595                 600                 605
```

FIG. 5C

```
TTC ACT GGA CTT AAG GTT CTT GTC ATG GAT GAG AAC GGG GTA    2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC    2089
Ser Arg Met Val Thr Lys Gly Leu Leu Val His Leu Gly Cys
                625                 630

GAA GTG ACC ACG GTG AGT TCA AAC GAG GAG TGT CTC CGA GTT    2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG    2173
Val Ser His Glu His Lys Val Val Phe Met Asp Val Cys Met
    650                 655                 660

CCC GGG GTC GAA AAC TAC CAA ATC GCT CTC CGT ATT CAC GAG    2215
Pro Gly Val Glu Asn Tyr Gln Ile Ala Leu Arg Ile His Glu
        665                 670                 675

AAA TTC ACA AAA CAA CGC CAC CAA CGG CCA CTA CTT GTG GCA    2257
Lys Phe Thr Lys Gln Arg His Gln Arg Pro Leu Leu Val Ala
            680                 685                 690

CTC AGT GGT AAC ACT GAC AAA TCC ACA AAA GAG AAA TGC ATG    2299
Leu Ser Gly Asn Thr Asp Lys Ser Thr Lys Glu Lys Cys Met
                695                 700

AGC TTT GGT CTA GAC GGT GTG TTG CTC AAA CCC GTA TCA CTA    2341
Ser Phe Gly Leu Asp Gly Val Leu Leu Lys Pro Val Ser Leu
705                 710                 715

GAC AAC ATA AGA GAT GTT CTG TCT GAT CTT CTC GAG CCC CGG    2383
Asp Asn Ile Arg Asp Val Leu Ser Asp Leu Leu Glu Pro Arg
    720                 725                 730

GTA CTG TAC GAG GGC ATG TAAAGGCGAT GGATGCCCCA              2421
Val Leu Tyr Glu Gly Met
        735

TGCCCCAGAG GAGTAATTCC GCTCCCGCCT TCTTCTCCCG TAAAACATCG     2471

GAAGCTGATG TTCTCTGGTT TAATTGTGTA CATATCAGAG ATTGTCGGAG     2521

CGTTTTGGAT GATATCTTAA AACAGAAAGG GAATAACAAA ATAGAAACTC     2571

TAAACCGGTA TGTGTCCGTG GCGATTTCGG TTATAGAGGA ACAAGATGGT     2621

GGTGGTATAA TCATACCATT TCAGATTACA TGTTTGACTA ATGTTGTATC     2671

CTTATATATG TAGTTACATT CTTATAAGAA TTTGGATCGA GTTATGGATG     2721

CTTGTTGCGT GCATGTATGA CATTGATGCA GTATTATGGC GTCAGCTTTG     2771

CGCCGCTTAG TAGAAC                                          2787
```

FIG. 5D

```
AGTAAGAACG AAGAAGAAGT GTTAAACCCA ACCAATTTTG ACTTGAAAAA          50

AAGCTTCAAC GCTCCCCTTT TCTCCTTCTC CGTCGCTCTC CGCCGCGTCC         100

CAAATCCCCA ATTCCTCCTC TTCTCCGATC AATTCTTCCC AAGTGTGTGT         150

ATGTGTGAGA GAGGAACTAT AGTGTAAAAA ATTCATA ATG GAA GTC TGC      199
                                        Met Glu Val Cys
                                         1

AAT TGT ATT GAA CCG CAA TGG CCA GCG GAT GAA TTG TTA ATG        241
Asn Cys Ile Glu Pro Gln Trp Pro Ala Asp Glu Leu Leu Met
 5                  10                  15

AAA TAC CAA TAC ATC TCC GAT TTC TTC ATT GCG ATT GCG TAT        283
Lys Tyr Gln Tyr Ile Ser Asp Phe Phe Ile Ala Ile Ala Tyr
     20                  25                  30

TTT TCG ATT CCT CTT GAG TTG ATT TAC TTT GTG AAG AAA TCA        325
Phe Ser Ile Pro Leu Glu Leu Ile Tyr Phe Val Lys Lys Ser
         35                  40                  45

GCC GTG TTT CCG TAT AGA TGG GTA CTT GTT CAG TTT GGT GCT        367
Ala Val Phe Pro Tyr Arg Trp Val Leu Val Gln Phe Gly Ala
             50                  55                  60

TTT ATC GTT CTT TAT GGA GCA ACT CAT CTT ATT AAC TTA TGG        409
Phe Ile Val Leu Tyr Gly Ala Thr His Leu Ile Asn Leu Trp
                 65                  70

ACT TTC ACT ACG CAT TCG AGA ACC GTG GCG CTT GTG ATG ACT        451
Thr Phe Thr Thr His Ser Arg Thr Val Ala Leu Val Met Thr
75                  80                  85

ACC GCG AAG GTG TTA ACC GCT GTT GTC TCG TGT GCT ACT GCG        493
Thr Ala Lys Val Leu Thr Ala Val Val Ser Cys Ala Thr Ala
     90                  95                  100

TTG ATG CTT GTT CAT ATT ATT CCT GAT CTT TTG AGT GTT AAG        535
Leu Met Leu Val His Ile Ile Pro Asp Leu Leu Ser Val Lys
         105                 110                 115

ACT CGG GAG CTT TTC TTG AAA AAT AAA GCT GCT GAG CTC GAT        577
Thr Arg Glu Leu Phe Leu Lys Asn Lys Ala Ala Glu Leu Asp
             120                 125                 130

AGA GAA ATG GGA TTG ATT CGA ACT CAG GAA GAA ACC GGA AGG        619
Arg Glu Met Gly Leu Ile Arg Thr Gln Glu Glu Thr Gly Arg
                 135                 140

CAT GTG AGA ATG TTG ACT CAT GAG ATT AGA AGC ACT TTA GAT        661
His Val Arg Met Leu Thr His Glu Ile Arg Ser Thr Leu Asp
145                 150                 155

AGA CAT ACT ATT TTA AAG ACT ACA CTT GTT GAG CTT GGT AGG        703
Arg His Thr Ile Leu Lys Thr Thr Leu Val Glu Leu Gly Arg
    160                 165                 170

ACA TTA GCT TTG GAG GAG TGT GCA TTG TGG ATG CCT ACT AGA        745
Thr Leu Ala Leu Glu Glu Cys Ala Leu Trp Met Pro Thr Arg
        175                 180                 185
```

FIG. 6A

ACT GGG TTA GAG CTA CAG CTT TCT TAT ACA CTT CGT CAT CAA 787
Thr Gly Leu Glu Leu Gln Leu Ser Tyr Thr Leu Arg His Gln
190 195 200

CAT CCC GTG GAG TAT ACG GTT CCT ATT CAA TTA CCG GTG ATT 829
His Pro Val Glu Tyr Thr Val Pro Ile Gln Leu Pro Val Ile
205 210

AAC CAA GTG TTT GGT ACT AGT AGG GCT GTA AAA ATA TCT CCT 871
Asn Gln Val Phe Gly Thr Ser Arg Ala Val Lys Ile Ser Pro
215 220 225

AAT TCT CCT GTG GCT AGG TTG AGA CCT GTT TCT GGG AAA TAT 913
Asn Ser Pro Val Ala Arg Leu Arg Pro Val Ser Gly Lys Tyr
230 235 240

ATG CTA GGG GAG GTG GTC GCT GTG AGG GTT CCG CTT CTC CAC 955
Met Leu Gly Glu Val Val Ala Val Arg Val Pro Leu Leu His
245 250 255

CTT TCT AAT TTT CAG ATT AAT GAC TGG CCT GAG CTT TCA ACA 997
Leu Ser Asn Phe Gln Ile Asn Asp Trp Pro Glu Leu Ser Thr
260 265 270

AAG AGA TAT GCT TTG ATG GTT TTG ATG CTT CCT TCA GAT AGT 1039
Lys Arg Tyr Ala Leu Met Val Leu Met Leu Pro Ser Asp Ser
275 280

GCA AGG CAA TGG CAT GTC CAT GAG TTG GAA CTC GTT GAA GTC 1081
Ala Arg Gln Trp His Val His Glu Leu Glu Leu Val Glu Val
285 290 295

GTC GCT GAT CAG GTG GCT GTA GCT CTC TCA CAT GCT GCG ATC 1123
Val Ala Asp Gln Val Ala Val Ala Leu Ser His Ala Ala Ile
300 305 310

CTA GAA GAG TCG ATG CGA GCT AGG GAC CTT CTC ATG GAG CAG 1165
Leu Glu Glu Ser Met Arg Ala Arg Asp Leu Leu Met Glu Gln
315 320 325

AAT GTT GCT CTT GAT CTA GCT AGA CGA GAA GCA GAA ACA GCA 1207
Asn Val Ala Leu Asp Leu Ala Arg Arg Glu Ala Glu Thr Ala
330 335 340

ATC CGT GCC CGC AAT GAT TTC CTA GCG GTT ATG AAC CAT GAA 1249
Ile Arg Ala Arg Asn Asp Phe Leu Ala Val Met Asn His Glu
345 350

ATG CGA ACA CCG ATG CAT GCG ATT ATT GCA CTC TCT TCC TTA 1291
Met Arg Thr Pro Met His Ala Ile Ile Ala Leu Ser Ser Leu
355 360 365

CTC CAA GAA ACG GAA CTA ACC CCT GAA CAA AGA CTG ATG GTG 1333
Leu Gln Glu Thr Glu Leu Thr Pro Glu Gln Arg Leu Met Val
370 375 380

GAA ACA ATA CTT AAA AGT AGT AAC CTT TTG GCA ACT TTG ATG 1375
Glu Thr Ile Leu Lys Ser Ser Asn Leu Leu Ala Thr Leu Met
385 390 395

*FIG. 6B*

```
AAT GAT GTC TTA GAT CTT TCA AGG TTA GAA GAT GGA AGT CTT   1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA   1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA   1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT   1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT   1585
Val Val Gly Asp Glu Lys Arg Leu Met Gln Ile Ile Leu Asn
        455                 460                 465

ATA GTT GGT AAT GCT GTG AAA TTC TCC AAA CAA GGT AGT ATC   1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT   1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA   1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC   1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA   1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC   1837
Ala Thr Arg Ser Ser Gly Gly Ser Gly Leu Gly Leu Ala Ile
            540                 545                 550

TCC AAG AGG TTT GTG AAT CTG ATG GAG GGT AAC ATT TGG ATT   1879
Ser Lys Arg Phe Val Asn Leu Met Glu Gly Asn Ile Trp Ile
                555                 560

GAG AGC GAT GGT CTT GGA AAA GGA TGC ACG GCT ATC TTT GAT   1921
Glu Ser Asp Gly Leu Gly Lys Gly Cys Thr Ala Ile Phe Asp
565                 570                 575

GTT AAA CTT GGG ATC TCA GAA CGT TCA AAC GAA TCT AAA CAG   1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT   2005
Ser Gly Ile Pro Lys Val Pro Ala Ile Pro Arg His Ser Asn
        595                 600                 605
```

*FIG. 6C*

```
TTC ACT GGA CTT AAG GTT CTT GTC ATG GAT GAG AAC GGG GTA     2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC     2089
Ser Arg Met Val Thr Lys Gly Leu Leu Val His Leu Gly Cys
                625                 630

GAA GTG ACC ACG GTG AGT TCA AAC GAG GAG TGT CTC CGA GTT     2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG     2173
Val Ser His Glu His Lys Val Val Phe Met Asp Val Cys Met
    650                 655                 660

CCC GGG GTC GAA AAC TAC CAA ATC GCT CTC CGT ATT CAC GAG     2215
Pro Gly Val Glu Asn Tyr Gln Ile Ala Leu Arg Ile His Glu
        665                 670                 675

AAA TTC ACA AAA CAA CGC CAC CAA CGG CCA CTA CTT GTG GCA     2257
Lys Phe Thr Lys Gln Arg His Gln Arg Pro Leu Leu Val Ala
            680                 685                 690

CTC AGT GGT AAC ACT GAC AAA TCC ACA AAA GAG AAA TGC ATG     2299
Leu Ser Gly Asn Thr Asp Lys Ser Thr Lys Glu Lys Cys Met
                695                 700

AGC TTT GGT CTA GAC GGT GTG TTG CTC AAA CCC GTA TCA CTA     2341
Ser Phe Gly Leu Asp Gly Val Leu Leu Lys Pro Val Ser Leu
705                 710                 715

GAC AAC ATA AGA GAT GTT CTG TCT GAT CTT CTC GAG CCC CGG     2383
Asp Asn Ile Arg Asp Val Leu Ser Asp Leu Leu Glu Pro Arg
    720                 725                 730

GTA CTG TAC GAG GGC ATG TAAAGGCGAT GGATGCCCCA TGCCCCAGAG   2431
Val Leu Tyr Glu Gly Met
        735

GAGTAATTCC GCTCCCGCCT TCTTCTCCCG TAAAACATCG GAAGCTGATG     2481

TTCTCTGGTT TAATTGTGTA CATATCAGAG ATTGTCGGAG CGTTTTGGAT     2531

GATATCTTAA AACAGAAAGG GAATAACAAA ATAGAAACTC TAAACCGGTA     2581

TGTGTCCGTG GCGATTTCGG TTATAGAGGA ACAAGATGGT GGTGGTATAA     2631

TCATACCATT TCAGATTACA TGTTTGACTA ATGTTGTATC CTTATATATG     2681

TAGTTACATT CTTATAAGAA TTTGGATCGA GTTATGGATG CTTGTTGCGT     2731

GCATGTATGA CATTGATGCA GTATTATGGC GTCAGCTTTG CGCCGCTTAG     2781

TAGAAC                                                     2787
```

FIG. 6D

```
AGTAAGAACG AAGAAGAAGT GTTAAACCCA ACCAATTTTG ACTTGAAAAA        50

AAGCTTCAAC GCTCCCCTTT TCTCCTTCTC CGTCGCTCTC CGCCGCGTCC       100

CAAATCCCCA ATTCCTCCTC TTCTCCGATC AATTCTTCCC AAGTGTGTGT       150

ATGTGTGAGA GAGGAACTAT AGTGTAAAAA ATTCATA ATG GAA GTC TGC     199
                                         Met Glu Val Cys
                                          1

AAT TGT ATT GAA CCG CAA TGG CCA GCG GAT GAA TTG TTA ATG      241
Asn Cys Ile Glu Pro Gln Trp Pro Ala Asp Glu Leu Leu Met
  5                  10                  15

AAA TAC CAA TAC ATC TCC GAT TTC TTC ATT GCG ATT GCG TAT      283
Lys Tyr Gln Tyr Ile Ser Asp Phe Phe Ile Ala Ile Ala Tyr
     20                  25                  30

TTT TCG ATT CCT CTT GAG TTG ATT TAC TTT GTG AAG AAA TCA      325
Phe Ser Ile Pro Leu Glu Leu Ile Tyr Phe Val Lys Lys Ser
         35                  40                  45

GCC GTG TTT CCG TAT AGA TGG GTA CTT GTT CAG TTT GGT GCT      367
Ala Val Phe Pro Tyr Arg Trp Val Leu Val Gln Phe Gly Ala
             50                  55                  60

TTT ATC GTT CTT TGT GGA GCA ACT CAT CTT ATT AAC TTA TGG      409
Phe Ile Val Leu Cys Gly Ala Thr His Leu Ile Asn Leu Trp
                 65                  70

ACT TTC ACT ACG CAT TCG AGA ACC GTG GCG CTT GTG ATG ACT      451
Thr Phe Thr Thr His Ser Arg Thr Val Ala Leu Val Met Thr
 75                  80                  85

ACC GCG AAG GTG TTA ACC GCT GTT GTC TCG TGT GCT ACT ACG      493
Thr Ala Lys Val Leu Thr Ala Val Val Ser Cys Ala Thr Thr
     90                  95                 100

TTG ATG CTT GTT CAT ATT ATT CCT GAT CTT TTG AGT GTT AAG      535
Leu Met Leu Val His Ile Ile Pro Asp Leu Leu Ser Val Lys
        105                 110                 115

ACT CGG GAG CTT TTC TTG AAA AAT AAA GCT GCT GAG CTC GAT      577
Thr Arg Glu Leu Phe Leu Lys Asn Lys Ala Ala Glu Leu Asp
            120                 125                 130

AGA GAA ATG GGA TTG ATT CGA ACT CAG GAA GAA ACC GGA AGG      619
Arg Glu Met Gly Leu Ile Arg Thr Gln Glu Glu Thr Gly Arg
                135                 140

CAT GTG AGA ATG TTG ACT CAT GAG ATT AGA AGC ACT TTA GAT      661
His Val Arg Met Leu Thr His Glu Ile Arg Ser Thr Leu Asp
145                 150                 155

AGA CAT ACT ATT TTA AAG ACT ACA CTT GTT GAG CTT GGT AGG      703
Arg His Thr Ile Leu Lys Thr Thr Leu Val Glu Leu Gly Arg
    160                 165                 170

ACA TTA GCT TTG GAG GAG TGT GCA TTG TGG ATG CCT ACT AGA      745
Thr Leu Ala Leu Glu Glu Cys Ala Leu Trp Met Pro Thr Arg
        175                 180                 185
```

*FIG. 7A*

```
ACT GGG TTA GAG CTA CAG CTT TCT TAT ACA CTT CGT CAT CAA      787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT      829
His Pro Val Glu Tyr Thr Val Pro Ile Gln Leu Pro Val Ile
                205                 210

AAC CAA GTG TTT GGT ACT AGT AGG GCT GTA AAA ATA TCT CCT      871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT      913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC      955
Met Leu Gly Glu Val Val Ala Val Arg Val Pro Leu Leu His
        245                 250                 255

CTT TCT AAT TTT CAG ATT AAT GAC TGG CCT GAG CTT TCA ACA      997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT     1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC     1081
Ala Arg Gln Trp His Val His Glu Leu Glu Leu Val Glu Val
285                 290                 295

GTC GCT GAT CAG GTG GCT GTA GCT CTC TCA CAT GCT GCG ATC     1123
Val Ala Asp Gln Val Ala Val Ala Leu Ser His Ala Ala Ile
    300                 305                 310

CTA GAA GAG TCG ATG CGA GCT AGG GAC CTT CTC ATG GAG CAG     1165
Leu Glu Glu Ser Met Arg Ala Arg Asp Leu Leu Met Glu Gln
        315                 320                 325

AAT GTT GCT CTT GAT CTA GCT AGA CGA GAA GCA GAA ACA GCA     1207
Asn Val Ala Leu Asp Leu Ala Arg Arg Glu Ala Glu Thr Ala
            330                 335                 340

ATC CGT GCC CGC AAT GAT TTC CTA GCG GTT ATG AAC CAT GAA     1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA     1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG     1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG     1375
Glu Thr Ile Leu Lys Ser Ser Asn Leu Leu Ala Thr Leu Met
        385                 390                 395
```

*FIG. 7B*

```
AAT GAT GTC TTA GAT CTT TCA AGG TTA GAA GAT GGA AGT CTT     1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA     1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA     1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT     1543
Leu Pro Ile Thr Leu Asn Leu Ala Pro Asp Leu Pro Glu Phe
    440                     445                 450

GTT GTT GGG GAT GAG AAA CGG CTA ATG CAG ATA ATA TTA AAT     1585
Val Val Gly Asp Glu Lys Arg Leu Met Gln Ile Ile Leu Asn
        455                 460                 465

ATA GTT GGT AAT GCT GTG AAA TTC TCC AAA CAA GGT AGT ATC     1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT     1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA     1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC     1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA     1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC     1837
Ala Thr Arg Ser Ser Gly Gly Ser Gly Leu Gly Leu Ala Ile
            540                 545                 550

TCC AAG AGG TTT GTG AAT CTG ATG GAG GGT AAC ATT TGG ATT     1879
Ser Lys Arg Phe Val Asn Leu Met Glu Gly Asn Ile Trp Ile
                555                 560

GAG AGC GAT GGT CTT GGA AAA GGA TGC ACG GCT ATC TTT GAT     1921
Glu Ser Asp Gly Leu Gly Lys Gly Cys Thr Ala Ile Phe Asp
565                 570                 575

GTT AAA CTT GGG ATC TCA GAA CGT TCA AAC GAA TCT AAA CAG     1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT     2005
Ser Gly Ile Pro Lys Val Pro Ala Ile Pro Arg His Ser Asn
        595                 600                 605
```

*FIG. 7C*

```
TTC ACT GGA CTT AAG GTT CTT GTC ATG GAT GAG AAC GGG GTA   2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC   2089
Ser Arg Met Val Thr Lys Gly Leu Leu Val His Leu Gly Cys
                625                 630

GAA GTG ACC ACG GTG AGT TCA AAC GAG GAG TGT CTC CGA GTT   2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG   2173
Val Ser His Glu His Lys Val Val Phe Met Asp Val Cys Met
    650                 655                 660

CCC GGG GTC GAA AAC TAC CAA ATC GCT CTC CGT ATT CAC GAG   2215
Pro Gly Val Glu Asn Tyr Gln Ile Ala Leu Arg Ile His Glu
        665                 670                 675

AAA TTC ACA AAA CAA CGC CAC CAA CGG CCA CTA CTT GTG GCA   2257
Lys Phe Thr Lys Gln Arg His Gln Arg Pro Leu Leu Val Ala
            680                 685                 690

CTC AGT GGT AAC ACT GAC AAA TCC ACA AAA GAG AAA TGC ATG   2299
Leu Ser Gly Asn Thr Asp Lys Ser Thr Lys Glu Lys Cys Met
                695                 700

AGC TTT GGT CTA GAC GGT GTG TTG CTC AAA CCC GTA TCA CTA   2341
Ser Phe Gly Leu Asp Gly Val Leu Leu Lys Pro Val Ser Leu
705                 710                 715

GAC AAC ATA AGA GAT GTT CTG TCT GAT CTT CTC GAG CCC CGG   2383
Asp Asn Ile Arg Asp Val Leu Ser Asp Leu Leu Glu Pro Arg
    720                 725                 730

GTA CTG TAC GAG GGC ATG TAAAGGCGAT GGATGCCCCA TGCCCCAGAG   2431
Val Leu Tyr Glu Gly Met
        735

GAGTAATTCC GCTCCCGCCT TCTTCTCCCG TAAAACATCG GAAGCTGATG   2481

TTCTCTGGTT TAATTGTGTA CATATCAGAG ATTGTCGGAG CGTTTTGGAT   2531

GATATCTTAA AACAGAAAGG GAATAACAAA ATAGAAACTC TAAACCGGTA   2581

TGTGTCCGTG GCGATTTCGG TTATAGAGGA ACAAGATGGT GGTGGTATAA   2631

TCATACCATT TCAGATTACA TGTTTGACTA ATGTTGTATC CTTATATATG   2681

TAGTTACATT CTTATAAGAA TTTGGATCGA GTTATGGATG CTTGTTGCGT   2731

GCATGTATGA CATTGATGCA GTATTATGGC GTCAGCTTTG CGCCGCTTAG   2781

TAGAAC                                                    2787
```

```
                                                *
ETR1  QNVALDLARREAETAIRARNDFLAV MNHEMRTPM HAIIALSSLLQETELTPEQRL  380
BARA  QNVELDLAKKRAQEAARIKSEFLAN MSHELRTPL NGVIGFTRLTLKTELTPTQRD  329
LEMA  QNIELDLARKEALEASRIKSEFLAN MSHEIRTPL NGILGFTHLLQKSELTPRQFD  311
RPFC          RAVREARHANQAKSRFLAN MSHEFRTPL NGLSGMTEVLATTRLDAEQKE  176

ETR1  MVETILKSSNLLATLMNDVLDLSRLEDGSLQLELGTFNLHTLFREVLNLIKPIAVV  436
BARA  HLNTIERSANNLLAIINDVLDFSKLEAGKLILESIPFPLRSTLDEVVTLLAHSSHD  385
LEMA  YLGTIEKSADNLLSIINEILDFSKIEAGKLVLDNIPFNLRDLLQDTLTILAPAAHA  367
RPFC  CLNTIQASARSLLSLVEEVLDISAIEAGKIRIDRRDFSLREMIGSVNLILQPQARG  232

ETR1  KKLPITLNLAPDLPEFVVGDEKR LMQIILNIVGNA VKFSKQGSI (26) LRVK  510
BARA  KGLELTLNIKSDVPDNVIGDPLR LQQIITNLVGNA IKFTENGNI (15) IEVQ  448
LEMA  KQLELVSLVYRDTPLALSGDPLR LRQILTNLVSNA IKFTREGTI (15) LRIS  430
RPFC  RRLEYGTQVADDVPLLLKGDTAH LRQVLLNLVGNA VKFTEHGHV (16) LRFD  296

ETR1  VKDSGAGIN PQDIPK IFTKF AQTQSLATRSSG GSGLGL AISKRFVNLMEGNI  562
BARA  IRDTGIGIP ERDQSR LFQAF RQADASISRRHG GTGLGL VITQKLVNEMGGDI  500
LEMA  VQDTGIGLS SQDVRA LFQAF SQADNSLSRQPG GTGLGL VISKRLIEQMGGEI  482
RPFC  VEDTGIGVP MDMRPR LFEAF EQADVGLSRRYE GTGLGT TIAKGLVEAMGGSI  348
```

FIG. 9B

```
ETR1  LKVLVM DE NGVSRMVTKGLLVHLGCEVTTVSSNEECLRV   648
BVGS  LRVLVV DD HKPNLMLLRQQLDYLGQRVVAADSGEAALAL  1011
RCSC  MMILVV DD HPINRRLLADQLGSLGYQCKTANDGVDALNV   847
LEMA  PRVLCV DD NPANLLLVQTLLEDMGAEVVAVEGGYAAVNA   695

                  *
ETR1  VSHEH-KVVFM D VCMPGVENYQIALRIH (10) PLLVA   690
BVGS  WHEHAFDVVIT D CNMPGINGYELARRIR (12) CILFG  1056
RCSC  LSKNHIDIVLS D VNMPNMDGYRLTQRIR  (5) LPVIG   885
LEMA  VQQEAFDLVLM D VQMPGMDGRQATEAIR (10) LPIVA   738

ETR1  LSGNTDKSTKEKCMSFGLDGVLL K PVSLDNIRDVLSDLL   729
BVGS  FTASAQMDEAHACRAAGMDDCLF K PIGVDALRQRLNEAA  1095
RCSC  VTANALAEEKQRCLESGMDSCLS K PVTLDVIKQSLTLYA   924
LEMA  LTAHAMANEKRSLLQSGMDDYLT K PISERQLAQVVLKWT   777
```

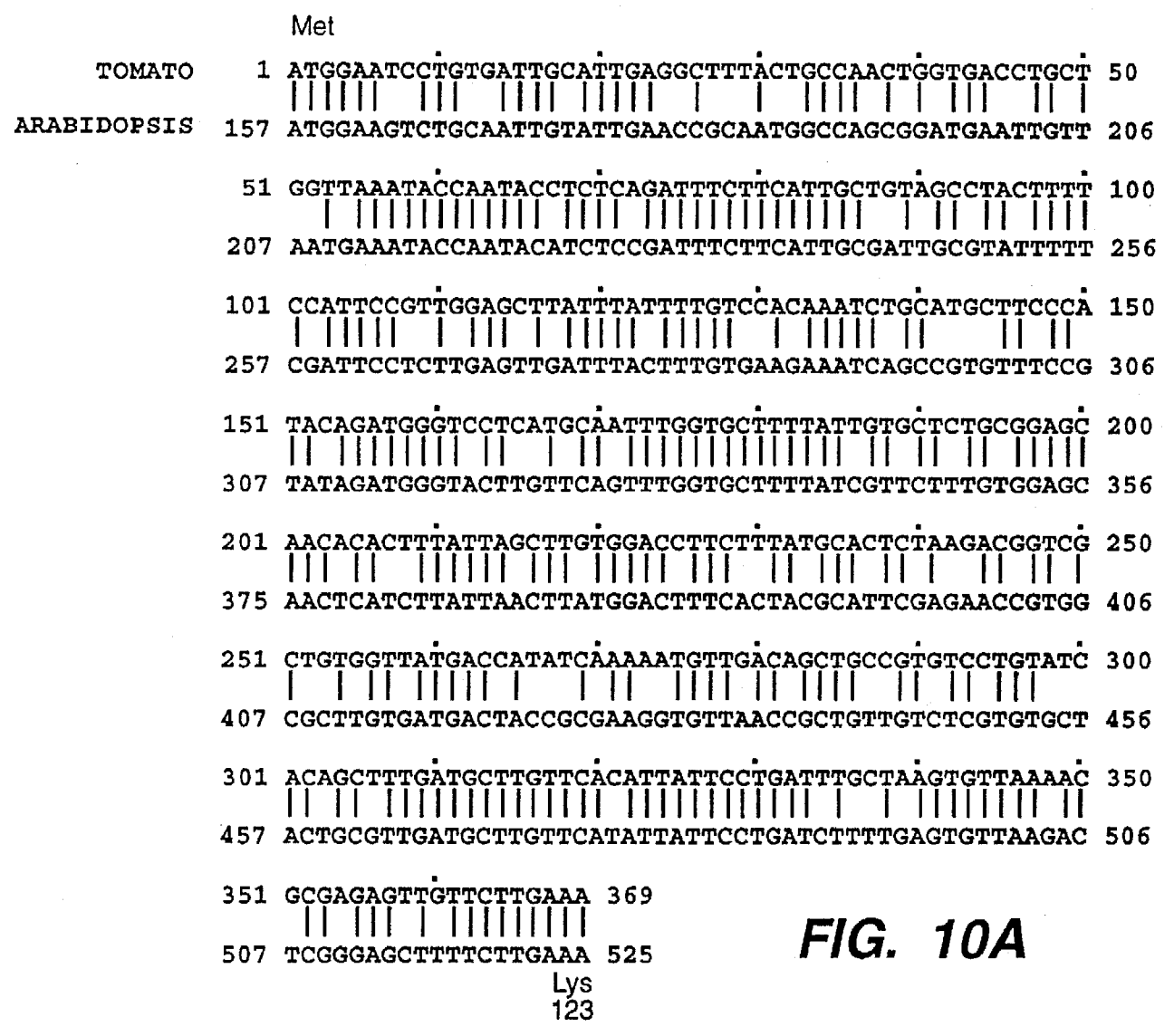

```
                       Met
TOMATO         1   ATGGAATCCTGTGATTGCATTGAGGCTTTACTGCCAACTGGTGACCTGCT  50
ARABIDOPSIS  157   ATGGAAGTCTGCAATTGTATTGAACCGCAATGGCCAGCGGATGAATTGTT  206

              51   GGTTAAATACCAATACCTCTCAGATTTCTTCATTGCTGTAGCCTACTTTT  100
             207   AATGAAATACCAATACATCTCCGATTTCTTCATTGCGATTGCGTATTTTT  256

             101   CCATTCCGTTGGAGCTTATTTATTTGTCCACAAATCTGCATGCTTCCCA  150
             257   CGATTCCTCTTGAGTTGATTTACTTTGTGAAGAAATCAGCCGTGTTTCCG  306

             151   TACAGATGGGTCCTCATGCAATTTGGTGCTTTTATTGTGCTCTGCGGAGC  200
             307   TATAGATGGGTACTTGTTCAGTTTGGTGCTTTTATCGTTCTTTGTGGAGC  356

             201   AACACACTTTATTAGCTTGTGGACCTTCTTTATGCACTCTAAGACGGTCG  250
             375   AACTCATCTTATTAACTTATGGACTTTCACTACGCATTCGAGAACCGTGG  406

             251   CTGTGGTTATGACCATATCAAAAATGTTGACAGCTGCCGTGTCCTGTATC  300
             407   CGCTTGTGATGACTACCGCGAAGGTGTTAACCGCTGTTGTCTCGTGTGCT  456

             301   ACAGCTTTGATGCTTGTTCACATTATTCCTGATTTGCTAAGTGTTAAAAC  350
             457   ACTGCGTTGATGCTTGTTCATATTATTCCTGATCTTTTGAGTGTTAAGAC  506

             351   GCGAGAGTTGTTCTTGAAA  369
             507   TCGGGAGCTTTTCTTGAAA  525
                                  Lys
                                  123
```

FIG. 10A

```
                    Ala
                    306
TOMATO         1    GCTCTTTCACATGCTGCAATTTTAGAAGATTCCATGCGAGCCCATGATCA  50
ARABIDOPSIS 1072    GCTCTCTCACATGCTGCGATCCTAGAAGAGTCGATGCGAGCTAGGGACCT  1121

              51    GCTCATGGAACAGAATATTGCTTTGGATGTAGCTCGACAAGAAGCAGAGA  100
            1122    TCTCATGGAGCAGAATGTTGCTCTTGATCTAGCTAGACGAGAAGCAGAAA  1171

             101    TGGCCATCCGTGCACGTAACGACTTCCTTGCTGTGATGAACCATGAAATG  150
            1172    CAGCAATCCGTGCCCGCAATGATTTCCTAGCGGTTATGAACCATGAAATG  1221

             151    AGAACGCCCATGCATGCAGTTATTGCTCTGTGCTCTCTGCTTTTAGAAAC  200
            1222    CGAACACCGATGCATGCGATTATTGCACTCTCTTCCTTACTCCAAGAAAC  1271

             201    AGACTTAACTCCAGAGCAGAGAGTTATGATTGAGACCATATTGAAGAGCA  250
            1272    GGAACTAACCCCTGAACAAAGACTGATGGTGGAAACAATACTTAAAAGTA  1321

             251    GCAATCTTCTTGCAACACTGATAAATGATGTTCTAGATCTTTCTAG  296
            1322    GTAACCTTTTGGCAACTTTGATGAATGATGTCTTAGATCTTTCAAG  1367
                                                                Ser
                                                                403
```

*FIG. 10B*

```
TOMATO       1 MESCDCIEALLPTGDLLVKYQYLSDFFIAVAYFSIPLELIYFVHKSACFP 50
ARABIDOPSIS  1 MEVCNCIEPQWPADELLMKYQYISDFFIAIAYFSIPLELIYFVKKSAVFP 50

            51 YRWVLMQFGAFIVLCGATHFISLWTFFMHSKTVAVVMTISKMLTAAVSCI 100
            51 YRWVLVQFGAFIVLCGATHLINLWTFTTHSRTVALVMTTAKVLTAVVSCA 100

           101 TALMLVHIIPDLLSVKTRELFLK 123
           101 TALMLVHIIPDLLSVKTRELFLK 123
```

*FIG. 11A*

```
ARABIDOPSIS 306 ALSHAAILEESMRARDLLMEQNVALDLARREAETAIRARNDFLAVMNHEM 355
TOMATO        1 ALSHAAILEDSMRAHDQLMEQNIALDVARQEAEMAIRARNDFLAVMNHEM 50

            356 RTPMHAIIALSSLLQETELTPEQRLMVETILKSSNLLATLMNDVLDLS 403
             51 RTPMHAVIALCSLLLETDLTPEQRVMIETILKSSNLLATLINDVLDLS 93
```

*FIG. 11B*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
( A ) LENGTH: 3879 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
AAAGATAGTA TTTGTTGATA AATATGGGGA TATTTATCCT ATATTATCTG TATTTTTCTT 60
ACCATTTTTA CTCTATTCCT TTATCTACAT TACGTCATTA CACTATCATA AGATATTTGA 120
ATGAACAAAT TCATGCACCC ACCAGCTATA TTACCCTTTT TTATTAAAAA AAAACATCTG 180
ATAATAATAA CAAAAAAATT AGAGAAATGA CGTCGAAAAA AAAAGTAAGA ACGAAGAAGA 240
AGTGTTAAAC CCAACCAATT TTGACTTGAA AAAAAGCTTC AACGCTCCCC TTTTCTCCTT 300
CTCCGTCGCT CTCCGCCGCG TCCCAAATCC CCAATTCCTC CTCTTCTCCG ATCAATTCTT 360
CCCAAGTAAG CTTCTTCTTC CTCGATTCTC TCCTCAGATT GTTTCGTGAC TTCTTTATAT 420
ATATTCTTCA CTTCCACAGT TTTCTTCTGT TGTTGTCGTC GATCTCAAAT CATAGAGATT 480
GATTAACCTA ATTGGTCTTT ATCTAGTGTA ATGCATCGTT ATTAGGAACT TTAAATTAAG 540
ATTTAATCGT TAATTTCATG ATTCGGATTC GAATTTTACT GTTCTCGAGA CTGAAATATG 600
CAACCTATTT TTTCGTAATC GTTGTGATCG AATTCGATTC TTCAGAATTT ATAGCAATTT 660
TGATGCTCAT GATCTGTCTA CGCTACGTTC TCGTCGTAAA TCGAAGTTGA TAATGCTATG 720
TGTTTGTTAC ACAGGTGTGT GTATGTGTGA GAGAGGAACT ATAGTGTAAA AAATTCATAA 780
TGGAAGTCTG CAATTGTATT GAACCGCAAT GGCCAGCGGA TGAATTGTTA ATGAAATACC 840
AATACATCTC CGATTTCTTC ATTGCGATTG CGTATTTTTC GATTCCTCTT GAGTTGATTT 900
ACTTTGTGAA GAAATCAGCC GTGTTTCCGT ATAGATGGGT ACTTGTTCAG TTTGGTGCTT 960
TTATCGTTCT TTGTGGAGCA ACTCATCTTA TTAACTTATG GACTTTCACT ACGCATTCGA 1020
GAACCGTGGC GCTTGTGATG ACTACCGCGA AGGTGTTAAC CGCTGTTGTC TCGTGTGCTA 1080
CTGCGTTGAT GCTTGTTCAT ATTATTCCTG ATCTTTTGAG TGTTAAGACT CGGGAGCTTT 1140
TCTTGAAAAA TAAAGCTGCT GAGCTCGATA GAGAAATGGG ATTGATTCGA ACTCAGGAAG 1200
AAACCGGAAG GCATGTGAGA ATGTTGACTC ATGAGATTAG AAGCACTTTA GATAGACATA 1260
CTATTTTAAA GACTACACTT GTTGAGCTTG GTAGGACATT AGCTTTGGAG GAGTGTGCAT 1320
TGTGGATGCC TACTAGAACT GGGTTAGAGC TACAGCTTTC TTATACACTT CGTCATCAAC 1380
ATCCCGTGGA GTATACGGTT CCTATTCAAT TACCGGTGAT TAACCAAGTG TTTGGTACTA 1440
GTAGGGCTGT AAAAATATCT CCTAATTCTC CTGTGGCTAG GTTGAGACCT GTTTCTGGGA 1500
AATATATGCT AGGGGAGGTG GTCGCTGTGA GGGTTCCGCT TCTCCACCTT TCTAATTTTC 1560
AGATTAATGA CTGGCCTGAG CTTTCAACAA AGAGATATGC TTTGATGGTT TTGATGCTTC 1620
CTTCAGATAG TGCAAGGCAA TGGCATGTCC ATGAGTTGGA ACTCGTTGAA GTCGTCGCTG 1680
ATCAGGTTTT ACATTGCTGA GAATTTCTCT TCTTTGCTAT GTTCATGATC TTGTCTATAA 1740
```

-continued

```
CTTTTCTTCT CTTATTATAG GTGGCTGTAG CTCTCTCACA TGCTGCGATC CTAGAAGAGT 1800
CGATGCGAGC TAGGGACCTT CTCATGGAGC AGAATGTTGC TCTTGATCTA GCTAGACGAG 1860
AAGCAGAAAC AGCAATCCGT GCCCGCAATG ATTTCCTAGC GGTTATGAAC CATGAAATGC 1920
GAACACCGAT GCATGCGATT ATTGCACTCT CTTCCTTACT CCAAGAAACG GAACTAACCC 1980
CTGAACAAAG ACTGATGGTG GAAACAATAC TTAAAAGTAG TAACCTTTTG GCAACTTTGA 2040
TGAATGATGT CTTAGATCTT TCAAGGTTAG AAGATGGAAG TCTTCAACTT GAACTTGGGA 2100
CATTCAATCT TCATACATTA TTTAGAGAGG TAACTTTTGA ACAGCTCTAT GTTTCATAAG 2160
TTTATACTAT TTGTGTACTT GATTGTCATA TTGAATCTTG TTGCAGGTCC TCAATCTGAT 2220
AAAGCCTATA GCGGTTGTTA AGAAATTACC CATCACACTA AATCTTGCAC CAGATTTGCC 2280
AGAATTTGTT GTTGGGGATG AGAAACGGCT AATGCAGATA ATATTAAATA TAGTTGGTAA 2340
TGCTGTGAAA TTCTCCAAAC AAGGTAGTAT CTCCGTAACC GCTCTTGTCA CCAAGTCAGA 2400
CACACGAGCT GCTGACTTTT TTGTCGTGCC AACTGGGAGT CATTTCTACT TGAGAGTGAA 2460
GGTTATTATC TTGTATCTTG GGATCTTATA CCATAGCTGA AAGTATTTCT TAGGTCTTAA 2520
TTTTGATGAT TATTCAAATA TAGGTAAAAG ACTCTGGAGC AGGAATAAAT CCTCAAGACA 2580
TTCCAAAGAT TTTCACTAAA TTTGCTCAAA CACAATCTTT AGCGACGAGA AGCTCGGGTG 2640
GTAGTGGGCT TGGCCTCGCC ATCTCCAAGA GGTTTGAGCC TTATTAAAAG ACGTTTTTTT 2700
CCAACTTTTT CTTGTCTTCT GTGTTGTTAA AAGTTTACTC ATAAGCGTTT AATATGACAA 2760
GGTTTGTGAA TCTGATGGAG GGTAACATTT GGATTGAGAG CGATGGTCTT GGAAAAGGAT 2820
GCACGGCTAT CTTTGATGTT AAACTTGGGA TCTCAGAACG TTCAAACGAA TCTAAACAGT 2880
CGGGCATACC GAAAGTTCCA GCCATTCCCC GACATTCAAA TTTCACTGGA CTTAAGGTTC 2940
TTGTCATGGA TGAGAACGGG TTAGTATAAG CTTCTCACCT TTCTCTTTGC AAAATCTCTC 3000
GCCTTACTTC TTGCAAATGC AGATATTGGC GTTTAGAAAA AACGCAAATT TAATCTTATG 3060
AGAAACCGAT GATTATTTTG GTTGCAGGGT AAGTAGAATG GTGACGAAGG GACTTCTTGT 3120
ACACCTTGGG TGCGAAGTGA CCACGGTGAG TTCAAACGAG GAGTGTCTCC GAGTTGTGTC 3180
CCATGAGCAC AAAGTGGTCT TCATGGACGT GTGCATGCCC GGGGTCGAAA ACTACCAAAT 3240
CGCTCTCCGT ATTCACGAGA AATTCACAAA ACAACGCCAC CAACGGCCAC TACTTGTGGC 3300
ACTCAGTGGT AACACTGACA AATCCACAAA AGAGAAATGC ATGAGCTTTG GTCTAGACGG 3360
TGTGTTGCTC AAACCCGTAT CACTAGACAA CATAAGAGAT GTTCTGTCTG ATCTTCTCGA 3420
GCCCCGGGTA CTGTACGAGG GCATGTAAAG GCGATGGATG CCCCATGCCC CAGAGGAGTA 3480
ATTCCGCTCC CGCCTTCTTC TCCCGTAAAA CATCGGAAGC TGATGTTCTC TGGTTTAATT 3540
GTGTACATAT CAGAGATTGT CGGAGCGTTT TGGATGATAT CTTAAAACAG AAAGGGAATA 3600
ACAAAATAGA AACTCTAAAC CGGTATGTGT CCGTGGCGAT TTCGGTTATA GAGGAACAAG 3660
ATGGTGGTGG TATAATCATA CCATTTCAGA TTACATGTTT GACTAATGTT GTATCCTTAT 3720
ATATGTAGTT ACATTCTTAT AAGAATTTGG ATCGAGTTAT GGATGCTTGT TGCGTGCATG 3780
TATGACATTG ATGCAGTATT ATGGCGTCAG CTTTGCGCCG CTTAGTAGAA CAACAACAAT 3840
GGCGTTACTT AGTTTCTCAA TCAACCCGAT CTCCAAAAC                       3879
```

( 2 ) INFORMATION FOR SEQ ID NO:2:

( i ) SEQUENCE CHARACTERISTICS:

( A ) LENGTH: 2787 base pairs ( B ) TYPE: nucleic acid ( C ) STRANDEDNESS: single (D) TOPOLOGY: linear (ii) MOLECULE TYPE: cDNA (ix) FEATURE:
(A) NAME/KEY: CDS
(B) LOCATION: 188..2401

(xi) SEQUENCE DESCRIPTION: SEQ ID NO:2:

```
AGTAAGAACG AAGAAGAAGT GTTAAACCCA ACCAATTTTG ACTTGAAAAA AAGCTTCAAC    60

GCTCCCCTTT TCTCCTTCTC CGTCGCTCTC CGCCGCGTCC CAAATCCCCA ATTCCTCCTC   120

TTCTCCGATC AATTCTTCCC AAGTGTGTGT ATGTGTGAGA GAGGAACTAT AGTGTAAAAA   180

ATTCATA ATG GAA GTC TGC AAT TGT ATT GAA CCG CAA TGG CCA GCG GAT     229
        Met Glu Val Cys Asn Cys Ile Glu Pro Gln Trp Pro Ala Asp
          1               5                  10

GAA TTG TTA ATG AAA TAC CAA TAC ATC TCC GAT TTC TTC ATT GCG ATT     277
Glu Leu Leu Met Lys Tyr Gln Tyr Ile Ser Asp Phe Phe Ile Ala Ile
 15                  20                  25                  30

GCG TAT TTT TCG ATT CCT CTT GAG TTG ATT TAC TTT GTG AAG AAA TCA     325
Ala Tyr Phe Ser Ile Pro Leu Glu Leu Ile Tyr Phe Val Lys Lys Ser
                 35                  40                  45

GCC GTG TTT CCG TAT AGA TGG GTA CTT GTT CAG TTT GGT GCT TTT ATC     373
Ala Val Phe Pro Tyr Arg Trp Val Leu Val Gln Phe Gly Ala Phe Ile
             50                  55                  60

GTT CTT TGT GGA GCA ACT CAT CTT ATT AAC TTA TGG ACT TTC ACT ACG     421
Val Leu Cys Gly Ala Thr His Leu Ile Asn Leu Trp Thr Phe Thr Thr
         65                  70                  75

CAT TCG AGA ACC GTG GCG CTT GTG ATG ACT ACC GCG AAG GTG TTA ACC     469
His Ser Arg Thr Val Ala Leu Val Met Thr Thr Ala Lys Val Leu Thr
     80                  85                  90

GCT GTT GTC TCG TGT GCT ACT GCG TTG ATG CTT GTT CAT ATT ATT CCT     517
Ala Val Val Ser Cys Ala Thr Ala Leu Met Leu Val His Ile Ile Pro
 95                 100                 105                 110

GAT CTT TTG AGT GTT AAG ACT CGG GAG CTT TTC TTG AAA AAT AAA GCT     565
Asp Leu Leu Ser Val Lys Thr Arg Glu Leu Phe Leu Lys Asn Lys Ala
                115                 120                 125

GCT GAG CTC GAT AGA GAA ATG GGA TTG ATT CGA ACT CAG GAA GAA ACC     613
Ala Glu Leu Asp Arg Glu Met Gly Leu Ile Arg Thr Gln Glu Glu Thr
            130                 135                 140

GGA AGG CAT GTG AGA ATG TTG ACT CAT GAG ATT AGA AGC ACT TTA GAT     661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA     709
Arg His Thr Ile Leu Lys Thr Thr Leu Val Glu Leu Gly Arg Thr Leu
    160                 165                 170

GCT TTG GAG GAG TGT GCA TTG TGG ATG CCT ACT AGA ACT GGG TTA GAG     757
Ala Leu Glu Glu Cys Ala Leu Trp Met Pro Thr Arg Thr Gly Leu Glu
175                 180                 185                 190

CTA CAG CTT TCT TAT ACA CTT CGT CAT CAA CAT CCC GTG GAG TAT ACG     805
Leu Gln Leu Ser Tyr Thr Leu Arg His Gln His Pro Val Glu Tyr Thr
                195                 200                 205

GTT CCT ATT CAA TTA CCG GTG ATT AAC CAA GTG TTT GGT ACT AGT AGG     853
Val Pro Ile Gln Leu Pro Val Ile Asn Gln Val Phe Gly Thr Ser Arg
            210                 215                 220

GCT GTA AAA ATA TCT CCT AAT TCT CCT GTG GCT AGG TTG AGA CCT GTT     901
Ala Val Lys Ile Ser Pro Asn Ser Pro Val Ala Arg Leu Arg Pro Val
        225                 230                 235

TCT GGG AAA TAT ATG CTA GGG GAG GTG GTC GCT GTG AGG GTT CCG CTT     949
Ser Gly Lys Tyr Met Leu Gly Glu Val Val Ala Val Arg Val Pro Leu
    240                 245                 250
```

-continued

```
CTC CAC CTT TCT AAT TTT CAG ATT AAT GAC TGG CCT GAG CTT TCA ACA       997
Leu His Leu Ser Asn Phe Gln Ile Asn Asp Trp Pro Glu Leu Ser Thr
255                 260                 265                 270

AAG AGA TAT GCT TTG ATG GTT TTG ATG CTT CCT TCA GAT AGT GCA AGG      1045
Lys Arg Tyr Ala Leu Met Val Leu Met Leu Pro Ser Asp Ser Ala Arg
                275                 280                 285

CAA TGG CAT GTC CAT GAG TTG GAA CTC GTT GAA GTC GTC GCT GAT CAG      1093
Gln Trp His Val His Glu Leu Glu Leu Val Glu Val Val Ala Asp Gln
            290                 295                 300

GTG GCT GTA GCT CTC TCA CAT GCT GCG ATC CTA GAA GAG TCG ATG CGA      1141
Val Ala Val Ala Leu Ser His Ala Ala Ile Leu Glu Glu Ser Met Arg
        305                 310                 315

GCT AGG GAC CTT CTC ATG GAG CAG AAT GTT GCT CTT GAT CTA GCT AGA      1189
Ala Arg Asp Leu Leu Met Glu Gln Asn Val Ala Leu Asp Leu Ala Arg
    320                 325                 330

CGA GAA GCA GAA ACA GCA ATC CGT GCC CGC AAT GAT TTC CTA GCG GTT      1237
Arg Glu Ala Glu Thr Ala Ile Arg Ala Arg Asn Asp Phe Leu Ala Val
335                 340                 345                 350

ATG AAC CAT GAA ATG CGA ACA CCG ATG CAT GCG ATT ATT GCA CTC TCT      1285
Met Asn His Glu Met Arg Thr Pro Met His Ala Ile Ile Ala Leu Ser
                355                 360                 365

TCC TTA CTC CAA GAA ACG GAA CTA ACC CCT GAA CAA AGA CTG ATG GTG      1333
Ser Leu Leu Gln Glu Thr Glu Leu Thr Pro Glu Gln Arg Leu Met Val
            370                 375                 380

GAA ACA ATA CTT AAA AGT AGT AAC CTT TTG GCA ACT TTG ATG AAT GAT      1381
Glu Thr Ile Leu Lys Ser Ser Asn Leu Leu Ala Thr Leu Met Asn Asp
        385                 390                 395

GTC TTA GAT CTT TCA AGG TTA GAA GAT GGA AGT CTT CAA CTT GAA CTT      1429
Val Leu Asp Leu Ser Arg Leu Glu Asp Gly Ser Leu Gln Leu Glu Leu
    400                 405                 410

GGG ACA TTC AAT CTT CAT ACA TTA TTT AGA GAG GTC CTC AAT CTG ATA      1477
Gly Thr Phe Asn Leu His Thr Leu Phe Arg Glu Val Leu Asn Leu Ile
415                 420                 425                 430

AAG CCT ATA GCG GTT GTT AAG AAA TTA CCC ATC ACA CTA AAT CTT GCA      1525
Lys Pro Ile Ala Val Val Lys Lys Leu Pro Ile Thr Leu Asn Leu Ala
                435                 440                 445

CCA GAT TTG CCA GAA TTT GTT GTT GGG GAT GAG AAA CGG CTA ATG CAG      1573
Pro Asp Leu Pro Glu Phe Val Val Gly Asp Glu Lys Arg Leu Met Gln
            450                 455                 460

ATA ATA TTA AAT ATA GTT GGT AAT GCT GTG AAA TTC TCC AAA CAA GGT      1621
Ile Ile Leu Asn Ile Val Gly Asn Ala Val Lys Phe Ser Lys Gln Gly
        465                 470                 475

AGT ATC TCC GTA ACC GCT CTT GTC ACC AAG TCA GAC ACA CGA GCT GCT      1669
Ser Ile Ser Val Thr Ala Leu Val Thr Lys Ser Asp Thr Arg Ala Ala
    480                 485                 490

GAC TTT TTT GTC GTG CCA ACT GGG AGT CAT TTC TAC TTG AGA GTG AAG      1717
Asp Phe Phe Val Val Pro Thr Gly Ser His Phe Tyr Leu Arg Val Lys
495                 500                 505                 510

GTA AAA GAC TCT GGA GCA GGA ATA AAT CCT CAA GAC ATT CCA AAG ATT      1765
Val Lys Asp Ser Gly Ala Gly Ile Asn Pro Gln Asp Ile Pro Lys Ile
                515                 520                 525

TTC ACT AAA TTT GCT CAA ACA CAA TCT TTA GCG ACG AGA AGC TCG GGT      1813
Phe Thr Lys Phe Ala Gln Thr Gln Ser Leu Ala Thr Arg Ser Ser Gly
            530                 535                 540

GGT AGT GGG CTT GGC CTC GCC ATC TCC AAG AGG TTT GTG AAT CTG ATG      1861
Gly Ser Gly Leu Gly Leu Ala Ile Ser Lys Arg Phe Val Asn Leu Met
        545                 550                 555

GAG GGT AAC ATT TGG ATT GAG AGC GAT GGT CTT GGA AAA GGA TGC ACG      1909
Glu Gly Asn Ile Trp Ile Glu Ser Asp Gly Leu Gly Lys Gly Cys Thr
    560                 565                 570
```

-continued

```
GCT ATC TTT GAT GTT AAA CTT GGG ATC TCA GAA CGT TCA AAC GAA TCT     1957
Ala Ile Phe Asp Val Lys Leu Gly Ile Ser Glu Arg Ser Asn Glu Ser
575                 580                 585                 590

AAA CAG TCG GGC ATA CCG AAA GTT CCA GCC ATT CCC CGA CAT TCA AAT     2005
Lys Gln Ser Gly Ile Pro Lys Val Pro Ala Ile Pro Arg His Ser Asn
                595                 600                 605

TTC ACT GGA CTT AAG GTT CTT GTC ATG GAT GAG AAC GGG GTA AGT AGA     2053
Phe Thr Gly Leu Lys Val Leu Val Met Asp Glu Asn Gly Val Ser Arg
            610                 615                 620

ATG GTG ACG AAG GGA CTT CTT GTA CAC CTT GGG TGC GAA GTG ACC ACG     2101
Met Val Thr Lys Gly Leu Leu Val His Leu Gly Cys Glu Val Thr Thr
        625                 630                 635

GTG AGT TCA AAC GAG GAG TGT CTC CGA GTT GTG TCC CAT GAG CAC AAA     2149
Val Ser Ser Asn Glu Glu Cys Leu Arg Val Val Ser His Glu His Lys
    640                 645                 650

GTG GTC TTC ATG GAC GTG TGC ATG CCC GGG GTC GAA AAC TAC CAA ATC     2197
Val Val Phe Met Asp Val Cys Met Pro Gly Val Glu Asn Tyr Gln Ile
655                 660                 665                 670

GCT CTC CGT ATT CAC GAG AAA TTC ACA AAA CAA CGC CAC CAA CGG CCA     2245
Ala Leu Arg Ile His Glu Lys Phe Thr Lys Gln Arg His Gln Arg Pro
                675                 680                 685

CTA CTT GTG GCA CTC AGT GGT AAC ACT GAC AAA TCC ACA AAA GAG AAA     2293
Leu Leu Val Ala Leu Ser Gly Asn Thr Asp Lys Ser Thr Lys Glu Lys
            690                 695                 700

TGC ATG AGC TTT GGT CTA GAC GGT GTG TTG CTC AAA CCC GTA TCA CTA     2341
Cys Met Ser Phe Gly Leu Asp Gly Val Leu Leu Lys Pro Val Ser Leu
        705                 710                 715

GAC AAC ATA AGA GAT GTT CTG TCT GAT CTT CTC GAG CCC CGG GTA CTG     2389
Asp Asn Ile Arg Asp Val Leu Ser Asp Leu Leu Glu Pro Arg Val Leu
    720                 725                 730

TAC GAG GGC ATG TAAAGGCGAT GGATGCCCCA TGCCCCAGAG GAGTAATTCC         2441
Tyr Glu Gly Met
735

GCTCCCGCCT TCTTCTCCCG TAAAACATCG GAAGCTGATG TTCTCTGGTT TAATTGTGTA   2501

CATATCAGAG ATTGTCGGAG CGTTTTGGAT GATATCTTAA AACAGAAAGG GAATAACAAA   2561

ATAGAAACTC TAAACCGGTA TGTGTCCGTG GCGATTTCGG TTATAGAGGA ACAAGATGGT   2621

GGTGGTATAA TCATACCATT TCAGATTACA TGTTTGACTA ATGTTGTATC CTTATATATG   2681

TAGTTACATT CTTATAAGAA TTTGGATCGA GTTATGGATG CTTGTTGCGT GCATGTATGA   2741

CATTGATGCA GTATTATGGC GTCAGCTTTG CGCCGCTTAG TAGAAC                  2787
```

( 2 ) INFORMATION FOR SEQ ID NO:3:

( i ) SEQUENCE CHARACTERISTICS:
( A ) LENGTH: 738 amino acids
( B ) TYPE: amino acid
( D ) TOPOLOGY: linear ( i i ) MOLECULE TYPE: protein ( x i ) SEQUENCE DESCRIPTION: SEQ ID NO:3:

```
Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Val Gln Phe Gly Ala Phe Ile Val Leu
     50                  55                  60
```

-continued

```
Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
                245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
            340                 345                 350

His Glu Met Arg Thr Pro Met His Ala Ile Ile Ala Leu Ser Ser Leu
        355                 360                 365

Leu Gln Glu Thr Glu Leu Thr Pro Glu Gln Arg Leu Met Val Glu Thr
    370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
                405                 410                 415

Phe Asn Leu His Thr Leu Phe Arg Glu Val Leu Asn Leu Ile Lys Pro
            420                 425                 430

Ile Ala Val Val Lys Lys Leu Pro Ile Thr Leu Asn Leu Ala Pro Asp
        435                 440                 445

Leu Pro Glu Phe Val Val Gly Asp Glu Lys Arg Leu Met Gln Ile Ile
    450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495
```

-continued

```
Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met
```

( 2 ) INFORMATION FOR SEQ ID NO:4:

( i ) SEQUENCE CHARACTERISTICS:
( A ) LENGTH: 2787 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 188..2401

( x i ) SEQUENCE DESCRIPTION: SEQ ID NO:4:

```
AGTAAGAACG AAGAAGAAGT GTTAAACCCA ACCAATTTTG ACTTGAAAAA AAGCTTCAAC     60

GCTCCCCTTT TCTCCTTCTC CGTCGCTCTC CGCCGCGTCC CAAATCCCCA ATTCCTCCTC    120

TTCTCCGATC AATTCTTCCC AAGTGTGTGT ATGTGTGAGA GAGGAACTAT AGTGTAAAAA    180

ATTCATA ATG GAA GTC TGC AAT TGT ATT GAA CCG CAA TGG CCA GCG GAT      229
        Met Glu Val Cys Asn Cys Ile Glu Pro Gln Trp Pro Ala Asp
          1               5                  10

GAA TTG TTA ATG AAA TAC CAA TAC ATC TCC GAT TTC TTC ATT GCG ATT      277
Glu Leu Leu Met Lys Tyr Gln Tyr Ile Ser Asp Phe Phe Ile Ala Ile
 15                  20                  25                  30

GCG TAT TTT TCG ATT CCT CTT GAG TTG ATT TAC TTT GTG AAG AAA TCA      325
```

-continued

```
Ala Tyr Phe Ser Ile Pro Leu Glu Leu Ile Tyr Phe Val Lys Lys Ser
                35                  40                  45

GCC GTG TTT CCG TAT AGA TGG GTA CTT GTT CAG TTT GGT GCT TTT ATC      373
Ala Val Phe Pro Tyr Arg Trp Val Leu Val Gln Phe Gly Ala Phe Ile
            50                  55                  60

GTT CTT TAT GGA GCA ACT CAT CTT ATT AAC TTA TGG ACT TTC ACT ACG      421
Val Leu Tyr Gly Ala Thr His Leu Ile Asn Leu Trp Thr Phe Thr Thr
        65                  70                  75

CAT TCG AGA ACC GTG GCG CTT GTG ATG ACT ACC GCG AAG GTG TTA ACC      469
His Ser Arg Thr Val Ala Leu Val Met Thr Thr Ala Lys Val Leu Thr
    80                  85                  90

GCT GTT GTC TCG TGT GCT ACT GCG TTG ATG CTT GTT CAT ATT ATT CCT      517
Ala Val Val Ser Cys Ala Thr Ala Leu Met Leu Val His Ile Ile Pro
95                  100                 105                 110

GAT CTT TTG AGT GTT AAG ACT CGG GAG CTT TTC TTG AAA AAT AAA GCT      565
Asp Leu Leu Ser Val Lys Thr Arg Glu Leu Phe Leu Lys Asn Lys Ala
                115                 120                 125

GCT GAG CTC GAT AGA GAA ATG GGA TTG ATT CGA ACT CAG GAA GAA ACC      613
Ala Glu Leu Asp Arg Glu Met Gly Leu Ile Arg Thr Gln Glu Glu Thr
            130                 135                 140

GGA AGG CAT GTG AGA ATG TTG ACT CAT GAG ATT AGA AGC ACT TTA GAT      661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA      709
Arg His Thr Ile Leu Lys Thr Thr Leu Val Glu Leu Gly Arg Thr Leu
    160                 165                 170

GCT TTG GAG GAG TGT GCA TTG TGG ATG CCT ACT AGA ACT GGG TTA GAG      757
Ala Leu Glu Glu Cys Ala Leu Trp Met Pro Thr Arg Thr Gly Leu Glu
175                 180                 185                 190

CTA CAG CTT TCT TAT ACA CTT CGT CAT CAA CAT CCC GTG GAG TAT ACG      805
Leu Gln Leu Ser Tyr Thr Leu Arg His Gln His Pro Val Glu Tyr Thr
                195                 200                 205

GTT CCT ATT CAA TTA CCG GTG ATT AAC CAA GTG TTT GGT ACT AGT AGG      853
Val Pro Ile Gln Leu Pro Val Ile Asn Gln Val Phe Gly Thr Ser Arg
            210                 215                 220

GCT GTA AAA ATA TCT CCT AAT TCT CCT GTG GCT AGG TTG AGA CCT GTT      901
Ala Val Lys Ile Ser Pro Asn Ser Pro Val Ala Arg Leu Arg Pro Val
        225                 230                 235

TCT GGG AAA TAT ATG CTA GGG GAG GTG GTC GCT GTG AGG GTT CCG CTT      949
Ser Gly Lys Tyr Met Leu Gly Glu Val Val Ala Val Arg Val Pro Leu
    240                 245                 250

CTC CAC CTT TCT AAT TTT CAG ATT AAT GAC TGG CCT GAG CTT TCA ACA      997
Leu His Leu Ser Asn Phe Gln Ile Asn Asp Trp Pro Glu Leu Ser Thr
255                 260                 265                 270

AAG AGA TAT GCT TTG ATG GTT TTG ATG CTT CCT TCA GAT AGT GCA AGG     1045
Lys Arg Tyr Ala Leu Met Val Leu Met Leu Pro Ser Asp Ser Ala Arg
                275                 280                 285

CAA TGG CAT GTC CAT GAG TTG GAA CTC GTT GAA GTC GTC GCT GAT CAG     1093
Gln Trp His Val His Glu Leu Glu Leu Val Glu Val Val Ala Asp Gln
            290                 295                 300

GTG GCT GTA GCT CTC TCA CAT GCT GCG ATC CTA GAA GAG TCG ATG CGA     1141
Val Ala Val Ala Leu Ser His Ala Ala Ile Leu Glu Glu Ser Met Arg
        305                 310                 315

GCT AGG GAC CTT CTC ATG GAG CAG AAT GTT GCT CTT GAT CTA GCT AGA     1189
Ala Arg Asp Leu Leu Met Glu Gln Asn Val Ala Leu Asp Leu Ala Arg
    320                 325                 330

CGA GAA GCA GAA ACA GCA ATC CGT GCC CGC AAT GAT TTC CTA GCG GTT     1237
Arg Glu Ala Glu Thr Ala Ile Arg Ala Arg Asn Asp Phe Leu Ala Val
335                 340                 345                 350

ATG AAC CAT GAA ATG CGA ACA CCG ATG CAT GCG ATT ATT GCA CTC TCT     1285
```

-continued

```
Met Asn His Glu Met Arg Thr Pro Met His Ala Ile Ile Ala Leu Ser
                355                 360                 365

TCC TTA CTC CAA GAA ACG GAA CTA ACC CCT GAA CAA AGA CTG ATG GTG     1333
Ser Leu Leu Gln Glu Thr Glu Leu Thr Pro Glu Gln Arg Leu Met Val
            370                 375                 380

GAA ACA ATA CTT AAA AGT AGT AAC CTT TTG GCA ACT TTG ATG AAT GAT     1381
Glu Thr Ile Leu Lys Ser Ser Asn Leu Leu Ala Thr Leu Met Asn Asp
        385                 390                 395

GTC TTA GAT CTT TCA AGG TTA GAA GAT GGA AGT CTT CAA CTT GAA CTT     1429
Val Leu Asp Leu Ser Arg Leu Glu Asp Gly Ser Leu Gln Leu Glu Leu
    400                 405                 410

GGG ACA TTC AAT CTT CAT ACA TTA TTT AGA GAG GTC CTC AAT CTG ATA     1477
Gly Thr Phe Asn Leu His Thr Leu Phe Arg Glu Val Leu Asn Leu Ile
415                 420                 425                 430

AAG CCT ATA GCG GTT GTT AAG AAA TTA CCC ATC ACA CTA AAT CTT GCA     1525
Lys Pro Ile Ala Val Val Lys Lys Leu Pro Ile Thr Leu Asn Leu Ala
                435                 440                 445

CCA GAT TTG CCA GAA TTT GTT GTT GGG GAT GAG AAA CGG CTA ATG CAG     1573
Pro Asp Leu Pro Glu Phe Val Val Gly Asp Glu Lys Arg Leu Met Gln
            450                 455                 460

ATA ATA TTA AAT ATA GTT GGT AAT GCT GTG AAA TTC TCC AAA CAA GGT     1621
Ile Ile Leu Asn Ile Val Gly Asn Ala Val Lys Phe Ser Lys Gln Gly
        465                 470                 475

AGT ATC TCC GTA ACC GCT CTT GTC ACC AAG TCA GAC ACA CGA GCT GCT     1669
Ser Ile Ser Val Thr Ala Leu Val Thr Lys Ser Asp Thr Arg Ala Ala
    480                 485                 490

GAC TTT TTT GTC GTG CCA ACT GGG AGT CAT TTC TAC TTG AGA GTG AAG     1717
Asp Phe Phe Val Val Pro Thr Gly Ser His Phe Tyr Leu Arg Val Lys
495                 500                 505                 510

GTA AAA GAC TCT GGA GCA GGA ATA AAT CCT CAA GAC ATT CCA AAG ATT     1765
Val Lys Asp Ser Gly Ala Gly Ile Asn Pro Gln Asp Ile Pro Lys Ile
                515                 520                 525

TTC ACT AAA TTT GCT CAA ACA CAA TCT TTA GCG ACG AGA AGC TCG GGT     1813
Phe Thr Lys Phe Ala Gln Thr Gln Ser Leu Ala Thr Arg Ser Ser Gly
            530                 535                 540

GGT AGT GGG CTT GGC CTC GCC ATC TCC AAG AGG TTT GTG AAT CTG ATG     1861
Gly Ser Gly Leu Gly Leu Ala Ile Ser Lys Arg Phe Val Asn Leu Met
        545                 550                 555

GAG GGT AAC ATT TGG ATT GAG AGC GAT GGT CTT GGA AAA GGA TGC ACG     1909
Glu Gly Asn Ile Trp Ile Glu Ser Asp Gly Leu Gly Lys Gly Cys Thr
    560                 565                 570

GCT ATC TTT GAT GTT AAA CTT GGG ATC TCA GAA CGT TCA AAC GAA TCT     1957
Ala Ile Phe Asp Val Lys Leu Gly Ile Ser Glu Arg Ser Asn Glu Ser
575                 580                 585                 590

AAA CAG TCG GGC ATA CCG AAA GTT CCA GCC ATT CCC CGA CAT TCA AAT     2005
Lys Gln Ser Gly Ile Pro Lys Val Pro Ala Ile Pro Arg His Ser Asn
                595                 600                 605

TTC ACT GGA CTT AAG GTT CTT GTC ATG GAT GAG AAC GGG GTA AGT AGA     2053
Phe Thr Gly Leu Lys Val Leu Val Met Asp Glu Asn Gly Val Ser Arg
            610                 615                 620

ATG GTG ACG AAG GGA CTT CTT GTA CAC CTT GGG TGC GAA GTG ACC ACG     2101
Met Val Thr Lys Gly Leu Leu Val His Leu Gly Cys Glu Val Thr Thr
        625                 630                 635

GTG AGT TCA AAC GAG GAG TGT CTC CGA GTT GTG TCC CAT GAG CAC AAA     2149
Val Ser Ser Asn Glu Glu Cys Leu Arg Val Val Ser His Glu His Lys
    640                 645                 650

GTG GTC TTC ATG GAC GTG TGC ATG CCC GGG GTC GAA AAC TAC CAA ATC     2197
Val Val Phe Met Asp Val Cys Met Pro Gly Val Glu Asn Tyr Gln Ile
655                 660                 665                 670

GCT CTC CGT ATT CAC GAG AAA TTC ACA AAA CAA CGC CAC CAA CGG CCA     2245
```

-continued

```
Ala Leu Arg Ile His Glu Lys Phe Thr Lys Gln Arg His Gln Arg Pro
                675                 680                 685

CTA CTT GTG GCA CTC AGT GGT AAC ACT GAC AAA TCC ACA AAA GAG AAA     2293
Leu Leu Val Ala Leu Ser Gly Asn Thr Asp Lys Ser Thr Lys Glu Lys
            690                 695                 700

TGC ATG AGC TTT GGT CTA GAC GGT GTG TTG CTC AAA CCC GTA TCA CTA     2341
Cys Met Ser Phe Gly Leu Asp Gly Val Leu Leu Lys Pro Val Ser Leu
        705                 710                 715

GAC AAC ATA AGA GAT GTT CTG TCT GAT CTT CTC GAG CCC CGG GTA CTG     2389
Asp Asn Ile Arg Asp Val Leu Ser Asp Leu Leu Glu Pro Arg Val Leu
    720                 725                 730

TAC GAG GGC ATG TAAAGGCGAT GGATGCCCCA TGCCCCAGAG GAGTAATTCC         2441
Tyr Glu Gly Met
735

GCTCCCGCCT TCTTCTCCCG TAAAACATCG GAAGCTGATG TTCTCTGGTT TAATTGTGTA   2501

CATATCAGAG ATTGTCGGAG CGTTTTGGAT GATATCTTAA AACAGAAAGG GAATAACAAA   2561

ATAGAAACTC TAAACCGGTA TGTGTCCGTG GCGATTTCGG TTATAGAGGA ACAAGATGGT   2621

GGTGGTATAA TCATACCATT TCAGATTACA TGTTTGACTA ATGTTGTATC CTTATATATG   2681

TAGTTACATT CTTATAAGAA TTTGGATCGA GTTATGGATG CTTGTTGCGT GCATGTATGA   2741

CATTGATGCA GTATTATGGC GTCAGCTTTG CGCCGCTTAG TAGAAC                  2787
```

( 2 ) INFORMATION FOR SEQ ID NO:5:

( i ) SEQUENCE CHARACTERISTICS:
( A ) LENGTH: 738 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Met Glu Val Cys Asn Cys Ile Glu Pro Gln Trp Pro Ala Asp Glu Leu
 1               5                  10                  15

Leu Met Lys Tyr Gln Tyr Ile Ser Asp Phe Phe Ile Ala Ile Ala Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Ile Val Leu
    50                  55                  60

Tyr Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
```

-continued

```
        195                                 200                                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
                245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
            340                 345                 350

His Glu Met Arg Thr Pro Met His Ala Ile Ile Ala Leu Ser Ser Leu
        355                 360                 365

Leu Gln Glu Thr Glu Leu Thr Pro Glu Gln Arg Leu Met Val Glu Thr
    370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
                405                 410                 415

Phe Asn Leu His Thr Leu Phe Arg Glu Val Leu Asn Leu Ile Lys Pro
            420                 425                 430

Ile Ala Val Val Lys Lys Leu Pro Ile Thr Leu Asn Leu Ala Pro Asp
        435                 440                 445

Leu Pro Glu Phe Val Val Gly Asp Glu Lys Arg Leu Met Gln Ile Ile
    450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620
```

-continued

```
Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met
```

( 2 ) INFORMATION FOR SEQ ID NO:6:

( i ) SEQUENCE CHARACTERISTICS:
( A ) LENGTH: 2787 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 188..2401

( x i ) SEQUENCE DESCRIPTION: SEQ ID NO:6:

```
AGTAAGAACG AAGAAGAAGT GTTAAACCCA ACCAATTTTG ACTTGAAAAA AAGCTTCAAC     60

GCTCCCCTTT TCTCCTTCTC CGTCGCTCTC CGCCGCGTCC CAAATCCCCA ATTCCTCCTC    120

TTCTCCGATC AATTCTTCCC AAGTGTGTGT ATGTGTGAGA GAGGAACTAT AGTGTAAAAA    180

ATTCATA ATG GAA GTC TGC AAT TGT ATT GAA CCG CAA TGG CCA GCG GAT      229
        Met Glu Val Cys Asn Cys Ile Glu Pro Gln Trp Pro Ala Asp
          1               5                  10

GAA TTG TTA ATG AAA TAC CAA TAC ATC TCC GAT TTC TTC ATT GCG ATT      277
Glu Leu Leu Met Lys Tyr Gln Tyr Ile Ser Asp Phe Phe Ile Ala Ile
 15                  20                  25                  30

GCG TAT TTT TCG ATT CCT CTT GAG TTG ATT TAC TTT GTG AAG AAA TCA      325
Ala Tyr Phe Ser Ile Pro Leu Glu Leu Ile Tyr Phe Val Lys Lys Ser
                 35                  40                  45

GCC GTG TTT CCG TAT AGA TGG GTA CTT GTT CAG TTT GGT GCT TTT ATC      373
Ala Val Phe Pro Tyr Arg Trp Val Leu Val Gln Phe Gly Ala Phe Ile
             50                  55                  60

GTT CTT TGT GGA GCA ACT CAT CTT ATT AAC TTA TGG ACT TTC ACT ACG      421
Val Leu Cys Gly Ala Thr His Leu Ile Asn Leu Trp Thr Phe Thr Thr
         65                  70                  75

CAT TCG AGA ACC GTG GCG CTT GTG ATG ACT ACC GCG AAG GTG TTA ACC      469
His Ser Arg Thr Val Ala Leu Val Met Thr Thr Ala Lys Val Leu Thr
     80                  85                  90

GCT GTT GTC TCG TGT GCT ACT ACG TTG ATG CTT GTT CAT ATT ATT CCT      517
Ala Val Val Ser Cys Ala Thr Thr Leu Met Leu Val His Ile Ile Pro
 95                 100                 105                 110

GAT CTT TTG AGT GTT AAG ACT CGG GAG CTT TTC TTG AAA AAT AAA GCT      565
Asp Leu Leu Ser Val Lys Thr Arg Glu Leu Phe Leu Lys Asn Lys Ala
                115                 120                 125

GCT GAG CTC GAT AGA GAA ATG GGA TTG ATT CGA ACT CAG GAA GAA ACC      613
```

-continued

```
Ala Glu Leu Asp Arg Glu Met Gly Leu Ile Arg Thr Gln Glu Glu Thr
            130                 135                 140

GGA AGG CAT GTG AGA ATG TTG ACT CAT GAG ATT AGA AGC ACT TTA GAT      661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA      709
Arg His Thr Ile Leu Lys Thr Thr Leu Val Glu Leu Gly Arg Thr Leu
    160                 165                 170

GCT TTG GAG GAG TGT GCA TTG TGG ATG CCT ACT AGA ACT GGG TTA GAG      757
Ala Leu Glu Glu Cys Ala Leu Trp Met Pro Thr Arg Thr Gly Leu Glu
175                 180                 185                 190

CTA CAG CTT TCT TAT ACA CTT CGT CAT CAA CAT CCC GTG GAG TAT ACG      805
Leu Gln Leu Ser Tyr Thr Leu Arg His Gln His Pro Val Glu Tyr Thr
                195                 200                 205

GTT CCT ATT CAA TTA CCG GTG ATT AAC CAA GTG TTT GGT ACT AGT AGG      853
Val Pro Ile Gln Leu Pro Val Ile Asn Gln Val Phe Gly Thr Ser Arg
            210                 215                 220

GCT GTA AAA ATA TCT CCT AAT TCT CCT GTG GCT AGG TTG AGA CCT GTT      901
Ala Val Lys Ile Ser Pro Asn Ser Pro Val Ala Arg Leu Arg Pro Val
        225                 230                 235

TCT GGG AAA TAT ATG CTA GGG GAG GTG GTC GCT GTG AGG GTT CCG CTT      949
Ser Gly Lys Tyr Met Leu Gly Glu Val Val Ala Val Arg Val Pro Leu
    240                 245                 250

CTC CAC CTT TCT AAT TTT CAG ATT AAT GAC TGG CCT GAG CTT TCA ACA      997
Leu His Leu Ser Asn Phe Gln Ile Asn Asp Trp Pro Glu Leu Ser Thr
255                 260                 265                 270

AAG AGA TAT GCT TTG ATG GTT TTG ATG CTT CCT TCA GAT AGT GCA AGG     1045
Lys Arg Tyr Ala Leu Met Val Leu Met Leu Pro Ser Asp Ser Ala Arg
                275                 280                 285

CAA TGG CAT GTC CAT GAG TTG GAA CTC GTT GAA GTC GTC GCT GAT CAG     1093
Gln Trp His Val His Glu Leu Glu Leu Val Glu Val Val Ala Asp Gln
            290                 295                 300

GTG GCT GTA GCT CTC TCA CAT GCT GCG ATC CTA GAA GAG TCG ATG CGA     1141
Val Ala Val Ala Leu Ser His Ala Ala Ile Leu Glu Glu Ser Met Arg
        305                 310                 315

GCT AGG GAC CTT CTC ATG GAG CAG AAT GTT GCT CTT GAT CTA GCT AGA     1189
Ala Arg Asp Leu Leu Met Glu Gln Asn Val Ala Leu Asp Leu Ala Arg
    320                 325                 330

CGA GAA GCA GAA ACA GCA ATC CGT GCC CGC AAT GAT TTC CTA GCG GTT     1237
Arg Glu Ala Glu Thr Ala Ile Arg Ala Arg Asn Asp Phe Leu Ala Val
335                 340                 345                 350

ATG AAC CAT GAA ATG CGA ACA CCG ATG CAT GCG ATT ATT GCA CTC TCT     1285
Met Asn His Glu Met Arg Thr Pro Met His Ala Ile Ile Ala Leu Ser
                355                 360                 365

TCC TTA CTC CAA GAA ACG GAA CTA ACC CCT GAA CAA AGA CTG ATG GTG     1333
Ser Leu Leu Gln Glu Thr Glu Leu Thr Pro Glu Gln Arg Leu Met Val
            370                 375                 380

GAA ACA ATA CTT AAA AGT AGT AAC CTT TTG GCA ACT TTG ATG AAT GAT     1381
Glu Thr Ile Leu Lys Ser Ser Asn Leu Leu Ala Thr Leu Met Asn Asp
        385                 390                 395

GTC TTA GAT CTT TCA AGG TTA GAA GAT GGA AGT CTT CAA CTT GAA CTT     1429
Val Leu Asp Leu Ser Arg Leu Glu Asp Gly Ser Leu Gln Leu Glu Leu
    400                 405                 410

GGG ACA TTC AAT CTT CAT ACA TTA TTT AGA GAG GTC CTC AAT CTG ATA     1477
Gly Thr Phe Asn Leu His Thr Leu Phe Arg Glu Val Leu Asn Leu Ile
415                 420                 425                 430

AAG CCT ATA GCG GTT GTT AAG AAA TTA CCC ATC ACA CTA AAT CTT GCA     1525
Lys Pro Ile Ala Val Val Lys Lys Leu Pro Ile Thr Leu Asn Leu Ala
                435                 440                 445

CCA GAT TTG CCA GAA TTT GTT GTT GGG GAT GAG AAA CGG CTA ATG CAG     1573
```

-continued

```
Pro Asp Leu Pro Glu Phe Val Val Gly Asp Glu Lys Arg Leu Met Gln
            450                 455                 460

ATA ATA TTA AAT ATA GTT GGT AAT GCT GTG AAA TTC TCC AAA CAA GGT     1621
Ile Ile Leu Asn Ile Val Gly Asn Ala Val Lys Phe Ser Lys Gln Gly
        465                 470                 475

AGT ATC TCC GTA ACC GCT CTT GTC ACC AAG TCA GAC ACA CGA GCT GCT     1669
Ser Ile Ser Val Thr Ala Leu Val Thr Lys Ser Asp Thr Arg Ala Ala
    480                 485                 490

GAC TTT TTT GTC GTG CCA ACT GGG AGT CAT TTC TAC TTG AGA GTG AAG     1717
Asp Phe Phe Val Val Pro Thr Gly Ser His Phe Tyr Leu Arg Val Lys
495                 500                 505                 510

GTA AAA GAC TCT GGA GCA GGA ATA AAT CCT CAA GAC ATT CCA AAG ATT     1765
Val Lys Asp Ser Gly Ala Gly Ile Asn Pro Gln Asp Ile Pro Lys Ile
            515                 520                 525

TTC ACT AAA TTT GCT CAA ACA CAA TCT TTA GCG ACG AGA AGC TCG GGT     1813
Phe Thr Lys Phe Ala Gln Thr Gln Ser Leu Ala Thr Arg Ser Ser Gly
            530                 535                 540

GGT AGT GGG CTT GGC CTC GCC ATC TCC AAG AGG TTT GTG AAT CTG ATG     1861
Gly Ser Gly Leu Gly Leu Ala Ile Ser Lys Arg Phe Val Asn Leu Met
        545                 550                 555

GAG GGT AAC ATT TGG ATT GAG AGC GAT GGT CTT GGA AAA GGA TGC ACG     1909
Glu Gly Asn Ile Trp Ile Glu Ser Asp Gly Leu Gly Lys Gly Cys Thr
    560                 565                 570

GCT ATC TTT GAT GTT AAA CTT GGG ATC TCA GAA CGT TCA AAC GAA TCT     1957
Ala Ile Phe Asp Val Lys Leu Gly Ile Ser Glu Arg Ser Asn Glu Ser
575                 580                 585                 590

AAA CAG TCG GGC ATA CCG AAA GTT CCA GCC ATT CCC CGA CAT TCA AAT     2005
Lys Gln Ser Gly Ile Pro Lys Val Pro Ala Ile Pro Arg His Ser Asn
            595                 600                 605

TTC ACT GGA CTT AAG GTT CTT GTC ATG GAT GAG AAC GGG GTA AGT AGA     2053
Phe Thr Gly Leu Lys Val Leu Val Met Asp Glu Asn Gly Val Ser Arg
            610                 615                 620

ATG GTG ACG AAG GGA CTT CTT GTA CAC CTT GGG TGC GAA GTG ACC ACG     2101
Met Val Thr Lys Gly Leu Leu Val His Leu Gly Cys Glu Val Thr Thr
        625                 630                 635

GTG AGT TCA AAC GAG GAG TGT CTC CGA GTT GTG TCC CAT GAG CAC AAA     2149
Val Ser Ser Asn Glu Glu Cys Leu Arg Val Val Ser His Glu His Lys
    640                 645                 650

GTG GTC TTC ATG GAC GTG TGC ATG CCC GGG GTC GAA AAC TAC CAA ATC     2197
Val Val Phe Met Asp Val Cys Met Pro Gly Val Glu Asn Tyr Gln Ile
655                 660                 665                 670

GCT CTC CGT ATT CAC GAG AAA TTC ACA AAA CAA CGC CAC CAA CGG CCA     2245
Ala Leu Arg Ile His Glu Lys Phe Thr Lys Gln Arg His Gln Arg Pro
            675                 680                 685

CTA CTT GTG GCA CTC AGT GGT AAC ACT GAC AAA TCC ACA AAA GAG AAA     2293
Leu Leu Val Ala Leu Ser Gly Asn Thr Asp Lys Ser Thr Lys Glu Lys
            690                 695                 700

TGC ATG AGC TTT GGT CTA GAC GGT GTG TTG CTC AAA CCC GTA TCA CTA     2341
Cys Met Ser Phe Gly Leu Asp Gly Val Leu Leu Lys Pro Val Ser Leu
        705                 710                 715

GAC AAC ATA AGA GAT GTT CTG TCT GAT CTT CTC GAG CCC CGG GTA CTG     2389
Asp Asn Ile Arg Asp Val Leu Ser Asp Leu Leu Glu Pro Arg Val Leu
    720                 725                 730

TAC GAG GGC ATG TAAAGGCGAT GGATGCCCCA TGCCCCAGAG GAGTAATTCC         2441
Tyr Glu Gly Met
735

GCTCCCGCCT TCTTCTCCCG TAAAACATCG GAAGCTGATG TTCTCTGGTT TAATTGTGTA   2501

CATATCAGAG ATTGTCGGAG CGTTTTGGAT GATATCTTAA AACAGAAAGG GAATAACAAA   2561

ATAGAAACTC TAAACCGGTA TGTGTCCGTG GCGATTTCGG TTATAGAGGA ACAAGATGGT   2621
```

GGTGGTATAA TCATACCATT TCAGATTACA TGTTTGACTA ATGTTGTATC CTTATATATG 2681

TAGTTACATT CTTATAAGAA TTTGGATCGA GTTATGGATG CTTGTTGCGT GCATGTATGA 2741

CATTGATGCA GTATTATGGC GTCAGCTTTG CGCCGCTTAG TAGAAC 2787

( 2 ) INFORMATION FOR SEQ ID NO:7:

( i ) SEQUENCE CHARACTERISTICS:
( A ) LENGTH: 738 amino acids
( B ) TYPE: amino acid
( D ) TOPOLOGY: linear ( i i ) MOLECULE TYPE: protein ( x i ) SEQUENCE DESCRIPTION: SEQ ID NO:7:

Met Glu Val Cys Asn Cys Ile Glu Pro Gln Trp Pro Ala Asp Glu Leu
1 5 10 15

Leu Met Lys Tyr Gln Tyr Ile Ser Asp Phe Phe Ile Ala Ile Ala Tyr
20 25 30

Phe Ser Ile Pro Leu Glu Leu Ile Tyr Phe Val Lys Lys Ser Ala Val
35 40 45

Phe Pro Tyr Arg Trp Val Leu Val Gln Phe Gly Ala Phe Ile Val Leu
50 55 60

Cys Gly Ala Thr His Leu Ile Asn Leu Trp Thr Phe Thr Thr His Ser
65 70 75 80

Arg Thr Val Ala Leu Val Met Thr Thr Ala Lys Val Leu Thr Ala Val
85 90 95

Val Ser Cys Ala Thr Thr Leu Met Leu Val His Ile Ile Pro Asp Leu
100 105 110

Leu Ser Val Lys Thr Arg Glu Leu Phe Leu Lys Asn Lys Ala Ala Glu
115 120 125

Leu Asp Arg Glu Met Gly Leu Ile Arg Thr Gln Glu Glu Thr Gly Arg
130 135 140

His Val Arg Met Leu Thr His Glu Ile Arg Ser Thr Leu Asp Arg His
145 150 155 160

Thr Ile Leu Lys Thr Thr Leu Val Glu Leu Gly Arg Thr Leu Ala Leu
165 170 175

Glu Glu Cys Ala Leu Trp Met Pro Thr Arg Thr Gly Leu Glu Leu Gln
180 185 190

Leu Ser Tyr Thr Leu Arg His Gln His Pro Val Glu Tyr Thr Val Pro
195 200 205

Ile Gln Leu Pro Val Ile Asn Gln Val Phe Gly Thr Ser Arg Ala Val
210 215 220

Lys Ile Ser Pro Asn Ser Pro Val Ala Arg Leu Arg Pro Val Ser Gly
225 230 235 240

Lys Tyr Met Leu Gly Glu Val Val Ala Val Arg Val Pro Leu Leu His
245 250 255

Leu Ser Asn Phe Gln Ile Asn Asp Trp Pro Glu Leu Ser Thr Lys Arg
260 265 270

Tyr Ala Leu Met Val Leu Met Leu Pro Ser Asp Ser Ala Arg Gln Trp
275 280 285

His Val His Glu Leu Glu Leu Val Glu Val Val Ala Asp Gln Val Ala
290 295 300

Val Ala Leu Ser His Ala Ala Ile Leu Glu Glu Ser Met Arg Ala Arg
305 310 315 320

Asp Leu Leu Met Glu Gln Asn Val Ala Leu Asp Leu Ala Arg Arg Glu

-continued

```
                        325                                     330                                     335

Ala Glu Thr Ala Ile Arg Ala Arg Asn Asp Phe Leu Ala Val Met Asn
            340                     345                     350

His Glu Met Arg Thr Pro Met His Ala Ile Ile Ala Leu Ser Ser Leu
        355                     360                     365

Leu Gln Glu Thr Glu Leu Thr Pro Glu Gln Arg Leu Met Val Glu Thr
    370                     375                     380

Ile Leu Lys Ser Ser Asn Leu Leu Ala Thr Leu Met Asn Asp Val Leu
385                     390                     395                     400

Asp Leu Ser Arg Leu Glu Asp Gly Ser Leu Gln Leu Glu Leu Gly Thr
                405                     410                     415

Phe Asn Leu His Thr Leu Phe Arg Glu Val Leu Asn Leu Ile Lys Pro
            420                     425                     430

Ile Ala Val Val Lys Lys Leu Pro Ile Thr Leu Asn Leu Ala Pro Asp
        435                     440                     445

Leu Pro Glu Phe Val Val Gly Asp Glu Lys Arg Leu Met Gln Ile Ile
    450                     455                     460

Leu Asn Ile Val Gly Asn Ala Val Lys Phe Ser Lys Gln Gly Ser Ile
465                     470                     475                     480

Ser Val Thr Ala Leu Val Thr Lys Ser Asp Thr Arg Ala Ala Asp Phe
                485                     490                     495

Phe Val Val Pro Thr Gly Ser His Phe Tyr Leu Arg Val Lys Val Lys
            500                     505                     510

Asp Ser Gly Ala Gly Ile Asn Pro Gln Asp Ile Pro Lys Ile Phe Thr
        515                     520                     525

Lys Phe Ala Gln Thr Gln Ser Leu Ala Thr Arg Ser Ser Gly Gly Ser
    530                     535                     540

Gly Leu Gly Leu Ala Ile Ser Lys Arg Phe Val Asn Leu Met Glu Gly
545                     550                     555                     560

Asn Ile Trp Ile Glu Ser Asp Gly Leu Gly Lys Gly Cys Thr Ala Ile
                565                     570                     575

Phe Asp Val Lys Leu Gly Ile Ser Glu Arg Ser Asn Glu Ser Lys Gln
            580                     585                     590

Ser Gly Ile Pro Lys Val Pro Ala Ile Pro Arg His Ser Asn Phe Thr
        595                     600                     605

Gly Leu Lys Val Leu Val Met Asp Glu Asn Gly Val Ser Arg Met Val
    610                     615                     620

Thr Lys Gly Leu Leu Val His Leu Gly Cys Glu Val Thr Thr Val Ser
625                     630                     635                     640

Ser Asn Glu Glu Cys Leu Arg Val Val Ser His Glu His Lys Val Val
                645                     650                     655

Phe Met Asp Val Cys Met Pro Gly Val Glu Asn Tyr Gln Ile Ala Leu
            660                     665                     670

Arg Ile His Glu Lys Phe Thr Lys Gln Arg His Gln Arg Pro Leu Leu
        675                     680                     685

Val Ala Leu Ser Gly Asn Thr Asp Lys Ser Thr Lys Glu Lys Cys Met
    690                     695                     700

Ser Phe Gly Leu Asp Gly Val Leu Leu Lys Pro Val Ser Leu Asp Asn
705                     710                     715                     720

Ile Arg Asp Val Leu Ser Asp Leu Leu Glu Pro Arg Val Leu Tyr Glu
                725                     730                     735

Gly Met
```

( 2 ) INFORMATION FOR SEQ ID NO:8:

( i ) SEQUENCE CHARACTERISTICS:
( A ) LENGTH: 2787 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 188..2401

( x i ) SEQUENCE DESCRIPTION: SEQ ID NO:8:

```
AGTAAGAACG AAGAAGAAGT GTTAAACCCA ACCAATTTTG ACTTGAAAAA AAGCTTCAAC      60

GCTCCCCTTT TCTCCTTCTC CGTCGCTCTC CGCCGCGTCC CAAATCCCCA ATTCCTCCTC     120

TTCTCCGATC AATTCTTCCC AAGTGTGTGT ATGTGTGAGA GAGGAACTAT AGTGTAAAAA     180

ATTCATA ATG GAA GTC TGC AAT TGT ATT GAA CCG CAA TGG CCA GCG GAT       229
        Met Glu Val Cys Asn Cys Ile Glu Pro Gln Trp Pro Ala Asp
          1               5                  10

GAA TTG TTA ATG AAA TAC CAA TAC ATC TCC GAT TTC TTC ATT GCG ATT       277
Glu Leu Leu Met Lys Tyr Gln Tyr Ile Ser Asp Phe Phe Ile Ala Ile
 15                  20                  25                  30

GTG TAT TTT TCG ATT CCT CTT GAG TTG ATT TAC TTT GTG AAG AAA TCA       325
Val Tyr Phe Ser Ile Pro Leu Glu Leu Ile Tyr Phe Val Lys Lys Ser
                 35                  40                  45

GCC GTG TTT CCG TAT AGA TGG GTA CTT GTT CAG TTT GGT GCT TTT ATC       373
Ala Val Phe Pro Tyr Arg Trp Val Leu Val Gln Phe Gly Ala Phe Ile
             50                  55                  60

GTT CTT TGT GGA GCA ACT CAT CTT ATT AAC TTA TGG ACT TTC ACT ACG       421
Val Leu Cys Gly Ala Thr His Leu Ile Asn Leu Trp Thr Phe Thr Thr
         65                  70                  75

CAT TCG AGA ACC GTG GCG CTT GTG ATG ACT ACC GCG AAG GTG TTA ACC       469
His Ser Arg Thr Val Ala Leu Val Met Thr Thr Ala Lys Val Leu Thr
     80                  85                  90

GCT GTT GTC TCG TGT GCT ACT GCG TTG ATG CTT GTT CAT ATT ATT CCT       517
Ala Val Val Ser Cys Ala Thr Ala Leu Met Leu Val His Ile Ile Pro
 95                 100                 105                 110

GAT CTT TTG AGT GTT AAG ACT CGG GAG CTT TTC TTG AAA AAT AAA GCT       565
Asp Leu Leu Ser Val Lys Thr Arg Glu Leu Phe Leu Lys Asn Lys Ala
                115                 120                 125

GCT GAG CTC GAT AGA GAA ATG GGA TTG ATT CGA ACT CAG GAA GAA ACC       613
Ala Glu Leu Asp Arg Glu Met Gly Leu Ile Arg Thr Gln Glu Glu Thr
            130                 135                 140

GGA AGG CAT GTG AGA ATG TTG ACT CAT GAG ATT AGA AGC ACT TTA GAT       661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA       709
Arg His Thr Ile Leu Lys Thr Thr Leu Val Glu Leu Gly Arg Thr Leu
    160                 165                 170

GCT TTG GAG GAG TGT GCA TTG TGG ATG CCT ACT AGA ACT GGG TTA GAG       757
Ala Leu Glu Glu Cys Ala Leu Trp Met Pro Thr Arg Thr Gly Leu Glu
175                 180                 185                 190

CTA CAG CTT TCT TAT ACA CTT CGT CAT CAA CAT CCC GTG GAG TAT ACG       805
Leu Gln Leu Ser Tyr Thr Leu Arg His Gln His Pro Val Glu Tyr Thr
                195                 200                 205

GTT CCT ATT CAA TTA CCG GTG ATT AAC CAA GTG TTT GGT ACT AGT AGG       853
Val Pro Ile Gln Leu Pro Val Ile Asn Gln Val Phe Gly Thr Ser Arg
            210                 215                 220

GCT GTA AAA ATA TCT CCT AAT TCT CCT GTG GCT AGG TTG AGA CCT GTT       901
Ala Val Lys Ile Ser Pro Asn Ser Pro Val Ala Arg Leu Arg Pro Val
```

-continued

```
        225                     230                     235

TCT GGG AAA TAT ATG CTA GGG GAG GTG GTC GCT GTG AGG GTT CCG CTT      949
Ser Gly Lys Tyr Met Leu Gly Glu Val Val Ala Val Arg Val Pro Leu
    240                     245                     250

CTC CAC CTT TCT AAT TTT CAG ATT AAT GAC TGG CCT GAG CTT TCA ACA      997
Leu His Leu Ser Asn Phe Gln Ile Asn Asp Trp Pro Glu Leu Ser Thr
255                     260                     265                 270

AAG AGA TAT GCT TTG ATG GTT TTG ATG CTT CCT TCA GAT AGT GCA AGG     1045
Lys Arg Tyr Ala Leu Met Val Leu Met Leu Pro Ser Asp Ser Ala Arg
                275                     280                     285

CAA TGG CAT GTC CAT GAG TTG GAA CTC GTT GAA GTC GTC GCT GAT CAG     1093
Gln Trp His Val His Glu Leu Glu Leu Val Glu Val Val Ala Asp Gln
            290                     295                     300

GTG GCT GTA GCT CTC TCA CAT GCT GCG ATC CTA GAA GAG TCG ATG CGA     1141
Val Ala Val Ala Leu Ser His Ala Ala Ile Leu Glu Glu Ser Met Arg
        305                     310                     315

GCT AGG GAC CTT CTC ATG GAG CAG AAT GTT GCT CTT GAT CTA GCT AGA     1189
Ala Arg Asp Leu Leu Met Glu Gln Asn Val Ala Leu Asp Leu Ala Arg
    320                     325                     330

CGA GAA GCA GAA ACA GCA ATC CGT GCC CGC AAT GAT TTC CTA GCG GTT     1237
Arg Glu Ala Glu Thr Ala Ile Arg Ala Arg Asn Asp Phe Leu Ala Val
335                     340                     345                 350

ATG AAC CAT GAA ATG CGA ACA CCG ATG CAT GCG ATT ATT GCA CTC TCT     1285
Met Asn His Glu Met Arg Thr Pro Met His Ala Ile Ile Ala Leu Ser
                355                     360                     365

TCC TTA CTC CAA GAA ACG GAA CTA ACC CCT GAA CAA AGA CTG ATG GTG     1333
Ser Leu Leu Gln Glu Thr Glu Leu Thr Pro Glu Gln Arg Leu Met Val
            370                     375                     380

GAA ACA ATA CTT AAA AGT AGT AAC CTT TTG GCA ACT TTG ATG AAT GAT     1381
Glu Thr Ile Leu Lys Ser Ser Asn Leu Leu Ala Thr Leu Met Asn Asp
        385                     390                     395

GTC TTA GAT CTT TCA AGG TTA GAA GAT GGA AGT CTT CAA CTT GAA CTT     1429
Val Leu Asp Leu Ser Arg Leu Glu Asp Gly Ser Leu Gln Leu Glu Leu
    400                     405                     410

GGG ACA TTC AAT CTT CAT ACA TTA TTT AGA GAG GTC CTC AAT CTG ATA     1477
Gly Thr Phe Asn Leu His Thr Leu Phe Arg Glu Val Leu Asn Leu Ile
415                     420                     425                 430

AAG CCT ATA GCG GTT GTT AAG AAA TTA CCC ATC ACA CTA AAT CTT GCA     1525
Lys Pro Ile Ala Val Val Lys Lys Leu Pro Ile Thr Leu Asn Leu Ala
                435                     440                     445

CCA GAT TTG CCA GAA TTT GTT GTT GGG GAT GAG AAA CGG CTA ATG CAG     1573
Pro Asp Leu Pro Glu Phe Val Val Gly Asp Glu Lys Arg Leu Met Gln
            450                     455                     460

ATA ATA TTA AAT ATA GTT GGT AAT GCT GTG AAA TTC TCC AAA CAA GGT     1621
Ile Ile Leu Asn Ile Val Gly Asn Ala Val Lys Phe Ser Lys Gln Gly
        465                     470                     475

AGT ATC TCC GTA ACC GCT CTT GTC ACC AAG TCA GAC ACA CGA GCT GCT     1669
Ser Ile Ser Val Thr Ala Leu Val Thr Lys Ser Asp Thr Arg Ala Ala
    480                     485                     490

GAC TTT TTT GTC GTG CCA ACT GGG AGT CAT TTC TAC TTG AGA GTG AAG     1717
Asp Phe Phe Val Val Pro Thr Gly Ser His Phe Tyr Leu Arg Val Lys
495                     500                     505                 510

GTA AAA GAC TCT GGA GCA GGA ATA AAT CCT CAA GAC ATT CCA AAG ATT     1765
Val Lys Asp Ser Gly Ala Gly Ile Asn Pro Gln Asp Ile Pro Lys Ile
                515                     520                     525

TTC ACT AAA TTT GCT CAA ACA CAA TCT TTA GCG ACG AGA AGC TCG GGT     1813
Phe Thr Lys Phe Ala Gln Thr Gln Ser Leu Ala Thr Arg Ser Ser Gly
            530                     535                     540

GGT AGT GGG CTT GGC CTC GCC ATC TCC AAG AGG TTT GTG AAT CTG ATG     1861
Gly Ser Gly Leu Gly Leu Ala Ile Ser Lys Arg Phe Val Asn Leu Met
```

-continued

```
          545                                         550                                         555

GAG  GGT  AAC  ATT  TGG  ATT  GAG  AGC  GAT  GGT  CTT  GGA  AAA  GGA  TGC  ACG        1909
Glu  Gly  Asn  Ile  Trp  Ile  Glu  Ser  Asp  Gly  Leu  Gly  Lys  Gly  Cys  Thr
     560                      565                           570

GCT  ATC  TTT  GAT  GTT  AAA  CTT  GGG  ATC  TCA  GAA  CGT  TCA  AAC  GAA  TCT        1957
Ala  Ile  Phe  Asp  Val  Lys  Leu  Gly  Ile  Ser  Glu  Arg  Ser  Asn  Glu  Ser
575                      580                      585                           590

AAA  CAG  TCG  GGC  ATA  CCG  AAA  GTT  CCA  GCC  ATT  CCC  CGA  CAT  TCA  AAT        2005
Lys  Gln  Ser  Gly  Ile  Pro  Lys  Val  Pro  Ala  Ile  Pro  Arg  His  Ser  Asn
                    595                      600                      605

TTC  ACT  GGA  CTT  AAG  GTT  CTT  GTC  ATG  GAT  GAG  AAC  GGG  GTA  AGT  AGA        2053
Phe  Thr  Gly  Leu  Lys  Val  Leu  Val  Met  Asp  Glu  Asn  Gly  Val  Ser  Arg
               610                      615                      620

ATG  GTG  ACG  AAG  GGA  CTT  CTT  GTA  CAC  CTT  GGG  TGC  GAA  GTG  ACC  ACG        2101
Met  Val  Thr  Lys  Gly  Leu  Leu  Val  His  Leu  Gly  Cys  Glu  Val  Thr  Thr
          625                      630                      635

GTG  AGT  TCA  AAC  GAG  GAG  TGT  CTC  CGA  GTT  GTG  TCC  CAT  GAG  CAC  AAA        2149
Val  Ser  Ser  Asn  Glu  Glu  Cys  Leu  Arg  Val  Val  Ser  His  Glu  His  Lys
     640                      645                      650

GTG  GTC  TTC  ATG  GAC  GTG  TGC  ATG  CCC  GGG  GTC  GAA  AAC  TAC  CAA  ATC        2197
Val  Val  Phe  Met  Asp  Val  Cys  Met  Pro  Gly  Val  Glu  Asn  Tyr  Gln  Ile
655                      660                      665                      670

GCT  CTC  CGT  ATT  CAC  GAG  AAA  TTC  ACA  AAA  CAA  CGC  CAC  CAA  CGG  CCA        2245
Ala  Leu  Arg  Ile  His  Glu  Lys  Phe  Thr  Lys  Gln  Arg  His  Gln  Arg  Pro
                    675                      680                      685

CTA  CTT  GTG  GCA  CTC  AGT  GGT  AAC  ACT  GAC  AAA  TCC  ACA  AAA  GAG  AAA        2293
Leu  Leu  Val  Ala  Leu  Ser  Gly  Asn  Thr  Asp  Lys  Ser  Thr  Lys  Glu  Lys
               690                      695                      700

TGC  ATG  AGC  TTT  GGT  CTA  GAC  GGT  GTG  TTG  CTC  AAA  CCC  GTA  TCA  CTA        2341
Cys  Met  Ser  Phe  Gly  Leu  Asp  Gly  Val  Leu  Leu  Lys  Pro  Val  Ser  Leu
          705                      710                      715

GAC  AAC  ATA  AGA  GAT  GTT  CTG  TCT  GAT  CTT  CTC  GAG  CCC  CGG  GTA  CTG        2389
Asp  Asn  Ile  Arg  Asp  Val  Leu  Ser  Asp  Leu  Leu  Glu  Pro  Arg  Val  Leu
     720                      725                      730

TAC  GAG  GGC  ATG  TAAAGGCGAT  GGATGCCCCA  TGCCCCAGAG  GAGTAATTCC                   2441
Tyr  Glu  Gly  Met
735

GCTCCCGCCT  TCTTCTCCCG  TAAAACATCG  GAAGCTGATG  TTCTCTGGTT  TAATTGTGTA          2501

CATATCAGAG  ATTGTCGGAG  CGTTTTGGAT  GATATCTTAA  AACAGAAAGG  GAATAACAAA          2561

ATAGAAACTC  TAAACCGGTA  TGTGTCCGTG  GCGATTTCGG  TTATAGAGGA  ACAAGATGGT          2621

GGTGGTATAA  TCATACCATT  TCAGATTACA  TGTTTGACTA  ATGTTGTATC  CTTATATATG          2681

TAGTTACATT  CTTATAAGAA  TTTGGATCGA  GTTATGGATG  CTTGTTGCGT  GCATGTATGA          2741

CATTGATGCA  GTATTATGGC  GTCAGCTTTG  CGCCGCTTAG  TAGAAC                          2787
```

( 2 ) INFORMATION FOR SEQ ID NO:9:

( i ) SEQUENCE CHARACTERISTICS:
( A ) LENGTH: 738 amino acids
( B ) TYPE: amino acid
( D ) TOPOLOGY: linear ( i i ) MOLECULE TYPE: protein ( x i ) SEQUENCE DESCRIPTION: SEQ ID NO:9:

```
Met  Glu  Val  Cys  Asn  Cys  Ile  Glu  Pro  Gln  Trp  Pro  Ala  Asp  Glu  Leu
 1                   5                       10                       15

Leu  Met  Lys  Tyr  Gln  Tyr  Ile  Ser  Asp  Phe  Phe  Ile  Ala  Ile  Val  Tyr
               20                       25                       30
```

-continued

Phe Ser Ile Pro Leu Glu Leu Ile Tyr Phe Val Lys Lys Ser Ala Val
35 40 45

Phe Pro Tyr Arg Trp Val Leu Val Gln Phe Gly Ala Phe Ile Val Leu
50 55 60

Cys Gly Ala Thr His Leu Ile Asn Leu Trp Thr Phe Thr Thr His Ser
65 70 75 80

Arg Thr Val Ala Leu Val Met Thr Thr Ala Lys Val Leu Thr Ala Val
85 90 95

Val Ser Cys Ala Thr Ala Leu Met Leu Val His Ile Ile Pro Asp Leu
100 105 110

Leu Ser Val Lys Thr Arg Glu Leu Phe Leu Lys Asn Lys Ala Ala Glu
115 120 125

Leu Asp Arg Glu Met Gly Leu Ile Arg Thr Gln Glu Glu Thr Gly Arg
130 135 140

His Val Arg Met Leu Thr His Glu Ile Arg Ser Thr Leu Asp Arg His
145 150 155 160

Thr Ile Leu Lys Thr Thr Leu Val Glu Leu Gly Arg Thr Leu Ala Leu
165 170 175

Glu Glu Cys Ala Leu Trp Met Pro Thr Arg Thr Gly Leu Glu Leu Gln
180 185 190

Leu Ser Tyr Thr Leu Arg His Gln His Pro Val Glu Tyr Thr Val Pro
195 200 205

Ile Gln Leu Pro Val Ile Asn Gln Val Phe Gly Thr Ser Arg Ala Val
210 215 220

Lys Ile Ser Pro Asn Ser Pro Val Ala Arg Leu Arg Pro Val Ser Gly
225 230 235 240

Lys Tyr Met Leu Gly Glu Val Val Ala Val Arg Val Pro Leu Leu His
245 250 255

Leu Ser Asn Phe Gln Ile Asn Asp Trp Pro Glu Leu Ser Thr Lys Arg
260 265 270

Tyr Ala Leu Met Val Leu Met Leu Pro Ser Asp Ser Ala Arg Gln Trp
275 280 285

His Val His Glu Leu Glu Leu Val Glu Val Val Ala Asp Gln Val Ala
290 295 300

Val Ala Leu Ser His Ala Ala Ile Leu Glu Glu Ser Met Arg Ala Arg
305 310 315 320

Asp Leu Leu Met Glu Gln Asn Val Ala Leu Asp Leu Ala Arg Arg Glu
325 330 335

Ala Glu Thr Ala Ile Arg Ala Arg Asn Asp Phe Leu Ala Val Met Asn
340 345 350

His Glu Met Arg Thr Pro Met His Ala Ile Ile Ala Leu Ser Ser Leu
355 360 365

Leu Gln Glu Thr Glu Leu Thr Pro Glu Gln Arg Leu Met Val Glu Thr
370 375 380

Ile Leu Lys Ser Ser Asn Leu Leu Ala Thr Leu Met Asn Asp Val Leu
385 390 395 400

Asp Leu Ser Arg Leu Glu Asp Gly Ser Leu Gln Leu Glu Leu Gly Thr
405 410 415

Phe Asn Leu His Thr Leu Phe Arg Glu Val Leu Asn Leu Ile Lys Pro
420 425 430

Ile Ala Val Val Lys Lys Leu Pro Ile Thr Leu Asn Leu Ala Pro Asp
435 440 445

Leu Pro Glu Phe Val Val Gly Asp Glu Lys Arg Leu Met Gln Ile Ile
450 455 460

-continued

```
Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met
```

( 2 ) INFORMATION FOR SEQ ID NO:10:

( i ) SEQUENCE CHARACTERISTICS:
( A ) LENGTH: 2787 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 188..2401

( x i ) SEQUENCE DESCRIPTION: SEQ ID NO:10:

```
AGTAAGAACG AAGAAGAAGT GTTAAACCCA ACCAATTTTG ACTTGAAAAA AAGCTTCAAC     60

GCTCCCCTTT TCTCCTTCTC CGTCGCTCTC CGCCGCGTCC CAAATCCCCA ATTCCTCCTC    120

TTCTCCGATC AATTCTTCCC AAGTGTGTGT ATGTGTGAGA GAGGAACTAT AGTGTAAAAA    180

ATTCATA ATG GAA GTC TGC AAT TGT ATT GAA CCG CAA TGG CCA GCG GAT      229
        Met Glu Val Cys Asn Cys Ile Glu Pro Gln Trp Pro Ala Asp
          1               5                  10
```

-continued

```
GAA TTG TTA ATG AAA TAC CAA TAC ATC TCC GAT TTC TTC ATT GCG ATT      277
Glu Leu Leu Met Lys Tyr Gln Tyr Ile Ser Asp Phe Phe Ile Ala Ile
15                  20                  25                  30

GCG TAT TTT TCG ATT CCT CTT GAG TTG ATT TAC TTT GTG AAG AAA TCA      325
Ala Tyr Phe Ser Ile Pro Leu Glu Leu Ile Tyr Phe Val Lys Lys Ser
                35                  40                  45

GCC GTG TTT CCG TAT AGA TGG GTA CTT GTT CAG TTT GGT GCT TTT TTC      373
Ala Val Phe Pro Tyr Arg Trp Val Leu Val Gln Phe Gly Ala Phe Phe
            50                  55                  60

GTT CTT TGT GGA GCA ACT CAT CTT ATT AAC TTA TGG ACT TTC ACT ACG      421
Val Leu Cys Gly Ala Thr His Leu Ile Asn Leu Trp Thr Phe Thr Thr
        65                  70                  75

CAT TCG AGA ACC GTG GCG CTT GTG ATG ACT ACC GCG AAG GTG TTA ACC      469
His Ser Arg Thr Val Ala Leu Val Met Thr Thr Ala Lys Val Leu Thr
    80                  85                  90

GCT GTT GTC TCG TGT GCT ACT GCG TTG ATG CTT GTT CAT ATT ATT CCT      517
Ala Val Val Ser Cys Ala Thr Ala Leu Met Leu Val His Ile Ile Pro
95                  100                 105                 110

GAT CTT TTG AGT GTT AAG ACT CGG GAG CTT TTC TTG AAA AAT AAA GCT      565
Asp Leu Leu Ser Val Lys Thr Arg Glu Leu Phe Leu Lys Asn Lys Ala
                115                 120                 125

GCT GAG CTC GAT AGA GAA ATG GGA TTG ATT CGA ACT CAG GAA GAA ACC      613
Ala Glu Leu Asp Arg Glu Met Gly Leu Ile Arg Thr Gln Glu Glu Thr
            130                 135                 140

GGA AGG CAT GTG AGA ATG TTG ACT CAT GAG ATT AGA AGC ACT TTA GAT      661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA      709
Arg His Thr Ile Leu Lys Thr Thr Leu Val Glu Leu Gly Arg Thr Leu
    160                 165                 170

GCT TTG GAG GAG TGT GCA TTG TGG ATG CCT ACT AGA ACT GGG TTA GAG      757
Ala Leu Glu Glu Cys Ala Leu Trp Met Pro Thr Arg Thr Gly Leu Glu
175                 180                 185                 190

CTA CAG CTT TCT TAT ACA CTT CGT CAT CAA CAT CCC GTG GAG TAT ACG      805
Leu Gln Leu Ser Tyr Thr Leu Arg His Gln His Pro Val Glu Tyr Thr
                195                 200                 205

GTT CCT ATT CAA TTA CCG GTG ATT AAC CAA GTG TTT GGT ACT AGT AGG      853
Val Pro Ile Gln Leu Pro Val Ile Asn Gln Val Phe Gly Thr Ser Arg
            210                 215                 220

GCT GTA AAA ATA TCT CCT AAT TCT CCT GTG GCT AGG TTG AGA CCT GTT      901
Ala Val Lys Ile Ser Pro Asn Ser Pro Val Ala Arg Leu Arg Pro Val
        225                 230                 235

TCT GGG AAA TAT ATG CTA GGG GAG GTG GTC GCT GTG AGG GTT CCG CTT      949
Ser Gly Lys Tyr Met Leu Gly Glu Val Val Ala Val Arg Val Pro Leu
    240                 245                 250

CTC CAC CTT TCT AAT TTT CAG ATT AAT GAC TGG CCT GAG CTT TCA ACA      997
Leu His Leu Ser Asn Phe Gln Ile Asn Asp Trp Pro Glu Leu Ser Thr
255                 260                 265                 270

AAG AGA TAT GCT TTG ATG GTT TTG ATG CTT CCT TCA GAT AGT GCA AGG     1045
Lys Arg Tyr Ala Leu Met Val Leu Met Leu Pro Ser Asp Ser Ala Arg
                275                 280                 285

CAA TGG CAT GTC CAT GAG TTG GAA CTC GTT GAA GTC GTC GCT GAT CAG     1093
Gln Trp His Val His Glu Leu Glu Leu Val Glu Val Val Ala Asp Gln
            290                 295                 300

GTG GCT GTA GCT CTC TCA CAT GCT GCG ATC CTA GAA GAG TCG ATG CGA     1141
Val Ala Val Ala Leu Ser His Ala Ala Ile Leu Glu Glu Ser Met Arg
        305                 310                 315

GCT AGG GAC CTT CTC ATG GAG CAG AAT GTT GCT CTT GAT CTA GCT AGA     1189
Ala Arg Asp Leu Leu Met Glu Gln Asn Val Ala Leu Asp Leu Ala Arg
    320                 325                 330
```

-continued

```
CGA GAA GCA GAA ACA GCA ATC CGT GCC CGC AAT GAT TTC CTA GCG GTT    1237
Arg Glu Ala Glu Thr Ala Ile Arg Ala Arg Asn Asp Phe Leu Ala Val
335                 340                 345                 350

ATG AAC CAT GAA ATG CGA ACA CCG ATG CAT GCG ATT ATT GCA CTC TCT    1285
Met Asn His Glu Met Arg Thr Pro Met His Ala Ile Ile Ala Leu Ser
                355                 360                 365

TCC TTA CTC CAA GAA ACG GAA CTA ACC CCT GAA CAA AGA CTG ATG GTG    1333
Ser Leu Leu Gln Glu Thr Glu Leu Thr Pro Glu Gln Arg Leu Met Val
            370                 375                 380

GAA ACA ATA CTT AAA AGT AGT AAC CTT TTG GCA ACT TTG ATG AAT GAT    1381
Glu Thr Ile Leu Lys Ser Ser Asn Leu Leu Ala Thr Leu Met Asn Asp
        385                 390                 395

GTC TTA GAT CTT TCA AGG TTA GAA GAT GGA AGT CTT CAA CTT GAA CTT    1429
Val Leu Asp Leu Ser Arg Leu Glu Asp Gly Ser Leu Gln Leu Glu Leu
    400                 405                 410

GGG ACA TTC AAT CTT CAT ACA TTA TTT AGA GAG GTC CTC AAT CTG ATA    1477
Gly Thr Phe Asn Leu His Thr Leu Phe Arg Glu Val Leu Asn Leu Ile
415                 420                 425                 430

AAG CCT ATA GCG GTT GTT AAG AAA TTA CCC ATC ACA CTA AAT CTT GCA    1525
Lys Pro Ile Ala Val Val Lys Lys Leu Pro Ile Thr Leu Asn Leu Ala
                435                 440                 445

CCA GAT TTG CCA GAA TTT GTT GTT GGG GAT GAG AAA CGG CTA ATG CAG    1573
Pro Asp Leu Pro Glu Phe Val Val Gly Asp Glu Lys Arg Leu Met Gln
            450                 455                 460

ATA ATA TTA AAT ATA GTT GGT AAT GCT GTG AAA TTC TCC AAA CAA GGT    1621
Ile Ile Leu Asn Ile Val Gly Asn Ala Val Lys Phe Ser Lys Gln Gly
        465                 470                 475

AGT ATC TCC GTA ACC GCT CTT GTC ACC AAG TCA GAC ACA CGA GCT GCT    1669
Ser Ile Ser Val Thr Ala Leu Val Thr Lys Ser Asp Thr Arg Ala Ala
    480                 485                 490

GAC TTT TTT GTC GTG CCA ACT GGG AGT CAT TTC TAC TTG AGA GTG AAG    1717
Asp Phe Phe Val Val Pro Thr Gly Ser His Phe Tyr Leu Arg Val Lys
495                 500                 505                 510

GTA AAA GAC TCT GGA GCA GGA ATA AAT CCT CAA GAC ATT CCA AAG ATT    1765
Val Lys Asp Ser Gly Ala Gly Ile Asn Pro Gln Asp Ile Pro Lys Ile
                515                 520                 525

TTC ACT AAA TTT GCT CAA ACA CAA TCT TTA GCG ACG AGA AGC TCG GGT    1813
Phe Thr Lys Phe Ala Gln Thr Gln Ser Leu Ala Thr Arg Ser Ser Gly
            530                 535                 540

GGT AGT GGG CTT GGC CTC GCC ATC TCC AAG AGG TTT GTG AAT CTG ATG    1861
Gly Ser Gly Leu Gly Leu Ala Ile Ser Lys Arg Phe Val Asn Leu Met
        545                 550                 555

GAG GGT AAC ATT TGG ATT GAG AGC GAT GGT CTT GGA AAA GGA TGC ACG    1909
Glu Gly Asn Ile Trp Ile Glu Ser Asp Gly Leu Gly Lys Gly Cys Thr
    560                 565                 570

GCT ATC TTT GAT GTT AAA CTT GGG ATC TCA GAA CGT TCA AAC GAA TCT    1957
Ala Ile Phe Asp Val Lys Leu Gly Ile Ser Glu Arg Ser Asn Glu Ser
575                 580                 585                 590

AAA CAG TCG GGC ATA CCG AAA GTT CCA GCC ATT CCC CGA CAT TCA AAT    2005
Lys Gln Ser Gly Ile Pro Lys Val Pro Ala Ile Pro Arg His Ser Asn
                595                 600                 605

TTC ACT GGA CTT AAG GTT CTT GTC ATG GAT GAG AAC GGG GTA AGT AGA    2053
Phe Thr Gly Leu Lys Val Leu Val Met Asp Glu Asn Gly Val Ser Arg
            610                 615                 620

ATG GTG ACG AAG GGA CTT CTT GTA CAC CTT GGG TGC GAA GTG ACC ACG    2101
Met Val Thr Lys Gly Leu Leu Val His Leu Gly Cys Glu Val Thr Thr
        625                 630                 635

GTG AGT TCA AAC GAG GAG TGT CTC CGA GTT GTG TCC CAT GAG CAC AAA    2149
Val Ser Ser Asn Glu Glu Cys Leu Arg Val Val Ser His Glu His Lys
    640                 645                 650
```

-continued

```
GTG GTC TTC ATG GAC GTG TGC ATG CCC GGG GTC GAA AAC TAC CAA ATC     2197
Val Val Phe Met Asp Val Cys Met Pro Gly Val Glu Asn Tyr Gln Ile
655                 660                 665                 670

GCT CTC CGT ATT CAC GAG AAA TTC ACA AAA CAA CGC CAC CAA CGG CCA     2245
Ala Leu Arg Ile His Glu Lys Phe Thr Lys Gln Arg His Gln Arg Pro
                675                 680                 685

CTA CTT GTG GCA CTC AGT GGT AAC ACT GAC AAA TCC ACA AAA GAG AAA     2293
Leu Leu Val Ala Leu Ser Gly Asn Thr Asp Lys Ser Thr Lys Glu Lys
            690                 695                 700

TGC ATG AGC TTT GGT CTA GAC GGT GTG TTG CTC AAA CCC GTA TCA CTA     2341
Cys Met Ser Phe Gly Leu Asp Gly Val Leu Leu Lys Pro Val Ser Leu
        705                 710                 715

GAC AAC ATA AGA GAT GTT CTG TCT GAT CTT CTC GAG CCC CGG GTA CTG     2389
Asp Asn Ile Arg Asp Val Leu Ser Asp Leu Leu Glu Pro Arg Val Leu
    720                 725                 730

TAC GAG GGC ATG TAAAGGCGAT GGATGCCCCA TGCCCCAGAG GAGTAATTCC         2441
Tyr Glu Gly Met
735

GCTCCCGCCT TCTTCTCCCG TAAAACATCG GAAGCTGATG TTCTCTGGTT TAATTGTGTA   2501

CATATCAGAG ATTGTCGGAG CGTTTTGGAT GATATCTTAA AACAGAAAGG GAATAACAAA   2561

ATAGAAACTC TAAACCGGTA TGTGTCCGTG GCGATTTCGG TTATAGAGGA ACAAGATGGT   2621

GGTGGTATAA TCATACCATT TCAGATTACA TGTTTGACTA ATGTTGTATC CTTATATATG   2681

TAGTTACATT CTTATAAGAA TTTGGATCGA GTTATGGATG CTTGTTGCGT GCATGTATGA   2741

CATTGATGCA GTATTATGGC GTCAGCTTTG CGCCGCTTAG TAGAAC                  2787
```

( 2 ) INFORMATION FOR SEQ ID NO:11:

( i ) SEQUENCE CHARACTERISTICS:
( A ) LENGTH: 738 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Met Glu Val Cys Asn Cys Ile Glu Pro Gln Trp Pro Ala Asp Glu Leu
 1               5                  10                  15

Leu Met Lys Tyr Gln Tyr Ile Ser Asp Phe Phe Ile Ala Ile Ala Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Phe Val Leu
    50                  55                  60

Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
```

-continued 165 170 175

Glu Glu Cys Ala Leu Trp Met Pro Thr Arg Thr Gly Leu Glu Leu Gln
180 185 190

Leu Ser Tyr Thr Leu Arg His Gln His Pro Val Glu Tyr Thr Val Pro
195 200 205

Ile Gln Leu Pro Val Ile Asn Gln Val Phe Gly Thr Ser Arg Ala Val
210 215 220

Lys Ile Ser Pro Asn Ser Pro Val Ala Arg Leu Arg Pro Val Ser Gly
225 230 235 240

Lys Tyr Met Leu Gly Glu Val Val Ala Val Arg Val Pro Leu Leu His
245 250 255

Leu Ser Asn Phe Gln Ile Asn Asp Trp Pro Glu Leu Ser Thr Lys Arg
260 265 270

Tyr Ala Leu Met Val Leu Met Leu Pro Ser Asp Ser Ala Arg Gln Trp
275 280 285

His Val His Glu Leu Glu Leu Val Glu Val Val Ala Asp Gln Val Ala
290 295 300

Val Ala Leu Ser His Ala Ala Ile Leu Glu Glu Ser Met Arg Ala Arg
305 310 315 320

Asp Leu Leu Met Glu Gln Asn Val Ala Leu Asp Leu Ala Arg Arg Glu
325 330 335

Ala Glu Thr Ala Ile Arg Ala Arg Asn Asp Phe Leu Ala Val Met Asn
340 345 350

His Glu Met Arg Thr Pro Met His Ala Ile Ile Ala Leu Ser Ser Leu
355 360 365

Leu Gln Glu Thr Glu Leu Thr Pro Glu Gln Arg Leu Met Val Glu Thr
370 375 380

Ile Leu Lys Ser Ser Asn Leu Leu Ala Thr Leu Met Asn Asp Val Leu
385 390 395 400

Asp Leu Ser Arg Leu Glu Asp Gly Ser Leu Gln Leu Glu Leu Gly Thr
405 410 415

Phe Asn Leu His Thr Leu Phe Arg Glu Val Leu Asn Leu Ile Lys Pro
420 425 430

Ile Ala Val Val Lys Lys Leu Pro Ile Thr Leu Asn Leu Ala Pro Asp
435 440 445

Leu Pro Glu Phe Val Val Gly Asp Glu Lys Arg Leu Met Gln Ile Ile
450 455 460

Leu Asn Ile Val Gly Asn Ala Val Lys Phe Ser Lys Gln Gly Ser Ile
465 470 475 480

Ser Val Thr Ala Leu Val Thr Lys Ser Asp Thr Arg Ala Ala Asp Phe
485 490 495

Phe Val Val Pro Thr Gly Ser His Phe Tyr Leu Arg Val Lys Val Lys
500 505 510

Asp Ser Gly Ala Gly Ile Asn Pro Gln Asp Ile Pro Lys Ile Phe Thr
515 520 525

Lys Phe Ala Gln Thr Gln Ser Leu Ala Thr Arg Ser Ser Gly Gly Ser
530 535 540

Gly Leu Gly Leu Ala Ile Ser Lys Arg Phe Val Asn Leu Met Glu Gly
545 550 555 560

Asn Ile Trp Ile Glu Ser Asp Gly Leu Gly Lys Gly Cys Thr Ala Ile
565 570 575

Phe Asp Val Lys Leu Gly Ile Ser Glu Arg Ser Asn Glu Ser Lys Gln
580 585 590

-continued

```
Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met
```

( 2 ) INFORMATION FOR SEQ ID NO:12:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

```
Gln Asn Val Ala Leu Asp Leu Ala Arg Arg Glu Ala Glu Thr Ala Ile
1               5                   10                  15

Arg Ala Arg Asn Asp Phe Leu Ala Val Met Asn His Glu Met Arg Thr
            20                  25                  30

Pro Met His Ala Ile Ile Ala Leu Ser Ser Leu Leu Gln Glu Thr Glu
        35                  40                  45

Leu Thr Pro Glu Gln Arg Leu Met Val Glu Thr Ile Leu Lys Ser Ser
    50                  55                  60

Asn Leu Leu Ala Thr Leu Met Asn Asp Val Leu Asp Leu Ser Arg Leu
65                  70                  75                  80

Glu Asp Gly Ser Leu Gln Leu Glu Leu Gly Thr Phe Asn Leu His Thr
                85                  90                  95

Leu Phe Arg Glu Val Leu Asn Leu Ile Lys Pro Ile Ala Val Val Lys
            100                 105                 110

Lys Leu Pro Ile Thr Leu Asn Leu Ala Pro Asp Leu Pro Glu Phe Val
        115                 120                 125

Val Gly Asp Glu Lys Arg Leu Met Gln Ile Ile Leu Asn Ile Val Gly
    130                 135                 140

Asn Ala Val Lys Phe Ser Lys Gln Gly Ser Ile
145                 150                 155
```

( 2 ) INFORMATION FOR SEQ ID NO:13:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Gln Asn Val Glu Leu Asp Leu Ala Lys Lys Arg Ala Gln Glu Ala Ala
1 5 10 15

Arg Ile Lys Ser Glu Phe Leu Ala Asn Met Ser His Glu Leu Arg Thr
20 25 30

Pro Leu Asn Gly Val Ile Gly Phe Thr Arg Leu Thr Leu Lys Thr Glu
35 40 45

Leu Thr Pro Thr Gln Arg Asp His Leu Asn Thr Ile Glu Arg Ser Ala
50 55 60

Asn Asn Leu Leu Ala Ile Ile Asn Asp Val Leu Asp Phe Ser Lys Leu
65 70 75 80

Glu Ala Gly Lys Leu Ile Leu Glu Ser Ile Pro Phe Pro Leu Arg Ser
85 90 95

Thr Leu Asp Glu Val Val Thr Leu Leu Ala His Ser Ser His Asp Lys
100 105 110

Gly Leu Glu Leu Thr Leu Asn Ile Lys Ser Asp Val Pro Asp Asn Val
115 120 125

Ile Gly Asp Pro Leu Arg Leu Gln Gln Ile Ile Thr Asn Leu Val Gly
130 135 140

Asn Ala Ile Lys Phe Thr Glu Asn Gly Asn Ile
145 150 155

( 2 ) INFORMATION FOR SEQ ID NO:14:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Gln Asn Ile Glu Leu Asp Leu Ala Arg Lys Glu Ala Leu Glu Ala Ser
1 5 10 15

Arg Ile Lys Ser Glu Phe Leu Ala Asn Met Ser His Glu Ile Arg Thr
20 25 30

Pro Leu Asn Gly Ile Leu Gly Phe Thr His Leu Leu Gln Lys Ser Glu
35 40 45

Leu Thr Pro Arg Gln Phe Asp Tyr Leu Gly Thr Ile Glu Lys Ser Ala
50 55 60

Asp Asn Leu Leu Ser Ile Ile Asn Glu Ile Leu Asp Phe Ser Lys Ile
65 70 75 80

Glu Ala Gly Lys Leu Val Leu Asp Asn Ile Pro Phe Asn Leu Arg Asp
85 90 95

Leu Leu Gln Asp Thr Leu Thr Ile Leu Ala Pro Ala Ala His Ala Lys
100 105 110

Gln Leu Glu Leu Val Ser Leu Val Tyr Arg Asp Thr Pro Leu Ala Leu
115 120 125

Ser Gly Asp Pro Leu Arg Leu Arg Gln Ile Leu Thr Asn Leu Val Ser
130 135 140

Asn Ala Ile Lys Phe Thr Arg Glu Gly Thr Ile
145 150 155

( 2 ) INFORMATION FOR SEQ ID NO:15:

( i ) SEQUENCE CHARACTERISTICS:
( A ) LENGTH: 149 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

```
Arg Ala Val Arg Glu Ala Arg His Ala Asn Gln Ala Lys Ser Arg Phe
1               5                   10                  15

Leu Ala Asn Met Ser His Glu Phe Arg Thr Pro Leu Asn Gly Leu Ser
            20                  25                  30

Gly Met Thr Glu Val Leu Ala Thr Thr Arg Leu Asp Ala Glu Gln Lys
        35                  40                  45

Glu Cys Leu Asn Thr Ile Gln Ala Ser Ala Arg Ser Leu Leu Ser Leu
    50                  55                  60

Val Glu Glu Val Leu Asp Ile Ser Ala Ile Glu Ala Gly Lys Ile Arg
65                  70                  75                  80

Ile Asp Arg Arg Asp Phe Ser Leu Arg Glu Met Ile Gly Ser Val Asn
                85                  90                  95

Leu Ile Leu Gln Pro Gln Ala Arg Gly Arg Arg Leu Glu Tyr Gly Thr
            100                 105                 110

Gln Val Ala Asp Asp Val Pro Asp Leu Leu Lys Gly Asp Thr Ala His
        115                 120                 125

Leu Arg Gln Val Leu Leu Asn Leu Val Gly Asn Ala Val Lys Phe Thr
    130                 135                 140

Glu His Gly His Val
145
```

( 2 ) INFORMATION FOR SEQ ID NO:16:

( i ) SEQUENCE CHARACTERISTICS:
( A ) LENGTH: 66 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

```
Leu Lys Val Leu Val Met Asp Glu Asn Gly Val Ser Arg Met Val Thr
1               5                   10                  15

Lys Gly Leu Leu Val His Leu Gly Cys Glu Val Thr Thr Val Ser Ser
            20                  25                  30

Asn Glu Glu Cys Leu Arg Val Val Ser His Glu His Lys Val Val Phe
        35                  40                  45

Met Asp Val Cys Met Pro Gly Val Glu Asn Tyr Gln Ile Ala Leu Arg
    50                  55                  60

Ile His
65
```

( 2 ) INFORMATION FOR SEQ ID NO:17:

( i ) SEQUENCE CHARACTERISTICS:
( A ) LENGTH: 67 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Leu Arg Val Leu Val Val Asp Asp His Lys Pro Asn Leu Met Leu Leu
1 5 10 15

Arg Gln Gln Leu Asp Tyr Leu Gly Gln Arg Val Val Ala Ala Asp Ser
20 25 30

Gly Glu Ala Ala Leu Ala Leu Trp His Glu His Ala Phe Asp Val Val
35 40 45

Ile Thr Asp Cys Asn Met Pro Gly Ile Asn Gly Tyr Glu Leu Ala Arg
50 55 60

Arg Ile Arg
65

( 2 ) INFORMATION FOR SEQ ID NO:18:

( i ) SEQUENCE CHARACTERISTICS:
( A ) LENGTH: 67 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

Met Met Ile Leu Val Val Asp Asp His Pro Ile Asn Arg Arg Leu Leu
1 5 10 15

Ala Asp Gln Leu Gly Ser Leu Gly Tyr Gln Cys Lys Thr Ala Asn Asp
20 25 30

Gly Val Asp Ala Leu Asn Val Leu Ser Lys Asn His Ile Asp Ile Val
35 40 45

Leu Ser Asp Val Asn Met Pro Asn Met Asp Gly Tyr Arg Leu Thr Gln
50 55 60

Arg Ile Arg
65

( 2 ) INFORMATION FOR SEQ ID NO:19:

( i ) SEQUENCE CHARACTERISTICS:
( A ) LENGTH: 67 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:19:

Pro Arg Val Leu Cys Val Asp Asp Asn Pro Ala Asn Leu Leu Leu Val
1 5 10 15

Gln Thr Leu Leu Glu Asp Met Gly Ala Glu Val Val Ala Val Glu Gly
20 25 30

Gly Tyr Ala Ala Val Asn Ala Val Gln Gln Glu Ala Phe Asp Leu Val
35 40 45

Leu Met Asp Val Gln Met Pro Gly Met Asp Gly Arg Gln Ala Thr Glu
50 55 60

Ala Ile Arg
65

( 2 ) INFORMATION FOR SEQ ID NO:20:

( i ) SEQUENCE CHARACTERISTICS:
( A ) LENGTH: 369 base pairs
( B ) TYPE: nucleic acid
( C ) STRANDEDNESS: single ( D ) TOPOLOGY: linear ( i i ) MOLECULE TYPE: cDNA ( x i ) SEQUENCE DESCRIPTION: SEQ ID NO:20:

ATGGAATCCT GTGATTGCAT TGAGGCTTTA CTGCCAACTG GTGACCTGCT GGTTAAATAC 60

CAATACCTCT CAGATTTCTT CATTGCTGTA GCCTACTTTT CCATTCCGTT GGAGCTTATT 120

TATTTTGTCC ACAAATCTGC ATGCTTCCCA TACAGATGGG TCCTCATGCA ATTTGGTGCT 180

TTTATTGTGC TCTGCGGAGC AACACACTTT ATTAGCTTGT GGACCTTCTT TATGCACTCT 240

AAGACGGTCG CTGTGGTTAT GACCATATCA AAAATGTTGA CAGCTGCCGT GTCCTGTATC 300

ACAGCTTTGA TGCTTGTTCA CATTATTCCT GATTTGCTAA GTGTTAAAAC GCGAGAGTTG 360

TTCTTGAAA 369

( 2 ) INFORMATION FOR SEQ ID NO:21:

( i ) SEQUENCE CHARACTERISTICS:
( A ) LENGTH: 369 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:21:

ATGGAAGTCT GCAATTGTAT TGAACCGCAA TGGCCAGCGG ATGAATTGTT AATGAAATAC 60

CAATACATCT CCGATTTCTT CATTGCGATT GCGTATTTTT CGATTCCTCT TGAGTTGATT 120

TACTTTGTGA AGAAATCAGC CGTGTTTCCG TATAGATGGG TACTTGTTCA GTTTGGTGCT 180

TTTATCGTTC TTTGTGGAGC AACTCATCTT ATTAACTTAT GGACTTTCAC TACGCATTCG 240

AGAACCGTGG CGCTTGTGAT GACTACCGCG AAGGTGTTAA CCGCTGTTGT CTCGTGTGCT 300

ACTGCGTTGA TGCTTGTTCA TATTATTCCT GATCTTTTGA GTGTTAAGAC TCGGGAGCTT 360

TTCTTGAAA 369

( 2 ) INFORMATION FOR SEQ ID NO:22:

( i ) SEQUENCE CHARACTERISTICS:
( A ) LENGTH: 296 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:22:

GCTCTTTCAC ATGCTGCAAT TTTAGAAGAT TCCATGCGAG CCCATGATCA GCTCATGGAA 60

CAGAATATTG CTTTGGATGT AGCTCGACAA GAAGCAGAGA TGGCCATCCG TGCACGTAAC 120

GACTTCCTTG CTGTGATGAA CCATGAAATG AGAACGCCCA TGCATGCAGT TATTGCTCTG 180

TGCTCTCTGC TTTTAGAAAC AGACTTAACT CCAGAGCAGA GAGTTATGAT TGAGACCATA 240

TTGAAGAGCA GCAATCTTCT TGCAACACTG ATAAATGATG TTCTAGATCT TTCTAG 296

( 2 ) INFORMATION FOR SEQ ID NO:23:

( i ) SEQUENCE CHARACTERISTICS:
( A ) LENGTH: 296 base pairs
( B ) TYPE: nucleic acid
( C ) STRANDEDNESS: single
( D ) TOPOLOGY: linear ( i i ) MOLECULE TYPE: cDNA (xi) SEQUENCE DESCRIPTION: SEQ ID NO:23:

```
GCTCTCTCAC ATGCTGCGAT CCTAGAAGAG TCGATGCGAG CTAGGGACCT TCTCATGGAG    60
CAGAATGTTG CTCTTGATCT AGCTAGACGA GAAGCAGAAA CAGCAATCCG TGCCCGCAAT   120
GATTTCCTAG CGGTTATGAA CCATGAAATG CGAACACCGA TGCATGCGAT TATTGCACTC   180
TCTTCCTTAC TCCAAGAAAC GGAACTAACC CCTGAACAAA GACTGATGGT GGAAACAATA   240
CTTAAAAGTA GTAACCTTTT GGCAACTTTG ATGAATGATG TCTTAGATCT TTCAAG       296
```

(2) INFORMATION FOR SEQ ID NO:24:

(i) SEQUENCE CHARACTERISTICS:
(A) LENGTH: 123 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:24:

```
Met Glu Ser Cys Asp Cys Ile Glu Ala Leu Leu Pro Thr Gly Asp Leu
1               5                   10                  15

Leu Val Lys Tyr Gln Tyr Leu Ser Asp Phe Phe Ile Ala Val Ala Tyr
            20                  25                  30

Phe Ser Ile Pro Leu Glu Leu Ile Tyr Phe Val His Lys Ser Ala Cys
        35                  40                  45

Phe Pro Tyr Arg Trp Val Leu Met Gln Phe Gly Ala Phe Ile Val Leu
    50                  55                  60

Cys Gly Ala Thr His Phe Ile Ser Leu Trp Thr Phe Phe Met His Ser
65                  70                  75                  80

Lys Thr Val Ala Val Val Met Thr Ile Ser Lys Met Leu Thr Ala Ala
                85                  90                  95

Val Ser Cys Ile Thr Ala Leu Met Leu Val His Ile Ile Pro Asp Leu
            100                 105                 110

Leu Ser Val Lys Thr Arg Glu Leu Phe Leu Lys
        115                 120
```

(2) INFORMATION FOR SEQ ID NO:25:

(i) SEQUENCE CHARACTERISTICS:
(A) LENGTH: 123 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:25:

```
Met Glu Val Cys Asn Cys Ile Glu Pro Gln Trp Pro Ala Asp Glu Leu
1               5                   10                  15

Leu Met Lys Tyr Gln Tyr Ile Ser Asp Phe Phe Ile Ala Ile Ala Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Ile Val Leu
    50                  55                  60

Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95
```

Val Ser Cys Ala Thr Ala Leu Met Leu Val His Ile Ile Pro Asp Leu
100 105 110

Leu Ser Val Lys Thr Arg Glu Leu Phe Leu Lys
115 120

( 2 ) INFORMATION FOR SEQ ID NO:26:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:26:

AGTAAGAACG AAGAAGAAGT G 21

( 2 ) INFORMATION FOR SEQ ID NO:27:

( i ) SEQUENCE CHARACTERISTICS:
( A ) LENGTH: 56 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:27:

Leu Arg Val Lys Val Lys Asp Ser Gly Ala Gly Ile Asn Pro Gln Asp
1 5 10 15

Ile Pro Lys Ile Phe Thr Lys Phe Ala Gln Thr Gln Ser Leu Ala Thr
20 25 30

Arg Ser Ser Gly Gly Ser Gly Leu Gly Leu Ala Ile Ser Lys Arg Phe
35 40 45

Val Asn Leu Met Glu Gly Asn Ile
50 55

( 2 ) INFORMATION FOR SEQ ID NO:28:

( i ) SEQUENCE CHARACTERISTICS:
( A ) LENGTH: 56 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

Ile Glu Val Gln Ile Arg Asp Thr Gly Ile Gly Ile Pro Glu Arg Asp
1 5 10 15

Gln Ser Arg Leu Phe Gln Ala Phe Arg Gln Ala Asp Ala Ser Ile Ser
20 25 30

Arg Arg His Gly Gly Thr Gly Leu Gly Leu Val Ile Thr Gln Lys Leu
35 40 45

Val Asn Glu Met Gly Gly Asp Ile
50 55

( 2 ) INFORMATION FOR SEQ ID NO:29:

( i ) SEQUENCE CHARACTERISTICS:
( A ) LENGTH: 56 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:29:

Leu Arg Ile Ser Val Gln Asp Thr Gly Ile Gly Leu Ser Ser Gln Asp
1 5 10 15

Val Arg Ala Leu Phe Gln Ala Phe Ser Gln Ala Asp Asn Ser Leu Ser
20 25 30

Arg Gln Pro Gly Gly Thr Gly Leu Gly Leu Val Ile Ser Lys Arg Leu
35 40 45

Ile Glu Gln Met Gly Gly Glu Ile
50 55

( 2 ) INFORMATION FOR SEQ ID NO:30:

( i ) SEQUENCE CHARACTERISTICS:
( A ) LENGTH: 56 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:30:

Leu Arg Phe Asp Val Glu Asp Thr Gly Ile Gly Val Pro Met Asp Met
1 5 10 15

Arg Pro Arg Leu Phe Glu Ala Phe Glu Gln Ala Asp Val Gly Leu Ser
20 25 30

Arg Arg Tyr Glu Gly Thr Gly Leu Gly Thr Thr Ile Ala Lys Gly Leu
35 40 45

Val Glu Ala Met Gly Gly Ser Ile
50 55

( 2 ) INFORMATION FOR SEQ ID NO:31:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:31:

Pro Leu Leu Val Ala Leu Ser Gly Asn Thr Asp Lys Ser Thr Lys Glu
1 5 10 15

Lys Cys Met Ser Phe Gly Leu Asp Gly Val Leu Leu Lys Pro Val Ser
20 25 30

Leu Asp Asn Ile Arg Asp Val Leu Ser Asp Leu Leu
35 40

( 2 ) INFORMATION FOR SEQ ID NO:32:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:32:

Cys Ile Leu Phe Gly Phe Thr Ala Ser Ala Gln Met Asp Glu Ala His
1 5 10 15

-continued

Ala Cys Arg Ala Ala Gly Met Asp Asp Cys Leu Phe Lys Pro Ile Gly
20 25 30

Val Asp Ala Leu Arg Gln Arg Leu Asn Glu Ala Ala
35 40

( 2 ) INFORMATION FOR SEQ ID NO:33:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

Leu Pro Val Ile Gly Val Thr Ala Asn Ala Leu Ala Glu Glu Lys Gln
1 5 10 15

Arg Cys Leu Glu Ser Gly Met Asp Ser Cys Leu Ser Lys Pro Val Thr
20 25 30

Leu Asp Val Ile Lys Gln Ser Leu Thr Leu Tyr Ala
35 40

( 2 ) INFORMATION FOR SEQ ID NO:34:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:34:

Leu Pro Ile Val Ala Leu Thr Ala His Ala Met Ala Asn Glu Lys Arg
1 5 10 15

Ser Leu Leu Gln Ser Gly Met Asp Asp Tyr Leu Thr Lys Pro Ile Ser
20 25 30

Glu Arg Gln Leu Ala Gln Val Val Leu Lys Trp Thr
35 40

PLANTS HAVING MODIFIED RESPONSE TO ETHYLENE

This is a continuation of application Ser. No. 08/086,555 filed Jul. 1, 1993 now abandoned.

The U.S. Government has certain rights in this invention pursuant to Department of Energy Contract No. DE-FG03-88ER13873.

TECHNICAL FIELD OF THE INVENTION

The invention generally relates to modified ETR nucleic acid and plants transformed with such nucleic acid which have a phenotype characterized by a decrease in the normal response to ethylene.

BACKGROUND OF THE INVENTION

Ethylene has been recognized as a plant hormone since the turn of the century when its effect on pea seedling development was first described. Neljubow (1901), *Pflanzen Beih. Bot. Zentralb.* 10:128–139. Since then, numerous reports have appeared which demonstrate that ethylene is an endogenous regulator of growth and development in higher plants. For example, ethylene has been implicated in seed dormancy, seedling growth, flower initiation, leaf abscission, senescence and fruit ripening. Ethylene is a plant hormone whose biosynthesis is induced by environmental stress such as oxygen deficiency, wounding, pathogen invasion and flooding.

Recently, genes encoding some of the enzymes involved in ethylene biosynthesis have been cloned. Sato, et al. (1989) *Proc. Natl. Acad. Sci. USA* 86:6621–6625; Nakajima, et al. (1990) *Plant Cell Phys. Physiol.* 29:989–996; Van Der Straeten, et al. (1990) *Proc. Natl. Acad. Sci U.S.A.* 87:4859–4963; Hamilton, et al. (1991) *Proc. Natl. Acad. Sci. U.S.A.* 88:7434–7437; and Spanu, et al. (1991) *EMBO J.* 10:2007–2013. The pathway for ethylene biosynthesis is shown in FIG. 1. As can be seen the amino acid methionine is converted to S-adenosyl-methionine (SAM) by SAM synthetase which in turn is converted to 1-aminocyclopropane-1-carboxylic acid (ACC) by ACC synthase. Adams, et al. (1979) *Proc. Natl. Acad. Sci. U.S.A.* 76:170–174. The ACC is then converted to ethylene by way of the enzyme ACC oxidase. Yang, et al. (1984) *Annu. Rev. Plant. Physiol.* 35:155–189.

A number of approaches have been taken in an attempt to control ethylene biosynthesis to thereby control fruit ripening. Oeller, et al. (1991) *Science* 254:437–439 report that expression of an antisense RNA to ACC synthase inhibits fruit ripening in tomato plants. Hamilton, et al. (1990) *Nature* 346:284–287 report the use of an antisense TOM13 (ACC oxidase) gene in transgenic plants. Picton et al. (1993) *Plant Journal* 3:469–481, report altered fruit ripening and leaf senesence in tomatoes expressing an antisense ethylene-forming enzyme.

In a second approach, ethylene biosynthesis was reportedly modulated by expressing an ACC deaminase in plant tissue to lower the level of ACC available for conversion to ethylene. See PCT publication No. WO92/12249 published Jul. 23, 1992, and Klee et al. (1991) *Plant Cell* 3:1187–1193.

While a substantial amount of information has been gathered regarding the biosynthesis of ethylene, very little is known about how ethylene controls plant development. Although several reports indicate that a high affinity binding site for ethylene is present in plant tissues, such receptors have not been identified. Jerie, et al. (1979) *Planta* 144:503; Sisler (1979) *Plant Physiol.* 64:538; Sisler, et al. (1990) *Plant Growth Reg.* 9:157–164, and Sisler (1990) "Ethylene-Binding Component in Plants", *The Plant Hormone Ethylene.*, A. K. Mattoo and J. C. Suttle, eds. (Boston) C.R.C. Press, Inc., pp. 81–90. In Arabidopsis, several categories of mutants have been reported. In the first two categories, mutants were reported which produce excess ethylene or reduced ethylene as compared to the wild-type. Guzman, et al. (1990) *The Plant Cell* 2:513–523. In a third category, mutants failed to respond to ethylene. Id.; Bleecker, et al. (1988) *Science* 241:1086–1089, Harpham, et al. (1991) *Ann. of Botany* 68:55–61. The observed insensitivity to ethylene was described as being either a dominant or recessive mutation. Id.

Based upon the foregoing, it is clear that the genetic basis and molecular mechanism of ethylene interaction with plants has not been clearly delineated. Given the wide range of functions regulated by ethylene and the previous attempts to control ethylene function by regulating its synthesis, it would be desirable to have an alternate approach to modulate growth and development in various plant tissues such as fruits, vegetables and flowers by altering the interaction of ethylene with plant tissue.

Accordingly, it is an object of the invention to provide isolated nucleic acids comprising an ethylene response (ETR) nucleic acid.

In addition, it is an object to provide modifications to such ETR nucleic acids to substitute, insert and/or delete one or more nucleotides so as to substitute, insert and/or delete one or more amino acid residues in the protein encoded by the ETR nucleic acid.

Still further, it is an object to provide plant cells transformed with one or more modified ETR nucleic acids. Such transformed plant cells can be used to produce transformed plants wherein the phenotype vis-a-vis the response of one or more tissues of the plant to ethylene is modulated.

SUMMARY OF THE INVENTION

In accordance with the foregoing objects, the invention includes transformed plants having at least one cell transformed with a modified ETR nucleic acid. Such plants have a phenotype characterized by a decrease in the response of at least one transformed plant cell to ethylene as compared to a plant not containing the transformed plant cell.

The invention also includes vectors capable of transforming a plant cell to alter the response to ethylene. In one embodiment, the vector comprises a modified ETR nucleic acid which causes a decrease in cellular response to ethylene. Tissue and/or temporal specificity for expression of the modified ETR nucleic acid is controlled by selecting appropriate expression regulation sequences to target the location and/or time of expression of the transformed nucleic acid.

The invention also includes methods for producing plants having a phenotype characterized by a decrease in the response of at least one transformed plant cell to ethylene as compared to a wild-type plant not containing such a transformed cell. The method comprises transforming at least one plant cell with a modified ETR nucleic acid, regenerating plants from one or more of the transformed plant cells and selecting at least one plant having the desired phenotype.

BRIEF DESCRIPTION OF THE DRAWINGS

FIGS. 2A, 2B and 2C depict the genomic nucleic acid sequence (Sequence ID No. 1) for the ETR gene from *Arabidopsis thaliana*.

FIGS. 3A, 3B, 3C and 3D depict the cDNA nucleic acid (Sequence ID No. 2) and deduced amino acid sequence (Sequence ID No. 3) for the ETR gene from *Arabidopsis thaliana.*

FIGS. 4A, 4B, 4C and 4D through FIGS. 7A, 7B, 7C and 7D depict the cDNA and deduced amino acid sequence for four mutant ETR genes from *Arabidopsis thaliana* which confer ethylene insensitivity. Each sequence differs from the wild type sequence set forth in FIG. 3 by substitution of one amino acid residue. The etr1-3 (formerly ein1-1) mutation in FIGS. 4A–4D (Sequence ID Nos. 8 and 9) comprises the substitution of alanine-31 with valine. The ert1-4 mutation in FIGS. 5A–5D (Sequence ID Nos. 10 and 11) comprises the substitution of isoleucine-62 with phenylalanine. The etr1-1 (formerly etr) mutation in FIGS. 6A–6D (Sequence ID Nos. 4 and 5) comprises the substitution of cysteine-65 with tyrosine. The etr1-2 mutation in FIGS. 7A–7D (Sequence ID Nos. 6 and 7) comprises the substitution of alanine-102 with threonine.

FIGS. 9A and 9B the amino acid sequence alignments of the predicted ETR1 protein and the conserved domains of several bacterial histidine kinases and response regulators. Amino acids are shown in boldface type at positions where there are at least two identities with ETR1. In FIG. 9A, the deduced ETR1 amino acid sequence SEQ ID NOS:12 and 27 (residues 326 to 562) aligned with the histidine kinase domains of *E. coli* BarA SEQ ID NOS:13 and 28, *P. Syringae* LemA SEQ ID NOS:14 and 29 and *X. campestris* RpfC SEQ ID NOS:15 and 30. Boxes surround the five conserved motifs characteristic of the bacterial histidine kinase domain as compiled by Parkinson and Kofoid (Parkinson et al. (1992) *Annu. Rev. Genet.* 26:71). The conserved histidine residue that is the supposed site of autophosphorylation is indicated by an asterisk. Numbers and positions of amino acids not shown are given in parentheses. In FIG. 9B, the deduced ETR1 amino acid sequence (residues 610 to 729) SEQ ID NOS:15 and 31 are aligned with the response regulator domains of *B. parapertussis* BvgS SEQ ID NOS:17 and 32, *P. syringae* LemA SEQ ID NOS:19 and 34 and *E. coli* RscC SEQ ID NOS:18 and 33. Amino acids are shown in boldface type where there are at least two identities with ETR1. Boxes surround the four highly conserved residues in bacterial response regulators. The conserved aspartate residue that is the site of phosphorylation is indicated by an asterisk. Numbers and positions of amino acids not shown are given in parentheses. For alignment purposes, a gap (_) was introduced in the ETR1 sequence.

FIGS. 10A and 10B depict specific DNA sequences for ETR nucleic acids from tomato and *Arabidopsis thaliana.* FIG. 10A compares the DNA sequence encoding amino acid residues 1 through 123 (Sequence ID Nos. 20 and 21). FIG. 10B compares the ETR nucleic acid sequence encoding amino acids 306 through 403 (Sequence ID Nos. 22 and 23). The vertical lines in each figure identify homologous nucleotides.

FIGS. 11A and 11B compare partial amino acid sequences (using single letter designation) for an ETR protein from tomato and *Arabidopsis thaliana.* FIG. 11A compares the amino acid sequence for the ETR protein for amino acids 1 through 123. FIG. 11B compares the amino acid sequence for the ETR protein for residues 306 through 403 SEQ ID NOS:26 and 27. The vertical lines indicate exact sequence homology. Two vertical dots indicate that the amino acid residues are functionally conserved. One dot indicates weak functional conservation as between amino acid residues.

DETAILED DESCRIPTION

Figure 1:
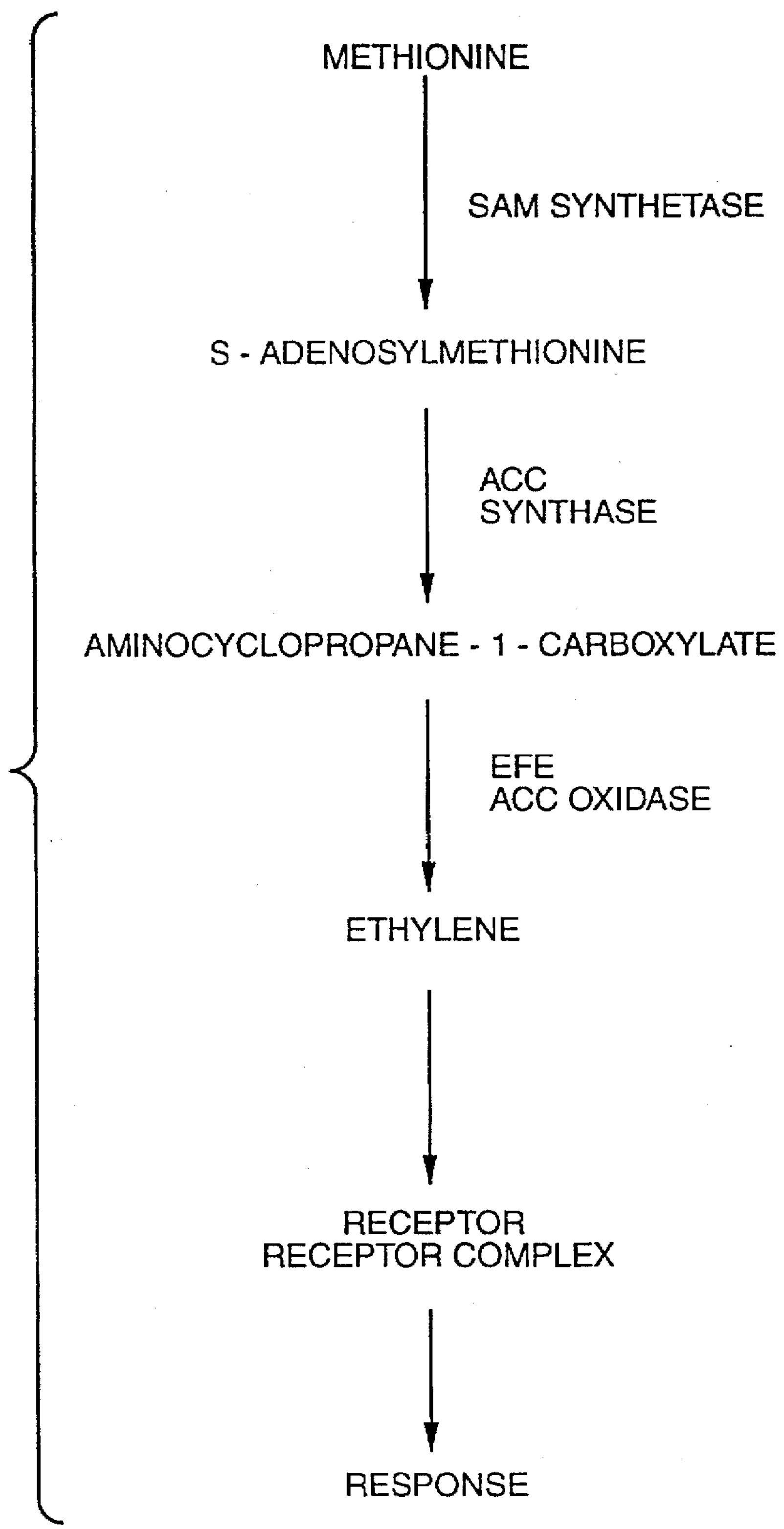
FIG. 1 depicts the biosynthetic pathway for ethylene.

The invention provides, in part, plants having cells transformed with a vector comprising an ETR nucleic acid or a modified ETR nucleic acid. Such transformed plant cells have a modulated response to ethylene. In a preferred embodiment, the expression of a modified ETR nucleic acid confers a phenotype on the plant characterized by a decrease in the response to ethylene for at least for those cells expressing the modified ETR nucleic acid as compared to a corresponding non-transformed plant. Thus, for example, when the modified ETR nucleic acid is expressed in fruit such as tomato, the fruit ripening process is retarded thereby reducing spoilage and extending the shelf life and/or harvesting season for the fruit. The invention is similarly useful to prevent spoilage of vegetative tissue and to enhance the longevity of cut flowers.

As used herein, a "plant ETR nucleic acid" refers to nucleic acid encoding all or part of a "plant ETR protein". ETR nucleic acids can initially be identified by homology to the ETR nucleic acid sequences disclosed herein. ETR nucleic acids, however, are also defined functionally by their ability to confer a modulated ethylene response upon transformation into plant tissue. For example, an antisense construct of an ETR nucleic acid or modified ETR nucleic acid is capable of reducing the ethylene response in plant tissue expressing the antisense ETR nucleic acid. In addition, transformation with an ETR nucleic acid or modified ETR nucleic acid can result in co-suppression of the endogenous ETR alleles which in turn modifies the ethylene response. Furthermore, ETR nucleic acids can be modified as described herein to produce modified ETR nucleic acids which when used to transform plant tissue result in varying degrees of ethylene insensitivity in the tissue expressing such modified ETR nucleic acids. When evaluating a putative ETR nucleic acid for the ability of a modified form of the ETR nucleic acid to confer ethylene insensitivity, it is preferred that a codon or combination of codons encoding the amino acid residues equivalent to Ala-31, Ile-62, Cys-65 or Tyr-102 in the ETR protein of *Arabidopsis thaliana* be modified so as to substitute a different amino acid residue such as those disclosed herein for the specified residues.

Plant ETR nucleic acids include genomic DNA, cDNA and oligonucleotides including sense and anti-sense nucleic acids as well as RNA transcripts thereof. The genomic DNA sequence (Sequence ID No. 1) for the ETR1 gene from *Arabidopsis thaliana* is shown in FIG. 2. The corresponding cDNA sequence (Sequence ID No. 2) and deduced ETR amino acid sequence (Sequence ID No. 3) are shown in FIG. 3. An amino terminal domain (i.e., resides 1 through about 313) of the predicted ETR protein sequence has no homology to known protein sequences. Approximately midway in the ETR protein (i.e., residues 295 through 313) is a putative transmembrane domain followed by a putative intracellular domain (i.e., residues 314 through 738). This putative intracellular domain unexpectedly has sequence homology to the two component environmental sensor-regulators known in bacteria. These two families in bacteria form a conserved sensor-regulator system that allows the bacteria to respond to a broad range of environmental fluctuations. It is believed that the amino terminal portion of the ETR protein interacts either directly with ethylene or indirectly (e.g., with an ethylene binding protein or another protein) and that upon such interaction, signal transduction through the intracellular domain occurs.

An ETR nucleic acid or ETR protein is initially identified by substantial nucleic acid and/or amino acid sequence homology to the sequences shown in FIGS. 2 and 3. Such homology can be based upon the overall nucleic acid or amino acid sequence in which case the overall homology of the protein sequence is preferably greater than 60%, more preferably greater than 75% and most preferably greater than 90% homologous. It is preferred, however, that the unique amino-terminal portion of the ETR protein sequence or the nucleic acid sequence encoding this portion of the molecule (i.e., the 5' terminal portion) be used to identify an ETR protein or ETR nucleic acid. When using this amino terminal sequence portion, it is preferred that the amino acid sequence homology be greater than about 70%, more preferably greater than 85% and most preferably greater than 95% homologous. Homology based on nucleic acid sequence is commensurate with amino acid homology but takes into account the degeneracy in the genetic code and codon bias in different plants. Accordingly, the nucleic acid sequence homology may be substantially lower than that based on protein sequence. Thus, an ETR protein is any protein which has an amino-terminal portion which is substantially homologous to the amino-terminal domain of the ETR protein from *Arabidopsis thaliana*. An ETR nucleic acid by analogy also encodes at least this amino-terminal domain.

An ETR nucleic acid from a plant species other than *Arabidopsis thaliana* can be readily identified by standard methods utilizing a known ETR nucleic acid. For example, labelled probes corresponding to a known ETR nucleic acid or encoding the unique amino-terminal domain can be used for in situ hybridization to detect the presence of an ETR gene in a particular plant species. In addition, such probes can be used to screen genomic or cDNA libraries of a different plant species or to identify one or more bands containing all or part of an ETR gene by hybridization to an electrophoretically separated preparation of genomic DNA digested with one or more restriction endonucleases.

The hybridization conditions will vary depending upon the probe used. When a unique nucleotide sequence of an ETR nucleic acid is used, e.g., an oligonucleotide encoding all or part of the amino terminal domain, relatively high stringency, e.g., about 0.1×SSPE at 65° C. is used. When the hybridization probe covers a region which has a potentially lower sequence homology to known ETR nucleic acids, e.g., a region covering a portion of the unique amino terminal domain and a portion covering a transmembrane domain, the hybridization is preferably carried out under moderate stringency conditions, e.g., about 5×SSPE at 50° C.

For example, using the above criteria, a ripening tomato cDNA library (Stratagene, LaJolla, Calif., Catalog No. 936004) was screened with a labeled probe comprising the nucleic acid sequence encoding residues 1 through 300 of the Arabidopsis ETR protein sequence disclosed herein in FIGS. 3A, B, C and D. Several clones were identified and sequenced by standard techniques. The DNA sequences for the ETR nucleic acid from tomato and *Arabidopsis thaliana* encoding amino acid residues 1 through 123 (Sequence ID Nos. 20 and 21) and amino acids 306 through 403 (Sequence ID Nos. 22 and 23) are set forth in FIGS. 10A and 10B, respectively.

The amino acid sequences for the ETR protein from *Arabidopsis thaliana* and tomato for residues 1 through 123 (Sequence ID Nos. 25 and 24) and 306 through 403 (Sequence ID Nos. 27 and 26) are set forth in FIGS. 11A and 11B, respectively.

As can be seen, there is substantial homology between the Arabidopsis and the tomato ETR sequences both on the level of DNA sequence and amino acid sequence. In particular, the homology on the DNA level for the sequence encoding amino acids 1 through 45 is slightly greater than 72%. The homology on the amino acid level for amino acid residues 1 through 123 is approximately 79%. In the case of amino acid sequence homology, when the differences between the amino acids at equivalent residues are compared and such differences comprise the substitution of a conserved residue, i.e., amino acid residues which are functionally equivalent, the amino acid sequence similarity rises to about 90%. Such sequence similarity was determined using a Best Fit sequence program as described by Devereux et al. (1984) *Nucl. Acids Res.* 12:387–395. Functionally equivalent (i.e., conserved) residues are identified by double and single data in the comparative sequences. Similarly, the nucleic acid sequence homology between Arabidopsis and tomato for the sequence encoding amino acid residues 306 to 403 is approximately 75%. The sequence homology on the amino acid level for identical amino acids is almost 86% whereas the similarity is almost 96%.

As described hereinafter, substitution of amino acid residues Ala-31, Ile-62, Cys-65 and Tyr-102 with a different amino acid results in modified Arabidopsis ETR nucleic acid which are capable of conferring ethylene insensitivity in a transformed plant. Each of these residues are identical as between the ETR protein of tomato and *Arabidopsis thaliana*.

Once the ETR nucleic acid is identified, it can be cloned and, if necessary, its constituent parts recombined to form the entire ETR nucleic acid. Once isolated from its natural source, e.g., contained within a plasmid or other vector or excised therefrom as a linear nucleic acid segment, the ETR nucleic acid can be further used as a probe to identify and isolate other ETR nucleic acids. It can also be used as a "precursor" nucleic acid to make modified ETR nucleic acids and proteins.

As used herein, the term "modified ETR nucleic acid" refers to an ETR nucleic acid containing the substitution, insertion or deletion of one or more nucleotides of a precursor ETR nucleic acid. The precursor ETR nucleic acids include naturally-occurring ETR nucleic acids as well as other modified ETR nucleic acids. The naturally-occurring ETR nucleic acid from *Arabidopsis thaliana* can be used as a precursor nucleic acid which can be modified by standard techniques, such as site-directed mutagenesis, cassette mutagenesis and the like, to substitute one or more nucleotides at a codon such as that which encodes alanine at residue 31 in the Arabidopsis ETR nucleic acid. Such in vitro codon modification can result in the generation of a codon at position 31 which encodes any one of the other naturally occurring amino acid residues. Such modification results in a modified ETR nucleic acid.

Alternatively, the precursor nucleic acid can be one wherein one or more of the nucleotides of a wild-type ETR nucleic acid have already been modified. Thus, for example, the *Arabidopsis thaliana* ETR nucleic acid can be modified at codon 31 to form a modified nucleic acid containing the substitution of that codon with a codon encoding an amino acid other than alanine, e.g., valine. This modified ETR nucleic acid can also act as a precursor nucleic acid to introduce a second modification. For example, the codon encoding Ala-102 can be modified to encode the substitution of threonine in which case the thus formed modified nucleic acid encodes the substitution of two different amino acids at residues 31 and 102.

Deletions within the ETR nucleic acid are also contemplated. For example, an ETR nucleic acid can be modified to delete that portion encoding the putative transmembrane in intracellular domains. The thus formed modified ETR nucleic acid when expressed within a plant cell produces only the amino-terminal portion of the ETR protein which is potentially capable of binding ethylene, either directly or indirectly, to modulate the effective level of ethylene in plant tissue.

In addition, the modified ETR nucleic acid can be identified and isolated from a mutant plant having a dominant or recessive phenotype characterized by an altered response to ethylene. Such mutant plants can be spontaneously arising or can be induced by well known chemical or radiation mutagenesis techniques followed by the determination of the ethylene response in the progeny of such plants. Examples of such mutant plants which occur spontaneously include the Never ripe mutant of tomato and the ethylene insensitive mutant of carnation. Thus, modified ETR nucleic acids can be obtained by recombinant modification of wild-type ETR nucleic acids or by the identification and isolation of modified ETR alleles from mutant plant species.

It is preferred that the modified ETR nucleic acid encode the substitution, insertion and/or deletion of one or more amino acid residues in the precursor ETR protein. Upon expression of the modified nucleic acid in host plant cells, the modified ETR protein thus produced is capable of modulating at least the host cell's response to ethylene. In connection with the generation of such a phenotype, a number of codons have been identified in the ETR nucleic acid from *Arabidopsis thaliana* which when modified and reintroduced into a wild-type plant result in a decrease in the ethylene response by the transformed plant. These codons encode amino acid residues Ala-31, Ile-62, Cys-65 and Tyr-102 in the ETR protein of *Arabidopsis thaliana*. The ETR gene and each of these particular modified amino acid residues were identified by cloning the wild-type ETR gene from *Arabidopsis thaliana* and chemically modified alleles from four different varieties (etr1-1, etr1-2, etr1-3 and etr1-4) of *Arabidopsis thaliana* (each of which exhibited a dominant phenotype comprising insensitivity to ethylene) and comparing the nucleotide and deduced amino acid sequences. The invention, however, is not limited to modified ETR nucleic acids from *Arabidopsis thaliana* as described in the examples. Rather, the invention includes other readily identifiable modified ETR nucleic acids which modulate ethylene sensitivity.

The above four varieties exhibiting dominant ethylene insensitivity were generated by chemical modification of seedlings of *Arabidopsis thaliana* and identified by observing plant development from such modified seedlings with the addition of exogenous ethylene. Using a similar approach either with or without the addition of exogenous ethylene, the skilled artisan can readily generate other variants of any selected plant species which also have a modulated response to ethylene. Then, using ETR probes based upon the wild-type or modified ETR nucleic acid sequences disclosed herein, other modified ETR nucleic acids can be isolated by probing appropriate genomic or cDNA libraries of the modified selected plant species. The nucleotide and/or encoded amino acid sequence of such newly generated modified ETR nucleic acids is then preferably compared with the wild-type ETR nucleic acid from the selected plant species to determine which modifications, if any, in the ETR nucleic acid are responsible for the observed phenotype. If the wild-type sequence of the selected plant species is not available, the wild-type or modified ETR sequences disclosed herein for *Arabidopsis thaliana* or other ETR sequences which have been identified can be used for comparison. In this manner, other modifications to ETR proteins can be identified which can confer the ethylene insensitivity phenotype. Such modifications include the identification of amino acids other than those disclosed herein which can be substituted at residues equivalent to Ala-31,Ile-62, Cys-65 and Ala-102 in the *Arabidopsis thaliana* ETR protein and the identification of other amino acid residues which can be modified by substitution, insertion and/or deletion of one or more amino acid residues to produce the desired phenotype.

Alternatively, a cloned precursor ETR nucleic acid can be systematically modified such that it encodes the substitution, insertion and/or deletion of one or more amino acid residues and tested to determine the effect of such modification on a plant's ethylene response. Such modifications are preferably made within that portion of the ETR nucleic acid which encodes the amino-terminal portion of the ETR protein. However, modifications to the carboxy-terminal or putative transmembrane domains to modulate signal transduction are also contemplated (e.g., modifications of the conserved histidine of the histidine kinase domain which is the supposed site of autophosphorylation or the conserved aspartate of the response regulator domain which is the supposed site of phosphorylation). One method which may be used for identifying particular amino acid residues involved in the direct or indirect interaction with ethylene is the sequential substitution of the codons of an ETR nucleic acid with codons encoding a scanning amino acid such as glycine or alanine (See, e.g., PCT Publication W090/04788 published May 3, 1990) followed by transformation of each of the thus formed modified nucleic acids into a plant to determine the effect of such sequential substitution on the ethylene response. Other approaches include random modifications or predetermined targeted modifications of the cloned ETR nucleic acid (See, e.g., PCT Publication No. W092/07090 published Apr. 30, 1992) followed by transformation of plant cells and the identification of progeny having an altered ethylene response. The ETR nucleic acid from those plants having the desired phenotype is isolated and sequenced to confirm or identify the modification responsible for the observed phenotype.

Amino acid residues equivalent to those specifically identified in an ETR protein which can be modified to alter the ethylene response can also be readily identified in ETR proteins from other plant species. For example, equivalent amino acid residues to those identified in the ETR protein from *Arabidopsis thaliana* can be readily identified in other ETR proteins. An amino acid residue in a precursor ETR protein is equivalent to a particular residue in the ETR protein of *Arabidopsis thaliana* if it is homologous in position in either primary or tertiary structure to the specified residue of the Arabidopsis ETR protein.

In order to establish homology by way of primary structure, the primary amino acid sequence of a precursor ETR protein is directly compared by alignment with the primary sequence of the ETR protein from *Arabidopsis thaliana*. Such alignment is preferably of the amino-terminal domain and will take into account the potential insertion or deletion of one or more amino acid residues as between the two sequences so as to maximize the amino acid sequence homology. A comparison of a multiplicity of ETR protein sequences with that of *Arabidopsis thaliana* provides for the identification of conserved residues among such sequences which conservation is preferably maintained for further comparison of primary amino acid sequence. Based on the alignment of such sequences, the skilled artisan can readily identify amino acid residues in other ETR proteins which are equivalent to Ala-31, Ile-62, Cys-65, Ala-102 and other residues in *Arabidopsis thaliana* ETR protein. Such equivalent residues are selected for modifications analogous to those of other modified ETR proteins which confer the desired ethylene responsive phenotype. Such modified ETR proteins are preferably made by modifying a precursor ETR nucleic acid to encode the corresponding substitution, insertion and/or deletion at the equivalent amino acid residue.

In addition to homology at the primary sequence level, equivalent residues can be identified based upon homology at the level of tertiary structure. The determination of equivalency at this level will generally require three-dimensional crystal structures for an ETR protein or modified ETR protein from Arabidopsis (or crystal structure of another ETR protein having defined equivalent residues) and the crystal structure of a selected ETR protein. Equivalent residues at the level of tertiary structure are defined as those for which the atomic coordinates of two or more of the main chain atoms of a particular amino acid residue of the selected ETR protein, as compared to the ETR protein from Arabidopsis, are within 0.13 nm and preferably 0.10 nm after alignment. Alignment is achieved after the best model has been oriented and positioned to give the maximum overlap of atomic coordinates of non-hydrogen protein atoms of the ETR proteins in question.

ETR nucleic acids can be derived from any of the higher plants which are responsive to ethylene. Particularly suitable plants include tomato, banana, kiwi fruit, avocado, melon, mango, papaya, apple, peach and other climacteric fruit plants. Non-climacteric species from which ETR nucleic acids can be isolated include strawberry, raspberry, blackberry, blueberry, lettuce, cabbage, cauliflower, onion, broccoli, brussel sprout, cotton, canola, grape, soybean and oil seed rape. In addition, ETR nucleic acids can be isolated from flowering plants within the Division Magnoliophyta which comprise the angiosperms which include dicotyledons (Class Magnoliopsida and Dicotyledoneae) and monocotyledons (Class Liliopsida). Particularly preferred Orders of angiosperm according to "Taxonomy of Flowering Plants", by A. M. Johnson, The Century Co., NY, 1931 include Rosales, Cucurbitates, Rubiales, Campanulatae, Contortae, Tubiflorae, Plantaginales, Ericales, Primulales, Ebenales, Diapensiales, Primulales, Plumbaginales, Opuntiales, Parietales, Myritiflorae, Umbelliflorae, Geraniales, Sapindales, Rhamnales, Malvales, Pandales, Rhoendales, Sarraceniales, Ramales, Centrospermae, Santalales, Euphorbiales, Capparales, Aristolochiales, Julianiales, Juglandales, Fagales, Urticales, Myricales, Polygonales, Batidales, Balanopsidales, Proteales, Salicales, Leitneriales, Garryales, Verticiliatae and Piperales. Particularly preferred plants include lily, carnation, chrysanthemum, petunia, rose, geranium, violet, gladioli, orchid, lilac, crabapple, sweetgum, maple, poinsettia, locust, ash and linden tree.

In addition to providing a source for ETR nucleic acids which can be modified or isolated according to the teachings herein, the foregoing plants can be used as recipients of the modified nucleic acid to produce chimeric or transgenic plants which exhibit an ethylene resistance phenotype in one or more tissue types of the transformed plant.

Once a modified ETR nucleic acid has been cloned, it is used to construct vectors for transforming plant cells. The construction of such vectors is facilitated by the use of a shuttle vector which is capable of manipulation and selection in both plant and a convenient cloning host such as a prokaryote. Such shuttle vectors thus can include an antibiotic resistance gene for selection in plant cells (e.g., kanamycin resistance) and an antibiotic resistance gene for selection in a bacterial host (e.g. actinomycin resistance). Such shuttle vectors also contain an origin of replication appropriate for the prokaryotic host used and preferably at least one unique restriction site or a polylinker containing unique restriction sites to facilitate vector construction. Examples of such shuttle vectors include pMON530 (Rogers et al. (1988) *Methods in Enzymology* 153:253–277) and pCGN1547 (McBride et al. (1990) *Plant Molecular Biology* 14:269–276).

In the preferred embodiments, which comprise the best mode for practicing the invention, a promoter is used to drive expression of an ETR or a modified ETR nucleic acid within at least a portion of the tissues of a transformed plant. Expression of an ETR nucleic acid is preferably in the antisense orientation to modulate the ethylene response by reduction in translation of the endogenous ETR RNA transcript. Expression of a modified ETR nucleic acid results in the production of a modified ETR protein which is capable of conferring ethylene insensitivity. Such promoters may be obtained from plants, plant pathogenic bacteria or plant viruses. Constitutive promoters include the 35S and 19S promoters of cauliflower mosaic virus (CaMV35S and CaMV19S), the full-length transcript promoter from the Figwort mosaic virus (FMV35S) (See PCT Publication No. W092/12249 published Jul. 23, 1992) and promoters associated with Agrobacterium genes such as nopaline, synthase (NOS), mannopine synthase (MOS) or octopine synthase (OCS). Other constitutive promoters include the α-1 and β-1 tubulin promoters (Silflow et al. (1987) *Devel. Genet.* 8:435–460), the histone promoters (Chaubet (1987) *Devl. Genet.* 8:461–473) and the promoters which regulate transcription of ETR nucleic acids.

In some embodiments, tissue and/or temporal-specific promoters can be used to control expression of ETR and modified ETR nucleic acids. Examples of fruit specific promoters include the E8, E4, E17 and J49 promoters from tomato (Lincoln et al. (1988) *Mol. Gen. Genet.* 212:71–75) and the 2A11, Z130 and Z70 promoters from tomato as described in U.S. Pat. Nos. 4,943,674, 5,175,095 and 5,177,307. In addition, preferential expression in rapidly dividing tissue can be obtained utilizing the plant EF-1α promoter as described in U.S. Pat. No. 5,177,011. Examples of floral specific promoters include the leafy promoter and promoters from the apetala, pistillata and agamous genes. A promoter system for targeting expression in the leaves of a transformed plant is a chimeric promoter comprising the CaMV35S promoter ligated to the portion of the ssRUBISCO gene which represses the expression of ssRUBISCO in the absence of light. In addition, pollen-specific promoters can also be used. Such promoters are well known to those skilled in the art and are readily available. A example of such a promoter is Zn13 (Hamilton et al. (1992) *Plant Mol. Biol.* 18:211–218). This promoter was cloned from corn (Monocot) but functions as a strong and pollen-specific promoter when used in tobacco (Dicot).

Examples of inducible promoters which can be used for conditional expression of ETR nucleic acids include those from heat-shock protein genes such as the PHS1 heat-shock protein gene (Takahashi et al. (1989) *Mol. Gen. Genet.*

219:365–372) and light-inducible promoters including the three chlorophyll a/b light harvesting protein promoters (Leutwiler et al. (1986) *Nucl. Acids. Res.* 14:4051–4064) and the pre-ferredoxin promoter (Vorst et al. (1990) *Plant Mol. Biol.* 14:491–499).

In a further embodiment of the invention, the vector used to transform plant cells is constructed to target the insertion of the ETR nucleic acid into an endogenous promoter within a plant cell. One type of vector which can be used to target the integration of a modified ETR nucleic acid to an endogenous promoter comprises a positive-negative selection vector analogous to that set forth by Monsour, et al. *Nature* 336:348–352 (1988) which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it. When such an approach is used, it is preferred that a replacement-type vector be used to minimize the likelihood of reversion to the wild-type genotype.

The vectors of the invention are designed such that the promoter sequence contained in the vector or the promoter sequence targeted in the plant cell genome are operably linked to the nucleic acid encoding the ETR or modified ETR nucleic acid. When the positive strand of the ETR nucleic acid is used, the term "operably linked" means that the promoter sequence is positioned relative to the coding sequence of the ETR nucleic acid such that RNA polymerase is capable of initiating transcription of the ETR nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into ETR protein. When an antisense orientation of the ETR nucleic acid is used, all that is required is that the promoter be operably linked to transcribe the ETR antisense strand. Thus, in such embodiments, only transcription start and termination sequences are needed to provide an RNA transcript capable of hybridizing with the mRNA or other RNA transcript from an endogenous ETR gene or modified ETR nucleic acid contained within a transformed plant cell. In addition to promoters, other expression regulation sequences, such as enhancers, can be added to the vector to facilitate the expression of ETR nucleic acid in vivo.

Once a vector is constructed, the transformation of plants can be carried out in accordance with the invention by essentially any of the various transformation methods known to those skilled in the art of plant molecular biology. Such methods are generally described in *Methods and Enzymology*, Vol. 153 ("Recombinant DNA Part D") 1987, Wu and Grossman, Academic Press, eds. As used herein, the term "transformation" means the alteration of the genotype of a plant cell by the introduction of exogenous nucleic acid. Particular methods for transformation of plant cells include the direct microinjection of the nucleic acid into a plant cell by use of micropipettes. Alternatively, the nucleic acid can be transferred into a plant cell by using polyethylene glycol (Paszkowski et al. *EMBO J.* 3:2717–2722 (1984)). Other transformation methods include electroporation of protoplasts (Fromm, et al. *Proc. Natl. Acad. Sci. USA* 82:5824 (1985); infection with a plant specific virus, e.g., cauliflower mosaic virus (Hohn et al. "Molecular Biology of Plant Tumors", Academic Press, New York (1982), pp. 549–560) or use of transformation sequences from plant specific bacteria such as *Agrobacterium tumefaciens*, e.g., a Ti plasmid transmitted to a plant cell upon infection by *agrobacterium tumefaciens* (Horsch et al. *Science* 233:496–498 (1984); Fraley et al. *Proc. Natl. Acad. Sci. USA* 80:4803 (1983)). Alternatively, plant cells can be transformed by introduction of nucleic acid contained within the matrix or on the surface of small beads or particles by way of high velocity ballistic penetration of the plant cell (Klein et al. *Nature* 327:70–73 (1987)).

After the vector is introduced into a plant cell, selection for successful transformation in typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. "Protoplasts Isolation and Culture", *Handbook of Plant Cell Cultures* 1:124–176 (MacMillan Publishing Co., New York (1983); M. R. Davey, "Recent Developments in the Culture and Regeneration of Plant Protoplasts", *Protoplasts* (1983) *Lecture Proceedings,* pp. 12–29 (Birkhauser, Basil 1983); and H. Binding "Regeneration of Plants", *Plant Protoplasts,* pp. 21–73 (CRC Press, Bocaraton 1985). When transformation is of an organ part, regeneration can be from the plant callus, explants, organs or parts. Such methods for regeneration are also known to those skilled in the art. See, e.g., *Methods in Enzymology,* supra.; *Methods in Enzymology,* Vol. 118; and Klee et al. *Annual Review of Plant Physiology* 38:467–486.

A preferred method for transforming and regenerating petunia with the vectors of the invention is described by Horsch, R. B. et al. (1985) *Science* 227:1229–1231. A preferred method for transforming cotton with the vectors of the invention and regenerating plants therefrom is described by Trolinder et al. (1987) *Plant Cell Reports* 6:231–234.

Tomato plant cells are preferably transformed utilizing Agrobacterium strains by the method as described in McCormick et al., *Plant Cell Reports* 5:81–84 (1986). In particular, cotyledons are obtained from 7–8 day old seedlings. The seeds are surface sterilized for 20 minutes in 30% Clorox bleach and germinated in Plantcons boxes on Davis germination media. Davis germination media is comprised of 4.3 g/l MS salts, 20 g/l sucrose and 10 mls/l Nitsch vitamins, pH 5.8. The Nitsch vitamin solution is comprised of 100 mg/l myoinositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds are allowed to germinate for 7–8 days in the growth chamber at 25° C., 40% humidity under cool white lights with an intensity of 80 einsteins $m^2$-$s^{-1}$. The photoperiod is 16 hours of light and 8 hours of dark.

Once germination occurs, the cotyledons are explanted using a #15 feather blade by cutting away the apical meristem and the hypocotyl to create a rectangular explant. These cuts at the short ends of the germinating cotyledon increase the surface area for infection. The explants are bathed in sterile Davis regeneration liquid to prevent desiccation. Davis regeneration media is composed of 1X MS salts, 3% sucrose, 1X Nitsch vitamins, 2.0 mg/l zeatin, pH 5.8. This solution was autoclaved with 0.8% Noble Agar.

The cotyledons are pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCl, 0.2 mls of a 0.5 mg/ml solution of kinetin and 0.1 ml of a 0.2 mg/ml solution of 2,4 D. This solution is adjusted to pH 6.0 with KOH. These plates are overlaid with 1.5–2.0 mls of tobacco suspension cells (TXD's) and a sterile Whitman filter soaked in 2COO5K media. 2COO5K media is composed of 4.3 g/l Gibco MS salt mixture, 1 ml B5 vitamins (1000X stock), 30 g/l sucrose, 2 mls/l PCPA from 2 mg/ml stock, and 10 μl/l kinetin from 0.5 mg/ml stock. The cotyledons were cultured for 1 day in a growth chamber at 25° C. under cool white lights with a light intensity of 40–50 einsteins $m^2s^{-1}$ with a continuous light photoperiod.

Cotyledons are then inoculated with a log phase solution of Agrobacterium containing the modified or wild type ETR nucleic acid. The concentration of the Agrobacterium is approximately $5\times10^8$ cells/ml. The cotyledons are allowed to soak in the bacterial solution for six minutes and are then blotted to remove excess solution on sterile Whatman filter disks and subsequently replaced to the original feeder plate where they are allowed to co-culture for 2 days. After the two days, cotyledons are transferred to selection plates containing Davis regeneration media with 2 mg/l zeatin riboside, 500 μg/ml carbenicillin, and 100 μg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds continue to regenerate. Shoots develop within 3–4 months.

Once shoots develop, they are excised cleanly from callus tissue and planted on rooting selection plates. These plates contain 0.5X MSO containing 50 μg/ml kanamycin and 500 μg/ml carbenicillin. These shoots form roots on the selection media within two weeks. If no roots appear after 2 weeks, shoots are trimmed and replanted on the selection media. Shoot cultures are incubated in percivals at a temperature of 22° C. Shoots with roots are then potted when roots were about 2 cm in length. The plants are hardened off in a growth chamber at 21° C. with a photoperiod of 18 hours light and 6 hours dark for 2–3 weeks prior to transfer to a greenhouse. In the greenhouse, the plants are grown at a temperature of 26° C. during the day and 21° C. during the night. The photoperiod is 13 hours light and 11 hours dark and the plants are allowed to mature.

Once plants have been regenerated, one or more plants are selected based upon a change in the ethylene response phenotype. For example, when a modified ETR nucleic acid is used with its native promoter, selection can be based upon an alteration in any of one of the "triple responses" of seedlings from such plants. Guzman et al. (1990) *The Plant Cell* 2:523. Alternatively, or when constitutive promoters are used, various other ethylene responses can be assayed and compared to the wild type plant. Such other ethylene responses include epinasty (which is observed primarily in tomato), epision, abscission, flower petal senescence and fruit ripening. In addition to overt changes in the ethylene response, the levels of various enzymes can be determined followed by exposure to ethylene to determine the response time for the typical increase or decrease in the level of a particular protein such as an enzyme. Examples of various ethylene responses which can be used to determine whether a particular plant has a decreased response to ethylene are set forth in Chapter 7, The Mechanisms of Ethylene Action in "Ethylene in Plant Biology" 2d Ed. F. B. Abels, P. W. Morgan and M. E. Salveit, Jr., eds., San Diego, Academic Press, Inc. (1992). When a tissue and/or temporal-specific promoter or inducible promoter is used, the determination of a modulation in the ethylene response is determined in the appropriate tissue at the appropriate time and if necessary under the appropriate conditions to activate/inactivate an inducible promoter. In each case, the ethylene response is preferably compared to the same ethylene response from a wild-type plant.

The following are particularly preferred embodiments for modulating the ethylene response in fruit. However, such embodiments can be readily modified to modulate the ethylene response in vegetative tissue and flowers.

In one approach, a modified ETR nucleic acid operably linked to a constitutive promoter of moderate strength is used to reduce the ethylene response. This results in a lengthening of the time for fruit ripening.

In an alternate embodiment, a modified ETR nucleic acid operably linked to a regulatable (inducible) promoter is used so that the condition that turns on the expression of the modified ETR nucleic acid can be maintained to prevent fruit ripening. The condition that turns off the expression of the modified ETR nucleic acid can then be maintained to obtain ripening.

For example, a heat-inducible promoter can be used which is active in high (field) temperatures, but not in low temperatures such as during refrigeration. A further example utilizes an auxin or gibberellin-induced promoter such that transformed plants can be treated with commercial auxin analogs such as 2, 4-D or with commercial gibberellin analogs such as Pro-Gibb to prevent early ripening.

Alternatively, a strong constitutive promoter can be operably linked to a modified ETR nucleic acid to prevent fruit ripening. So as to allow eventual fruit ripening, the plant is also transformed with a wild-type ETR nucleic acid operably linked to an inducible promoter. Expression of the wild-type ETR nucleic acid is increased by exposing the plant to the appropriate condition to which the inducible promoter responds. When the wild-type ETR nucleic acid expression is increased, the effect of expression of the modified ETR nucleic acid is reduced such that fruit ripening occurs.

The invention can be practiced in a wide variety of plants to obtain useful phenotypes. For example, the invention can be used to delay or prevent floral senescence and abscission during growth or during transport or storage as occurs in flower beds or cotton crops (Hall, et al. (1957) *Physiol. Plant* 10:306–317) and in ornamental flowers (e.g., carnations, roses) that are either cut (Halevy, et al. (1981) *Hort. Rev.* 3:59–143) or not cut. In addition, the invention can be practiced to delay or prevent senescence and abscission of leaves and fruits in cucumber (Jackson, et al. (1972) *Can. J. Bot.* 50:1465–1471), legumes and other crops (Heck, et al. (1962) *Texas Agric. Expt. Sta. Misc. Publ. MP* 613:1–13) and ornamental plants (e.g., holly wreaths) (Curtis et al. (1952) *Proc. Am. Soc. Hort. Sci.* 560:104–108). Other uses include the reduction or prevention of bitter-tasting phenolic compounds (isocoumarins) which are induced by ethylene for example in sweet potatoes (Kitinoja (1978) "Manipulation of Ethylene Responses in Horticulture", Reid, ed., *Acta. Hort.* Vol 201, 377–42) carrots (Coxon et al. (1973) *Phyto. Chem. Istry.* 12:1881–1885), parsnip (Shattuck et al. (1988) *Hort. Sci.* 23:912) and Brassica. Other uses include the prevention of selective damage to reproductive tissues as occurs in oats and canola (Reid et al. (1985) in "Ethylene in Plant Development", Roberts, Tucker, eds. (London), Butterworths, pp. 277–286), the loss of flavor, firmness and/or texture as occurs in stored produce such as apples and watermelons (Risse et al. (1982) *Hort. Sci.* 17:946–948), russet spotting (a post-harvest disorder) which is ethylene induced in crisphead lettuce (Hyodo et al. (1978) *Plant Physiol.* 62:31–35), to promote male flower production (Jaiswal et al. (1985) *Proc. Indian Acad. Sci.* (*Plantg Sci.* 95:453–459) and to increase plant size, e.g., by delaying the formation of flowers in ornamental bromeliads (Mekers et al. (9183) *Acta Hortic* 137:217–223). Furthermore, a decrease in ethylene response can be used to delay disease developments such as the preventing of lesions and senescence in cucumbers infected with *Colletotrichum lagenarium* and to reduce diseases in plants in which ethylene causes an increase in disease development, e.g., in barley, citrus, Douglas fir seedlings, grapefruit, plum, rose, carnation, strawberry, tobacco, tomato, wheat, watermelon and ornamental plants. In addition, the invention can be used to reduce the effect of ethylene found in the environment and indirectly the effect of various environmental stresses which result in the biosynthesis of ethylene in plant tissue. For example, ethylene exists at biologically detrimental levels in localized atmospheres due to fires, automobile exhaust and industry. See, e.g., Chapter 8, Ethylene in the Environment in "Ethylene in Plant Biology", supra. In addition, the invention can be used to minimize the effect of ethylene synthesized in response to environmental stresses such as flooding, drought, oxygen deficiency, wounding (including pressure and bruising), chilling, pathogen invasion (by viruses, bacteria, fungi, insects, nematodes and the like), chemical exposure (e.g., ozone salt and heavy metal ions) and radiation.

The following is presented by way of example and is not to be construed as a limitation on the scope of the invention. Further, all references referred to herein are expressly incorporated by reference.

EXAMPLE 1

Figure 8:
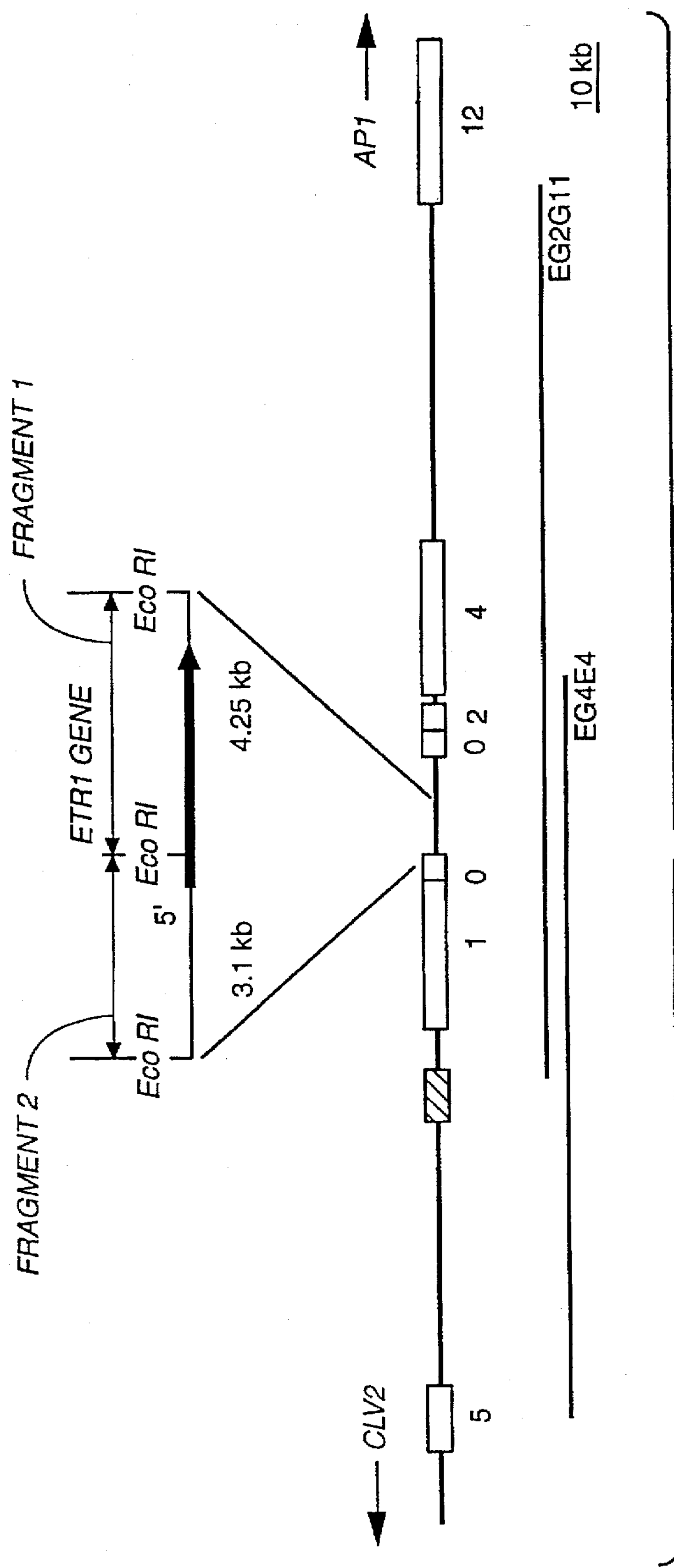
FIG. 8 depicts the structure of the cosmid insert used to localize the ETR1 gene from *Arabidopsis thaliana.* The starting position for the chromosome walk is indicated by a hatched bar. The open bars give the location and length of DNA segments used as probes to detect recombination break points. The maximum number of break points detected by each probe is shown. The numbers to the right of the ETR1 gene are out of 74 F2 recombinants between etr1-1 and ap-1, and those to the left of the ETR-1 gene are out of 25 F2 recombinants between etr1-1 and clv2. Overlapping YAC clones EG4E4 and EG2G11 are also shown.

Cloning of the ETR1 Gene ertl-1 plants were crossed with two lines carrying the recessive visible markers ap1 and clv2 respectively. The $F_1$ progeny were allowed to self-pollinate. Phenotypes were scored in the $F_2$. The recombination percentages (using the Kosambi mapping function (D. D. Kosambi (1944) *Ann. Eugen.* 12:172)) were determined in centimorgans. The ETR1 locus mapped to the lower portion of chromosome 1 between the visible genetic markers ap1 and clv2 (6.5 +/−1.0 cM from AP1 and 2.8 +/−1.1 cM from CLV2).

etr1-1 was crossed to tester line W100 (ecotype Landsberg (Koornneef et al. (1987) *Arabidopsis Inf. Serv.* 23:46) and the $F_1$ plants were allowed to self-pollinate. Linkage of RFLP markers to the ETR1 locus was analyzed in 56 $F_2$ plants as described in Chang, et al. (1988) *Proc. Natl. Acad. Sci. USA* 85:6856. Of the RFLP markers that reside in this region of chromosome 1, one marker, 1bAt315, completely cosegregated with the etr1-1 mutant phenotype out of 112 chromosomes. The 1bAt315 clone was therefore used as a probe to initiate a chromosome walk in the ETR1 gene region. Various genomic DNA cosmid libraries were utilized. One library contained subclones of two yeast artificial chromosomes (YACs EG4E4 and EG2G11 (Grill et al. (1991) *Mol. Gen. Genet.* 226:484)) that hybridized to 1bAt315. To subclone the YACs, total DNA from yeast cells harboring EG4E4 or EG2G11 was partially digested with Sau3AI, and cloned into the BglII site of cosmid vector pCIT30 (Ma et al. (1992) *Gene* 117:161). Standard cloning and screening methods were used (Sambrook et al, *Molecular Cloning: A Laboratory Manual* (Cold Spring Harbor Laboratory, Cold Spring Harbor, NY, 1989)). A library from the etr1-1 mutant was similarly constructed in pCIT30. The wild type library was constructed previously (Yanofsky et al. (1990) *Nature* 346:35). By restriction analysis and sequential hybridization to these libraries, overlapping cosmids (a contig) were obtained that spanned a distance of approximately 230 kb. See FIG. 8.

The ETR1 gene was localized to a subregion of approximately 47 kb using fine structure RFLP mapping. To create the fine structure map, meiotic recombinants were isolated based on phenotype from the F2 self-progeny of the above crosses between the etr1-1 mutant (ecotype Columbia) and two lines (both ecotype Landsberg) carrying ap1 and clv2. Recombinants were identified in the F2 progeny as plants that were either wild type at both loci or mutant at both loci. ETR1 was scored in dark grown seedlings (Bleecker et al. (1988) *Science* 241:1086). Seventy-four (74) recombinants between ETR1 and AP1 were obtained, and 25 recombinants between ETR1 and CLV2. The recombination break points were mapped using DNA fragments from the chromosome walk as RFLP probes. Given the number of recombinants isolated, the calculated average distance between break points was roughly 20 kb for each cross. Over the 230 kb contig, the actual density of break points found was consistent with the calculated density on the CLV2 side (with 5 break points in approximately 120 kb). The nearest break points flanking the ETR1 gene defined a DNA segment of approximately 47 kb.

To search for transcripts derived from this 47 kb region, cDNA libraries were screened using DNA fragments. One cDNA clone was designated λC4 and was detected with the 4.25 kb EcoRI fragment 1 shown in FIG. 8. Because λC4 potentially represented the ETR1 gene, this clone was further characterized.

EXAMPLE 2

ETR Gene Characterization

The nucleotide sequences of the λC4 cDNA and the corresponding genomic DNA (FIG. 2) SEQ ID NO:1 was determined using sequenase version 2.0 (United States Biochemical Co., Cleveland, Ohio) and synthetic oligonucleotide primers having a length of 17 nucleotides. The primer sequences were chosen from existing ETR1 sequences in order to extend the sequence until the entire sequence was determined. The initial sequence was obtained using primers that annealed to the cloning vector. Templates were double-stranded plasmids. Both strands of the genomic DNA were sequenced, including 225 bp upstream of the presumed transcriptional start site, and 90 bp downstream of the polyadenylation site. λC4 was sequenced on a single strand.

λC4 was 1812 base pairs long, including a polyA tail of 18 bases. From the DNA sequences and RNA blots (described below), it was determined that λC4 lacked approximately 1000 base pairs of the 5' end.

To obtain longer cDNAs, first strand cDNA was synthesized (RiboClone cDNA Synthesis System, Promega, Madison Wis.) from seedling polyA+ RNA using sequence-specific primers internal to λC4. The cDNA was then amplified by PCR (Saiki, R. K. et al. (1985) *Science* 230:1350) using various pairs of primers: 3' PCR primers were chosen to anneal to different exons as deduced from the cDNA and genomic DNA sequences, and 5' PCR primers were chosen to anneal to various 5' portions of genomic DNA sequences. Six different primers at the 5' end were used. The farthest upstream primer which amplified the cDNA was primer Q (5'AGTAAGAACGAAGAAGAAGTG) SEQ ID NO:26. An overlapping primer, which was shifted twelve bases downstream, also amplified the cDNA. The cDNA could not be amplified using a 5' end primer that was 98 base pairs farther upstream. Genomic DNA templates were used for PCR controls. The longest cDNA was considered to extend to the 5' end of primer Q. The amplified cDNAs were sequenced directly with Sequenase Version 2.0 as follows: after concentrating the PCR reactions by ethanol precipitation, the amplified products were separated by electrophoresis in 0.8% LMP agarose gels. The DNA fragments were excised, and a mixture of 10 ul excised gel (melted at 70° C.), 1 ml 10 mM primer and 1.2 ml 5% Nonidet P-40 was heated at 90° C. for two minutes to denature the DNA. The mixture was then cooled to 37° C. prior to proceeding with sequencing reactions.

The longest cDNA, which was 2786 bases (not including the polyA tail), was consistent with the estimated size of 2800 bases from RNA blots, and was presumed to be close to full length. A potential TATA box (5' ATAATAATAA) lies 33 bp upstream of the 5' end in the genomic sequence. Based on comparison of the cDNA and the genomic DNA sequences, the gene has six introns, one of which is in the 5' untranslated leader. The exons contain a single open reading frame of 738 amino acids. See FIG. 3.

The determination that this gene is, in fact, ETR1 was established by comparing the nucleotide sequences of the wild type allele and the four mutant alleles. For each mutant allele, an EcoRI size-selected library was constructed in the vector lambda ZAPII (Stratagene, LaJolla, Calif.). Clones of the 4.25 kb EcoRI fragment were isolated by hybridization with the wild type fragment. These clones were converted into plasmids (pBluescript vector) by in vivo excision according to the supplier (Stratagene) and sequenced. Two independent clones were sequenced on a single strand for each mutant allele. The 5' ends (535 bp not contained on the 4.25 kb EcoRI fragment) were amplified by PCR and directly sequenced as previously described. Codon differences were as follows: Codon 65 TGT to TAT in etr1-1 (FIGS. 6A, B, C and D), Codon 102 GCG to ACG in ert1-2 (FIGS. 7A, B, C and D), Codon 31 GCG to GTG in etr1-3 (FIGS. 4A, B, C and D), Codon 62 ATC to TTC in etr1-4 (FIGS. 5A, B, C and D). All four mutations are clustered in the amino-terminal region of the deduced protein sequence.

The ETR1 message was examined in standard RNA electrophoresis (formaldehyde) gel blots. The 2.8 kb ETR1 transcript was present in all plant parts examined —leaves, roots, stems, flowers and seedlings (data not shown). In addition, no differences were observed between ETR1 transcripts of the wild type and the mutant alleles (data not shown). Treatment with ethylene did not detectably alter the amount of ETR1 mRNA in dark-grown wild type seedlings (data not shown).

When the ETR1 gene was hybridized to Arabidopsis genomic DNA blots at normal stringency (i.e., overnight in 5×SSPE (0.9M NaCl, 50 mM $NaH_2PO_4$, 40 mM NaOH, 4.5 mM EDTA, pH 7.4 at 65° C., with the most stringent wash in 0.1×SSPE at 65° C. for 30 minutes), only the expected fragments of the ETR1 locus were observed (data not shown). At reduced stringency (i.e., hybridization in 5×SSPE at 50° C. and washs in 5×SSPE at 50° C.), however, numerous fragments were detected, which suggests that a family of similar genes exists in Arabidopsis.

The predicted amino terminal sequence of ETR1 (residues 1–313) has no similarity to sequences in the GenBank database (version 77.0). The carboxy-terminal portion, however, is highly similar to the conserved domains of both the sensor and the response regulator of the prokaryotic two-component system of signal transduction. In bacteria, the histidine protein kinase domain of the sensor is characterized by five sequence motifs arranged in a specific order with loosely conserved spacing (Parkinson (1992) *Annu. Rev. Genet.* 26:71). The deduced ETR1 sequence contains all five motifs with the same relative order and spacing found in the bacterial proteins (FIG. 9A). The deduced sequence is most similar to the sequences of *Escherichia coli* Bar A (Nagasawa et al. (1992) *Mol. Microbiol.* 6:3011) and *Pseudomonas syringae* LemA (Harbak et al. (1992) *J. Bact.* 174:3011); over the entire histidine kinase domain (the 241 amino acids from residues 336 through 566), there are 43% and 41% amino acid identities with BarA and LemA respectively, and 72% and 71% similarities respectively. The function of BarA is unknown, although it was cloned based on its ability to complement a deletion in the *E. coli* osmotic sensor protein, EnvZ (Nagasawa, supra.). LemA is required for pathogenicity of *P. syringae* on bean plants (Hrabak, supra.). Other bacterial proteins with sequences highly similar to this putative ETR1 domain are: *Xanthomonas campestris* RpfC (35% identity) which is possibly involved in host recognition for pathogenicity in cruciferous plants (Tang et al (1991) *Mol. Gen. Genet.* 226:409), *E. coli* RcsC (34% identity) which is involved in regulation of capsule synthesis (Stout et al. (1990) *J. Bacteriol.* 172:659) and *E. coli* ArcB (25% identity) which is responsible for repression of anaerobic enzymes (Luchi et al. (1990) *Mol. Microbiol.* 4:715).

Adjacent to the putative histidine kinase domain, the deduced ETR1 sequence exhibits structural characteristics and conserved residues of bacterial response regulators. Structural characteristics of response regulators are based on the known three-dimensional structure of CheY (the response regulator for chemotaxis) in *Salmonella typhimurium* and *E. coli,* which consists of five parallel β-strands surrounded by five α-helices (Stock et al. (1989) *Nature* 337:745; Volz et al. (1991) *J. Biol. Chem.* 266:15511). Sequences of bacterial response regulators have been aligned to this structure based on residues that are compatible with the hydrophobic core of the CheY (Stock et al. (1989) *Microbiological Rev.* 53:450). The deduced ETR1 sequence can be similarly aligned (data not shown). At four specific positions, response regulators contain highly conserved residues—three aspartates and a lysine (Parkinson et al. (1992) *Annu. Rev. Genet.* 26:71; Stock et al., supra.); the three aspartates form an acidic pocket into which protrudes the side chain of the conserved lysine (Stock et al. (1989) *Nature* 337:745; Volz et al. (1991) *J. Biol. Chem.* 266:15511) and the third aspartate is the receiver of the phosphate from phosphohistidine (Stock et al. (1989), supra.). Except for the conservative substitution of glutamate for the second aspartate, these conserved amino acids are found in the same positions in the deduced ETR1 sequence (FIG. 9B). The deduced sequence in this domain (a stretch of 121 amino acids from residues 609 through 729 in ETR1) is most similar to the sequences of Bordetella parapertussis BvgS (29% identity, 60% similarity) which controls virulence-associated genes for pathogenicity in humans (Aricò et al. (1991) *Mol. Microbiol.*5:2481), *E. coli* RcsC (29% identity, 64% similarity), *P. syringae* LemA (26% identity, 57% similarity), *X. campestris* RpfC (25% identity) and *E. coli* BarA (20% identity). All of the bacterial proteins that are similar to ETR1 in sequence are also structurally similar to ETR1 in that they contain both the histidine kinase domain and the response regulator domain. Although these features are shared, the sensing functions are clearly diverged.

A potential membrane spanning domain (residues 295–313) exists in the deduced ETR1 sequence based on hydropathy analysis (Kyte et al. (1982) *J. Mol. Biol.* 157:105), but it is unclear whether ETR1 is actually a transmembrane protein since there is no clear signal sequence. There are also no N-linked glycosylation sites. While all of the bacterial proteins to which the deduced ETR1 sequence is similar have two potential membrane spanning domains flanking the amino terminal domain, a few bacterial sensors (those which lack the response regulator) do not.

EXAMPLE 3

The etr1 Gene Confers Ethylene Insensitivity to Wild Type Plants

Dominant ethylene insensitivity was conferred to wild type Arabidopsis plants when the etr1-1 mutant gene was stably introduced using Agrobacterium-mediated transformation. The gene was carried on a 7.3 kb genomic DNA fragment (fragments 1 and 2 in FIG. 8 which included approximately 2.7 kb upstream of the transcription initiation site, and approximately 1 kb downstream of the polyadenylation site). It was cloned into binary transformation vector pCGN1547 obtained from Calgene, Inc., Davis, Calif. The vector also carried a selectable marker for kanamycin resistance in plants.

For the etr1-1 construct, the 4.25 kb EcoRI plasmid clone containing the etr1-1 mutation was linearized by partial EcoRI digestion and ligated with the 3.1 kb EcoRI fragment which was agarose gel-purified from cosmid clone theta8 (a subclone of YAC EG4E4 in the walk). The resulting plasmid, containing the two EcoRI fragments in the correct relative orientation, was linearized at polylinker site Asp718, the ends were filled in using Klenow enzyme, and BamHI linkers were ligated to the blunt ends. Finally, the 7.3 kb insert was removed from the plasmid at the polylinker site BamHI, and ligated into the BamHI site of binary transformation vector pCGN1547 (McBride, K. E. et al. (1990) *Plant Molecular Biology,* 14:269). For the control construct, the wild type 7.3 kb fragment was agarose gel-purified from EcoRI partially digested cosmid theta8, and subcloned into the EcoRI site of pBluescript. The fragment was then removed using the BamHI and KpnI sites of the polylinker, and ligated into pCGN1547 that had been digested with BamHI and KpnI. The mutant and wild type constructs were transformed into Agrobacterium (Holsters et al. (1978) *Mol. Gen. Genet.* 163:181) strain ASE (Monsanto) (Rogers et al. (1988) *Meth. Enzymol.* 153:253). Arabidopsis ecotype Nossen was transformed (Valvekens, D. et al. (1988) *Natl. Proc. Acad. Sci. USA* 85:5536) using root-tissue cultured in liquid rather than on solid medium. Triploid plants having one mutant copy of the ETR1 gene were obtained as the progeny of crosses between the etr1-1 homozygote (diploid) and a tetraploid wild type in ecotype Bensheim which has the same triple response phenotype as ecotype Columbia. Triploid wild type plants were similarly obtained by crossing the diploid wild type to the tetraploid. Ethylene sensitivity was assayed in dark-grown seedlings treated with either ethylene (Bleecker et al., supra.) or 0.5 mM ACC. For ACC treatment, plants were germinated and grown on Murashige and Skoog basal salt mixture (MS, Sigma), pH 5.7, 0.5 mM ACC (Sigma), 1% Bacto-agar (Difco). Kanamycin resistance was measured by the extent of root elongation in one week old seedlings grown on MS pH 5.7 μg/ml Kanamycin, 1% Bacto-agar.

Ten kanamycin resistant plants were produced. Eight of the ten exhibited ethylene insensitive self-progeny as evaluated by the dark-grown seedling response to ethylene. In each line, ethylene insensitivity cosegregated with kanamycin resistance. As a control, transformations were performed using the corresponding 7.3 kb genomic DNA fragment of the wild type from which six kanamycin resistant plants were obtained. These lines gave rise to only ethylene sensitive self-progeny which did not appear to be different from the wild type.

The etr1-1 transformants displayed different levels of ethylene insensitivity. Thus, the wild type gene is capable of attenuating the mutant phenotype and the etr1-1 mutation is not fully dominant in the transformed plants. Of the ten kanamycin resistant lines, six gave completely dominant ethylene insensitivity, indicating the presence of multiple copies of the mutant gene. Two other lines displayed partial dominance, and two lines appeared to be wild type. Reduced ethylene insensitivity was presumably due to low expression levels which can be caused by position effects (e.g., DNA methylation) or possibly by truncation of the transferred DNA.

EXAMPLE 4

Vector Constructs Containing Heterologous Promoter

This example describes the construction of a plant transformation vector containing a heterologous promoter to control expression of wild type and mutant ETR1 nucleic acids.

The cauliflower mosaic virus 35S protein promoter (Guilley et al. (1982) *Cell* 30:763–773; Odell, et al. (1985) *Nature* 313:810–812 and Sanders et al. (1987) *Nucl. Acids Res.* 15:1543–1558) and the 3' end of the Nopaline synthase (NOS) gene were cloned into the pCGN1547 vector to create pCGN18. The 35S promoter, on a HindIII-BamHI fragment of approximately 1.6 kb, was cloned into the unique HindIII-BamHI site of pCGN1547. The 1 kb BamHI-KpnI NOS fragment was cloned into the unique BamHI-KpnI site of pCGN1547.

The 4.25 kb EcoRI fragment of both the wild type and mutant ETR1-1 allele were independently cloned into the unique BamHI site of the above pCGN18 vector using BamHI linkers. This 4.25 kb EcoRI genomic fragment contains the entire coding sequence including five introns and approximately 1 kb genomic DNA downstream of the polyadenylation site. It does not contain the ETR1 promoter which is on the 3.1 EcoRI fragment 2 in FIG. 5.

These vectors were used to transform root explants as described in Example 3. Kanamycin resistant plants containing the mutant ETR1-1 gene are obtained and demonstrate an ethylene insensitivity phenotype similar to that found in Example 3. Control plants transformed with the wild type ETR1 gene produce only ethylene sensitive self-progeny.

Having described the preferred embodiments of the invention, it will appear to those of ordinary skill in the art that various modifications may be made to the disclosed embodiments, and that such modifications are intended to be within the scope of the invention.

All references are expressly incorporated herein by reference.

What is claimed is:

1. A tomato plant comprising plant cells transformed with a modified ETR nucleic acid comprising the modification of a codon of an ETR nucleic acid to substitute or delete an amino acid residue within the 313 N-terminal portion of the encoded ETR protein, wherein said ETR protein is at least 60% homologous and said N-terminal portion is at least 70% homologous to the ETR protein sequence of *Arabidopsis thaliana* as set forth in Seq. ID NO. 3, and wherein said tomato plant has a phenotype characterized by a decrease in response of said transformed plant cells to ethylene as compared to a wild-type tomato plant cells not containing said modified ETR nucleic acid.

2. The tomato plant of claim 1 wherein said codon is selected from the group encoding amino acid residues equivalent to Ala-31, Ile-62, Cys-65, and Ala-102 in said *Arabidopsis thaliana* ETR protein sequence.

3. The fruit from the plant of claim 1.

4. A modified ETR nucleic acid comprising the modification of a codon of an ETR nucleic acid to substitute or delete an amino acid residue within the 313 amino acid N-terminal portion of the encoded ETR protein, wherein said ETR protein is at least 60% homologous and said N-terminal portion is at least 70% homologous to the ETR protein sequence of *Arabidopsis thaliana* as set forth in Seq. ID No. 3.

5. A tomato plant cell transformed with the nucleic acid of claim 4.

6. A method for producing a tomato plant comprising:

(a) transforming a tomato plant cell with the modified ETR nucleic acid of claim 4;

(b) regenerating pints from the transformed tomato plant cell; and (c) selecting at least one tomato plant having a decreased response to ethylene.

7. The tomato plant of claim 1 wherein the modified ETR nucleic acid encodes a modified ETR protein in which the N-terminal portion has 85% or more homology to amine acid residues 1 to 313 of the ETR protein of *Arabidopsis thaliana* as set forth in Seq. ID. No. 3, and wherein said ETR protein is at least 75% homologous to said ETR protein of *Arabidopsis thaliana*.

8. The tomato plant of claim 1 wherein the modified ETR nucleic acid encodes a modified ETR protein in which the N-terminal portion has 95% or more homology to amine acid residues 1 to 313 of the ETR protein of *Arabidopsis thaliana* as set forth in Seq. ID. No. 3, and wherein said ETR protein is at least 90% homologous to said ETR protein of *Arabidopsis thaliana*.

* * * * *

UNITED STATES PATENT AND TRADEMARK OFFICE

CERTIFICATE OF CORRECTION

PATENT NO. : 5,689,055

DATED : November 18, 1997

INVENTOR(S) : MEYEROWITZ et al.

It is certified that error appears in the above-identified patent and that said Letters Patent is hereby corrected as shown below:

Column 87, line 48, Claim 1, immediately preceding "N-Terminal" insert --amino acid--.

Column 88, line 49, Claim 6, delete "pints" and insert therefor --plants--.

Column 88, line 55, Claim 7, delete "amine" and insert therefor --amino--.

Column 88, line 61, Claim 8, delete "amine" and insert therefor --amino--.

Signed and Sealed this

Twelfth Day of May, 1998

Attest:

BRUCE LEHMAN

*Attesting Officer* *Commissioner of Patents and Trademarks*